US012576149B2

(12) United States Patent
Aoi et al.

(10) Patent No.: US 12,576,149 B2
(45) Date of Patent: Mar. 17, 2026

(54) GAMMA DELTA T CELLS DERIVED FROM INDUCED PLURIPOTENT STEM CELLS, AND PRODUCTION METHOD THEREFOR

(71) Applicant: NATIONAL UNIVERSITY CORPORATION KOBE UNIVERSITY, Hyogo (JP)

(72) Inventors: Takashi Aoi, Hyogo (JP); Nobuyuki Murai, Hyogo (JP)

(73) Assignee: NATIONAL UNIVERSITY CORPORATION KOBE UNIVERSITY, Hyogo (JP)

( * ) Notice: Subject to any disclaimer, the term of this patent is extended or adjusted under 35 U.S.C. 154(b) by 66 days.

(21) Appl. No.: 19/019,930

(22) Filed: Jan. 14, 2025

(65) Prior Publication Data

US 2025/0213693 A1     Jul. 3, 2025

Related U.S. Application Data

(63) Continuation of application No. 18/274,725, filed as application No. PCT/JP2022/004542 on Feb. 4, 2022.

(30) Foreign Application Priority Data

Feb. 5, 2021     (JP) ................................. 2021-017831

(51) Int. Cl.
| | |
|---|---|
| *A61K 40/42* | (2025.01) |
| *A61K 40/11* | (2025.01) |
| *A61K 40/32* | (2025.01) |
| *A61P 35/00* | (2006.01) |
| *C07K 14/725* | (2006.01) |
| *C12N 5/00* | (2006.01) |
| *C12N 5/0783* | (2010.01) |

(52) U.S. Cl.
CPC ............ *A61K 40/421* (2025.01); *A61K 40/11* (2025.01); *A61K 40/32* (2025.01); *A61K 40/42* (2025.01); *A61P 35/00* (2018.01); *C07K* *14/7051* (2013.01); *C12N 5/0037* (2013.01); *C12N 5/0636* (2013.01)

(58) Field of Classification Search
CPC ...................................................... A61K 40/11
See application file for complete search history.

(56) References Cited

FOREIGN PATENT DOCUMENTS

WO     WO2018147801     *  8/2018   ........... C12N 5/0783

OTHER PUBLICATIONS

Zhang et al., "Antiproliferative and Immunoregulatory Effects of Azelaic Acid Against Acute Myeloid Leukemia via the Activation of Notch Signaling Pathway," Frontiers in Pharmacology 10:1396, Nov. 29, 2019. (13 pages).
Office Action, dated Apr. 30, 2025, for Japanese Patent Application No. 2022-579629 [with English Translation]. (8 pages).

* cited by examiner

*Primary Examiner* — Elly-Gerald Stoica
(74) *Attorney, Agent, or Firm* — Seed Intellectual Property Law Group LLP

(57) ABSTRACT

Provided is a γδ T cell for securing the purity and number of cells sufficient for treatment. Also provided is a method of generating the γδ T cell. More specifically, provided are homogeneous γδ T cells excellent in that the γδ T cells are not affected by exhaustion of the cells. The foregoing is achieved by γδ T cells obtained by subjecting induced pluripotent stem cells (iPS cells) to differentiation induction treatment. Specifically, the foregoing is achieved by γδ T cells generated by subjecting iPS cells having a rearranged γδ TCR gene (γδ TCR-type iPS cells) to differentiation induction treatment. According to the method of generating the γδ T cell of the present invention, there can be provided γδ T cells and a cell population of γδT cells that have an excellent function of having antigen-specific cytotoxic activity in an MHC-unrestricted manner, and that are more homogeneous and have a higher effect than γδ T cells separated from peripheral blood.

20 Claims, 55 Drawing Sheets

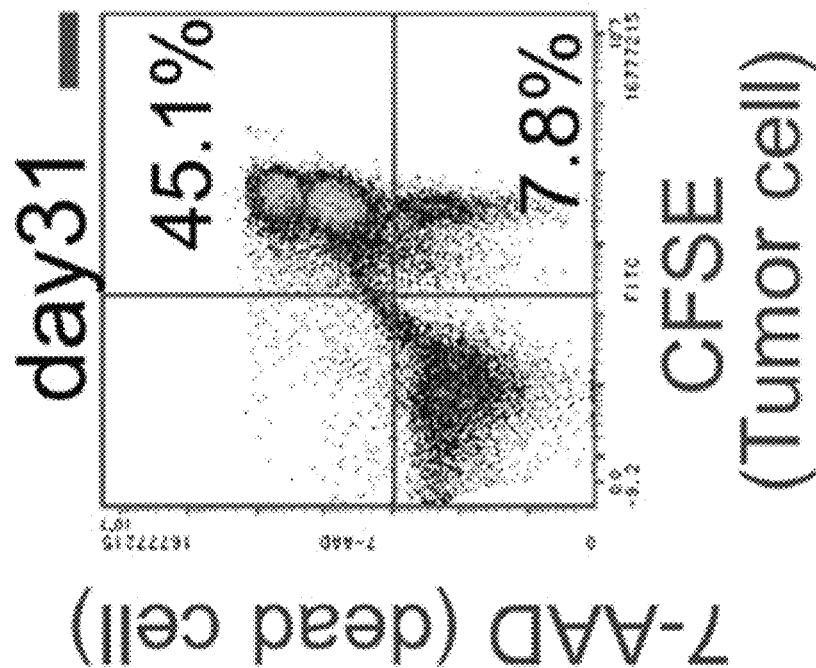
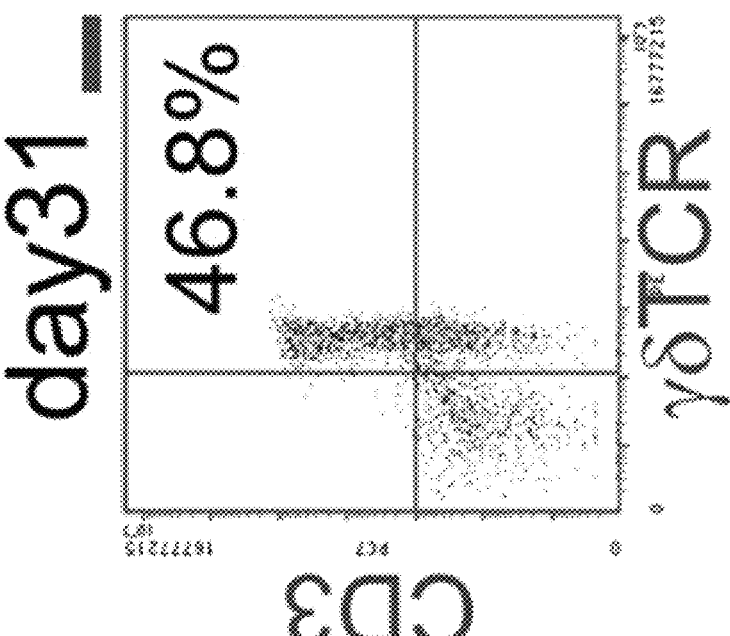
*Fig. 1B* day37

PHASE-CONTRAST MICROGRAPH

StemSpan med

γδT CELL STIMULANT     (—)

PHASE-CONTRAST MICROGRAPH gdT stim med.
10%FBS/RPMI
+HMBPP+IL2

γδT CELL STIMULANT     (+)

day32

FIG. 12

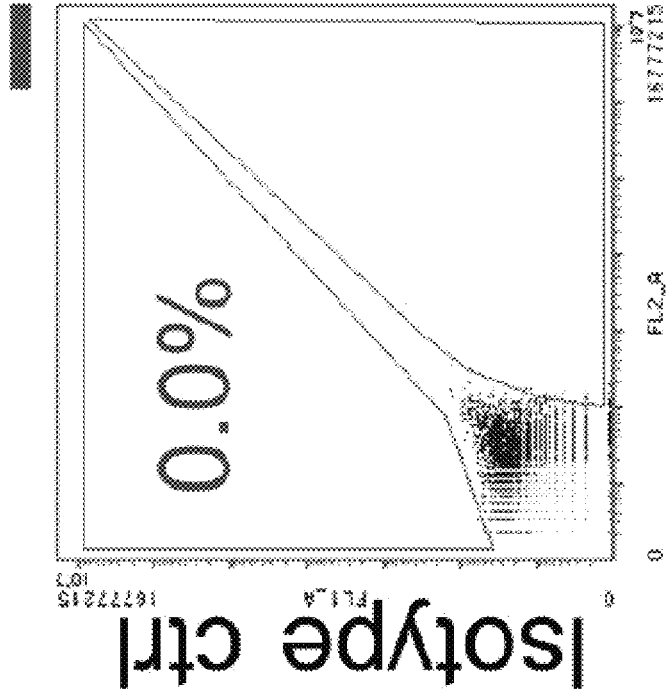
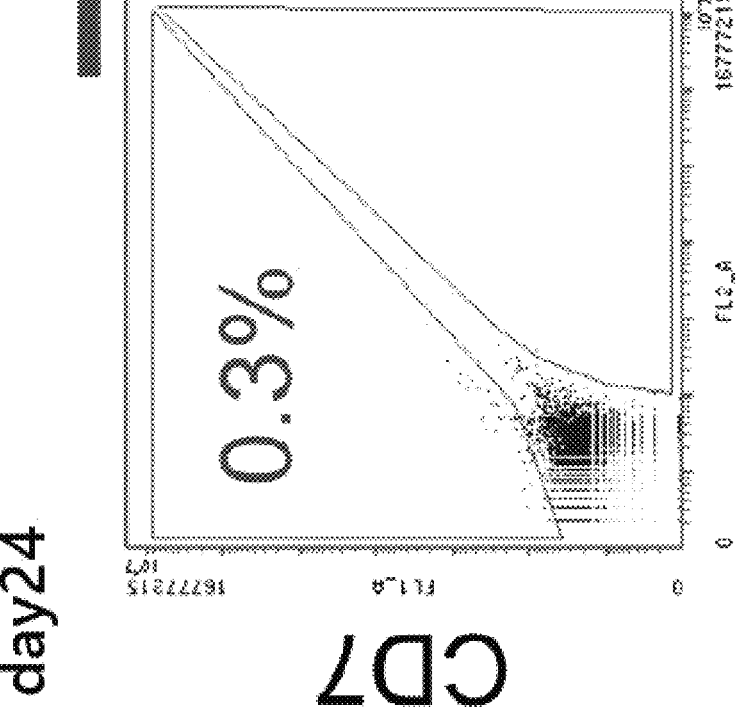
*Fig. 14*

| | | Stampro34 SFM | | αMEM+20%FBS | RPMI+FBS |
|---|---|---|---|---|---|
| AK02N | Essential8 | | | | |
| VEGF | SCF | VEGF | Flt3L | Flt3L | 2-Me |
| CHIR | SB43152 | SCF | SCF | SCF | IL-2 |
| BMP4 | bFGF | Flt-3L | IL-6 | IL-2 | Zoledronate/HMBPP |
| | | IL-6 | | IL-7 | |
| | | IL-3 | | TPO | |
| | | EPO | | Ascorbic acid | |
| | feeder free | | | OP9/N-DLL1 coculture | feeder free |

*HPC differentiation* | *Tcell differentiation* | *Tcell maturation*

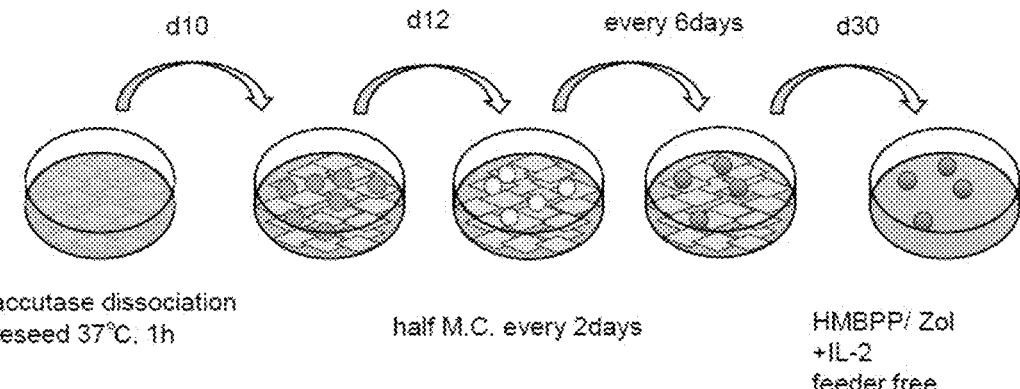

| d10 | d12 | every 6days | d30 | accutase dissociation
reseed 37°C, 1h half M.C. every 2days

HMBPP/ Zol
+IL-2
feeder free

FIG. 15B

Jurkat

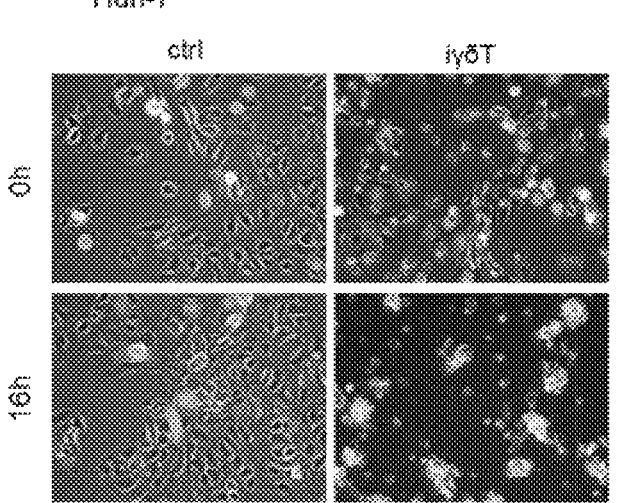
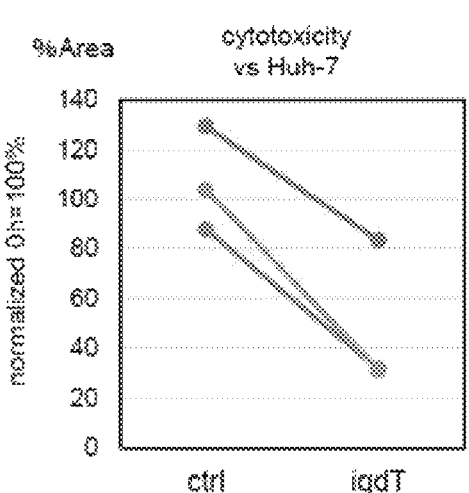
FIG. 17B

A: iPS CELL-DERIVED γδT CELLS

B: PERIPHERAL BLOOD-DERIVED γδT CELLS

C: PERIPHERAL BLOOD EXCLUDING γδT CELLS

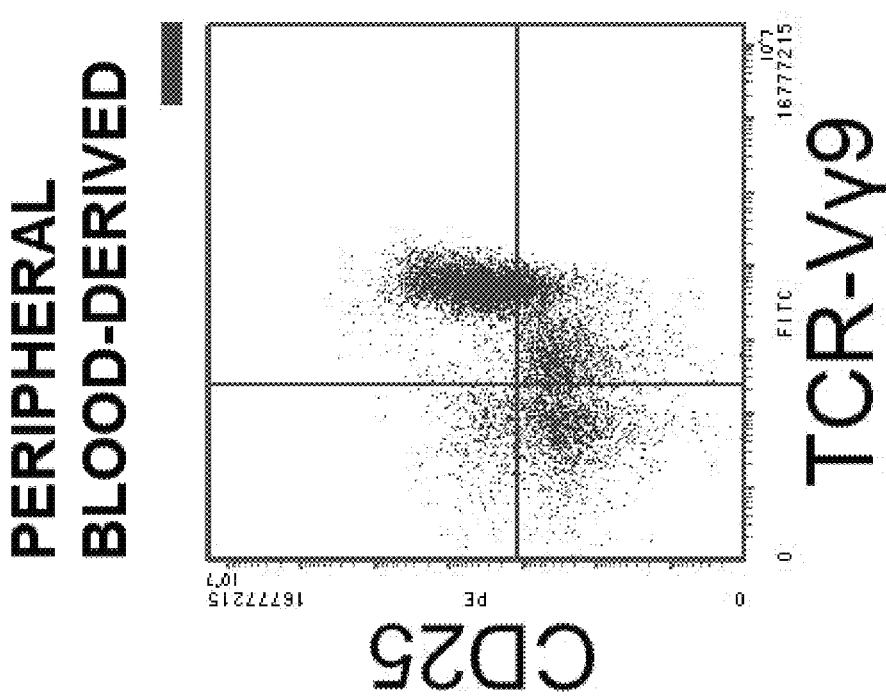
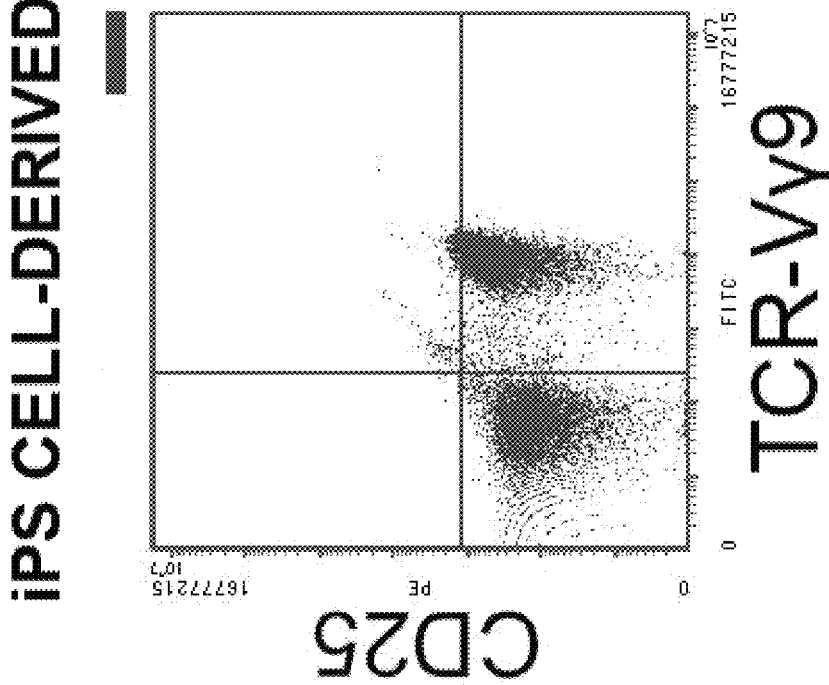
*Fig. 20* d37

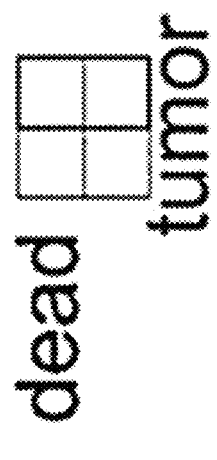
FIG. 28
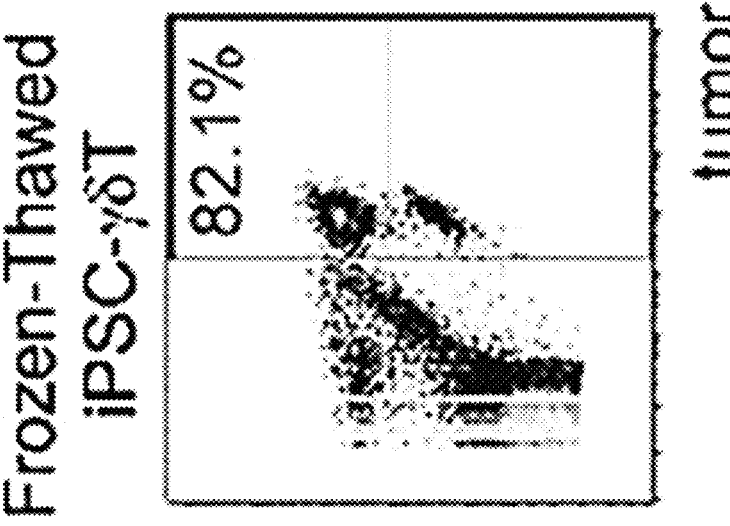

FIG. 29C

Culture under the condition for undifferentiated cells

1

GAMMA DELTA T CELLS DERIVED FROM INDUCED PLURIPOTENT STEM CELLS, AND PRODUCTION METHOD THEREFOR

TECHNICAL FIELD

The present invention relates to an induced pluripotent stem cell (iPS cell)-derived γδ T cell and a method of generating the same. Specifically, the present invention relates to an iPS cell-derived γδ T cell, the T cell acting in a MHC-unrestricted manner, and a method of generating the same. The present invention also relates to a cell population including the generated iPS cell-derived γδ T cell.

The present application claims priority from Japanese Patent Application No. 2021-017831, which is incorporated herein by reference.

BACKGROUND ART

Human mature T cells are broadly classified into two groups: αβ T cells having a T cell receptor made up of an α-chain and a β-chain; and γδ T cells having a T cell receptor made up of a γ-chain and a δ-chain. It is known that the αβT cells are extremely diverse, and αβ T cells of a single kind can attack few kinds of cells owing to MHC restriction, whereas in the γδ T cells, γδ T cells of a single kind attack many kinds of cancer cells in a MHC-unrestricted manner. The γδ T cells recognize and directly damage many kinds of cancer cells with a single kind of T cell receptor (TCR). However, the γδ T cells are generally present at a proportion of only from 1% to 5% in peripheral blood. Accordingly, there is a problem in that the purity and number of cells sufficient for the treatment cannot be secured by collecting a small amount of blood and activating and/or growing γδ T cells. In addition, when the amount of blood to be collected from a patient is increased in order to secure the purity and number of cells sufficient for the treatment, there is also a problem in that a tremendous burden is put on the patient. Treatment involving ex vivo expanding γδT cells separated from peripheral blood of a patient and infusing the resultant cells into the patient has already been put into practice. However, such method has not achieved sufficient expansion and activation owing to difficulty in securing the number of cells, and to exhaustion of cells.

There are disclosures of methods of generating iPS cells having a rearranged γδTCR gene (γδTCR-type iPS cells) (Patent Literature 1 and Non Patent Literature 1). In each of Patent Literature 1 and Non Patent Literature 1, there is also a disclosure that the γδTCR-type iPS cells were induced to differentiate into hematopoietic progenitor cells. However, there is no disclosure that the hematopoietic progenitor cells were further induced to differentiate into T cells.

There is a disclosure of a method of inducing T cell-derived iPS cells to differentiate into T cells (Patent Literature 2). In addition, it has been reported that, when iPS cells are generated from T cells harboring cancer antigen-specific TCR gene rearrangement, and are induced to differentiate, T cells harboring the same rearrangement as the original cells can be obtained. There are reports that: CD8⁺αβT cell-derived human iPS cells were induced to differentiate, to thereby regenerate human tumor antigen-specific αβT cells (Non Patent Literature 2); and human tumor antigen-specific αβT cells obtained by differentiation induction showed cytotoxicity in an antigen-specific manner (Non Patent Literature 3, and Patent Literatures 3 and 4). There is a report that, when iPS cells are generated from T cells harboring tumor antigen-specific TCR gene rearrangement, and are induced to differentiate, T cells harboring the same rearrangement as the original cells are obtained. However, each of the reports relates to αβT cells, and there is no disclosure of γδT cells. The above-mentioned αβT cells are each a cell having a particular αβTCR, and hence patients who can be treated therewith have been limited because of a small number of kinds of cancers expressing an antigen of interest, and the presence of MHC restriction.

There are reports that T cells obtained by inducing differentiation of stem cells, such as ES cells or iPS cells, showed a γδT cell-like phenotype (Non Patent Literature 4 and Patent Literature 5). However, the T cells described in the above-mentioned literatures, though found to have similarities to γδT-characteristic phenotypes in a gene expression pattern and the like, cannot be said to be T cells that actually express a γδT cell receptor, thereby recognizing an antigen and damaging target cells, that is, γδT cells.

There is a demand for a method of effectively preparing T cells capable of attacking many kinds of cancer cells in a MHC-unrestricted manner.

CITATION LIST

Patent Literature

[PTL 1] WO 2018/143243 A1 (PCT/JP2018/003120)
[PTL 2] WO 2011/096482 A1
[PTL 3] WO 2016/010153 A1
[PTL 4] WO 2016/010155 A1
[PTL 5] WO 2014/165707 A2

Non Patent Literature

[NPL 1] Stem cells translational medicine, 7(1), 34-44 (2018)
[NPL 2] Cell Stem Cell, 12, 31-36 (2013)
[NPL 3] Cancer Research, 76(23), 6839 (2016)
[NPL 4] Nat Biotechnol, 31, 928-3 (2013)

SUMMARY OF INVENTION

Technical Problem

γδT cells are generally present at a proportion of only from 1% to 5% in peripheral blood, and hence have had a problem in that the purity and number of cells sufficient for treatment cannot be secured. In addition, there has also been a problem in that, when the amount of blood to be collected is increased in order to secure the purity and number of cells sufficient for treatment, a tremendous burden is put on a person from which blood is collected. A method involving ex vivo expanding γδT cells separated from peripheral blood has not achieved sufficient expansion and activation owing to difficulty in securing the number of cells, and to exhaustion of the cells.

An object of the present invention is to effectively generate and provide γδT cells. More specifically, the object is to provide homogeneous γδT cells excellent in that the γδT cells are not affected by exhaustion of the cells.

Solution to Problem

The inventors of the present invention have made extensive investigations on a differentiation induction treatment method with their attention focused on iPS cells in order to achieve the above-mentioned object, and as a result, have succeeded in generating excellent γδT cells that retain the function of γδT cells. Thus, the inventors have completed the present invention.

That is, the present invention includes the following.

1. An induced pluripotent stem cell (iPS cell)-derived γδT cell, which is a T cell derived from an iPS cell, wherein the T cell has antigen-specific cytotoxic activity in a MHC-unrestricted manner.

2. The iPS cell-derived γδT cell according to the above-mentioned item 1, wherein the iPS cell is an iPS cell of non-αβT cell origin.

3. The iPS cell-derived γδT cell according to the above-mentioned item 1 or 2, wherein the iPS cell is an iPS cell having a rearranged γδTCR gene.

4. An iPS cell-derived γδT cell, which is generated by subjecting an iPS cell having a rearranged γδTCR gene to differentiation induction treatment.

5. A method of generating an iPS cell-derived γδT cell, including a step of culturing a hematopoietic progenitor cell, which is obtained by subjecting an iPS cell having a rearranged γδTCR gene to differentiation induction treatment, using a medium obtained by supplementing a basal medium with one kind or a plurality of kinds selected from FMS-like tyrosine kinase 3 ligand (FLT3L), stem cell factor (SCF), IL-2, IL-7, thrombopoietin (TPO), and L-ascorbic acid.

6. The method of generating an iPS cell-derived γδT cell according to the above-mentioned item 5, further including, after the step of culturing a hematopoietic progenitor cell using a medium obtained by supplementing a basal medium with one kind or a plurality of kinds selected from FLT3L, SCF, IL-2, IL-7, TPO, and L-ascorbic acid, a step of culturing the resultant cell using a medium containing a γδT cell stimulant.

7. The method of generating an iPS cell-derived γδT cell according to the above-mentioned item 5 or 6, wherein the step of culturing a hematopoietic progenitor cell using a medium obtained by supplementing a basal medium with one kind or a plurality of kinds selected from FLT3L, SCF, IL-2, IL-7, TPO, and L-ascorbic acid is a step of culturing the hematopoietic progenitor cell by coculture with a feeder cell.

8. The method of generating an iPS cell-derived γδT cell according to the above-mentioned item 5 or 6, wherein the step of culturing a hematopoietic progenitor cell using a medium obtained by supplementing a basal medium with one kind or a plurality of kinds selected from FLT3L, SCF, IL-2, IL-7, TPO, and L-ascorbic acid is a step of culturing the hematopoietic progenitor cell without coculture with a feeder cell.

9. The method of generating an iPS cell-derived γδT cell according to the above-mentioned item 8, wherein the step of culturing the hematopoietic progenitor cell without coculture with a feeder cell includes a step of culturing the hematopoietic progenitor cell using a culture substrate coated with: vascular cell adhesion molecule-1 (VCAM1); and delta-like protein 4 (DLL4) or delta-like protein 1 (DLL1).

10. The method of generating an iPS cell-derived γδT cell according to the above-mentioned item 8 or 9, wherein the step of culturing the hematopoietic progenitor cell without coculture with a feeder cell further includes a step of culturing the hematopoietic progenitor cell using a medium containing DKK1 and/or azelaic acid (AZA).

11. The method of generating an iPS cell-derived γδT cell according to any one of the above-mentioned items 6 to 10, wherein the medium containing a γδT cell stimulant is a medium containing the γδT cell stimulant and one kind or a plurality of kinds selected from IL-2 and IL-15.

12. The method of generating an iPS cell-derived γδT cell according to any one of the above-mentioned items 6 to 11, wherein the γδT cell stimulant is a phosphoric acid compound or a derivative thereof, which is a metabolite of an isoprenoid biosynthesis pathway, or a specific inhibitor of a farnesyl pyrophosphate (FPP) synthase serving as a rate-limiting enzyme of the isoprenoid biosynthesis pathway.

13. The method of generating an iPS cell-derived γδT cell according to any one of the above-mentioned items 6 to 12, wherein the culturing step is performed under a serum-free condition.

14. The method of generating an iPS cell-derived γδT cell according to any one of the above-mentioned items 6 to 13, wherein the culturing step is performed under a hypoxic condition.

15. An iPS cell-derived γδT cell, which is generated by the method of generating an iPS cell-derived γδT cell of any one of the above-mentioned items 5 to 14.

16. A cell population, including the iPS cell-derived γδT cell of any one of the above-mentioned items 1 to 4 and 15.

17. The cell population according to the above-mentioned item 16, wherein the cell population including the iPS cell-derived γδT cell has higher cytotoxic activity in an antigen-specific manner than a cell population of γδT cells separated from peripheral blood.

18. A cell population including γδT cells, the cell population including γδT cells, which have base sequences identical to each other in a CDR3 region of a TCR gene, at a ratio of 90% or more with respect to the γδT cells that make up the cell population.

19. The cell population according to the above-mentioned item 18, wherein the cell population includes $1 \times 10^5$ or more γδT cells.

20. A cell population including γδT cells, the cell population including γδT cells, which show a higher expression amount than γδT cells separated from peripheral blood in terms of expression amounts of CD7 and CD8a, at a ratio of 90% or more with respect to the γδT cells that make up the cell population.

21. The cell population including γδT cells according to any one of the above-mentioned items 18 to 20, wherein 10% or less of the γδT cells that make up the cell population are undifferentiated cells.

22. An antigen-specific cellular immunotherapeutic agent, including the iPS cell-derived γδT cell of any one of the above-mentioned items 1 to 4 and 15 as an active ingredient.

23. A method of culturing the iPS cell-derived γδT cell of any one of the above-mentioned items 1 to 4 and 15, including culturing the iPS cell-derived γδT cell in a liquid medium using a medium containing a bead-like carrier.

24. A therapeutic agent for a disease, such as cancer, an infectious disease, or an autoimmune disorder, the therapeutic agent including the iPS cell-derived γδT cell of any one of the above-mentioned items 1 to 4 and 15 as an active ingredient.

25. A pharmaceutical composition, including the iPS cell-derived γδT cell of any one of the above-mentioned items 1 to 4 and 15 as an active ingredient.

26. An antigen-specific cellular immune cell treatment method, including administering the iPS cell-derived γδT cell of any one of the above-mentioned items 1 to 4 and 15.

27. A treatment method for a disease, such as cancer, an infectious disease, or an autoimmune disorder, the method including administering the iPS cell-derived γδT cell of any one of the above-mentioned items 1 to 4 and 15.

Advantageous Effects of Invention

According to the method of generating an iPS cell-derived γδT cell through iPS cell differentiation induction treatment of the present invention, γδT cells can be effectively generated without a burden on a person from which blood is collected, and without being affected by exhaustion of the cells. Further, according to the method of generating an iPS cell-derived γδT cell of the present invention, excellent γδT cells can be generated even under a feeder cell- and/or serum-free condition, or an animal-derived component-free condition. The γδT cell of the present invention has an excellent function of having antigen-specific cytotoxic activity in a MHC-unrestricted manner, and has been able to provide a γδT cell population that is more homogeneous and has a higher effect than γδT cells separated from peripheral blood.

BRIEF DESCRIPTION OF DRAWINGS

FIG. 1B shows results of evaluation of the expression of CD3/γδTCR by flow cytometry for cells on day 31 of differentiation induction. (Example 1)

6

Figure 9:
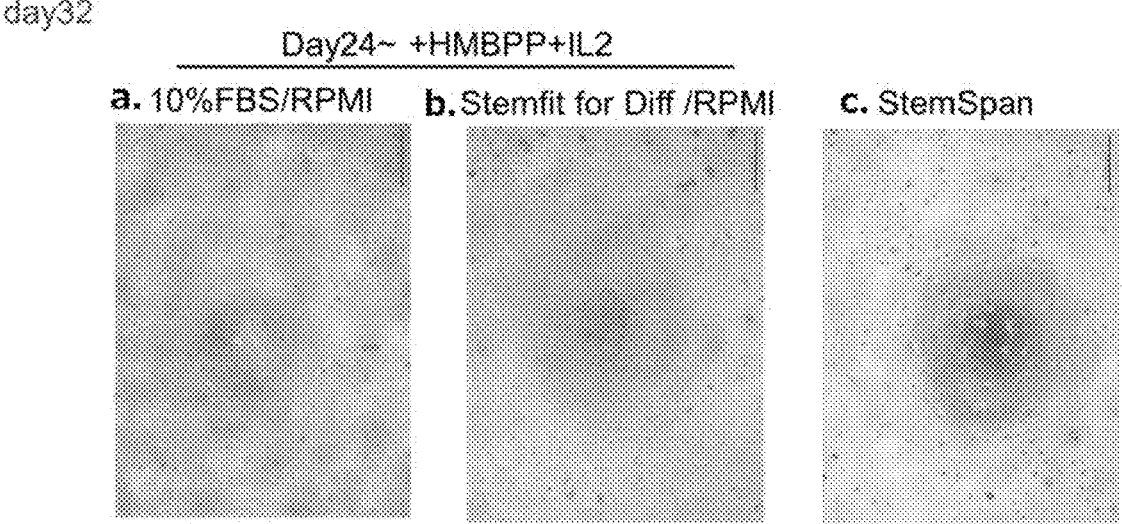

FIG. 9 shows results of observation of cells with a phase-contrast microscope for cells on day 32 of differentiation induction in the case where culture was performed in various media under a condition free from using feeder cells. (Example 6)

Figure 10:
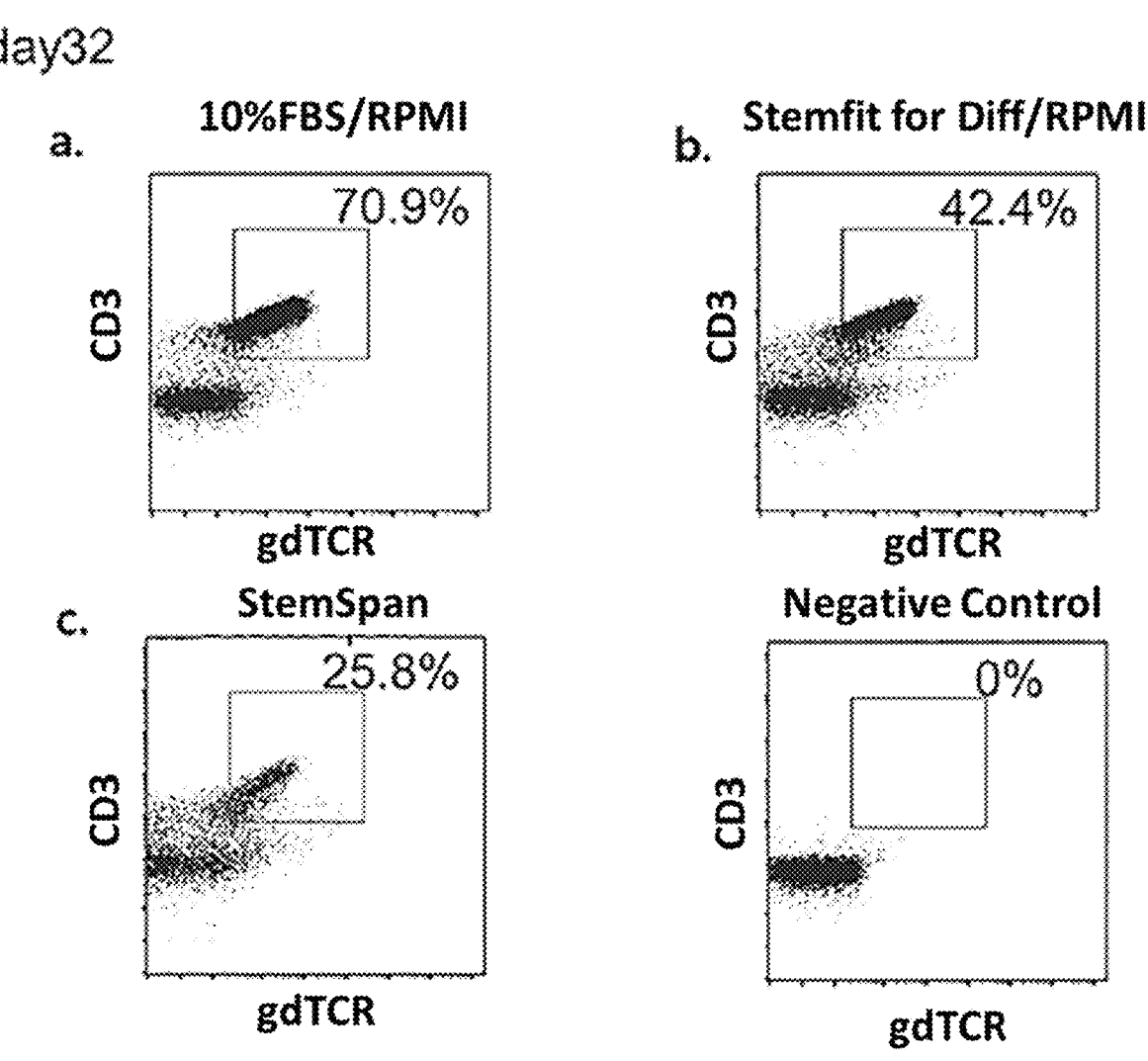

FIG. 10 shows results of evaluation of the expression of CD3/γδTCR by flow cytometry for cells on day 32 of differentiation induction in the case where culture was performed in various media under a condition free from using feeder cells. (Example 6)

Figure 11:
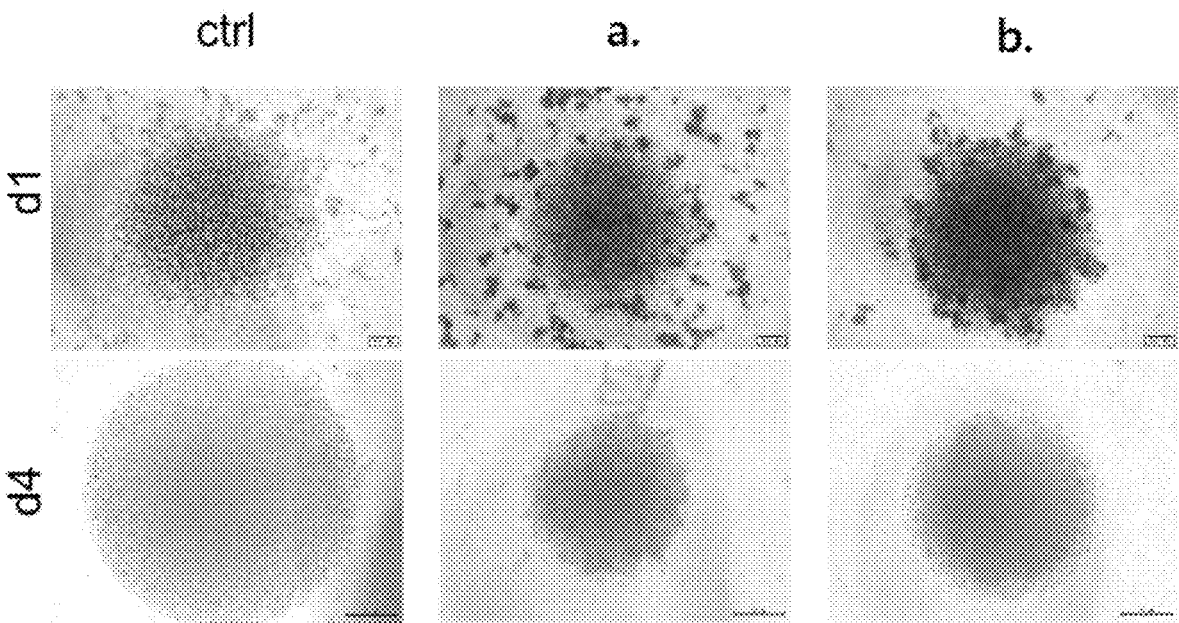

FIG. 11 shows that cells on day 35 of differentiation induction have cytotoxicity on Jurkat cells in the case where culture was performed in various media under a condition free from using feeder cells. (Example 6)

Figure 12:
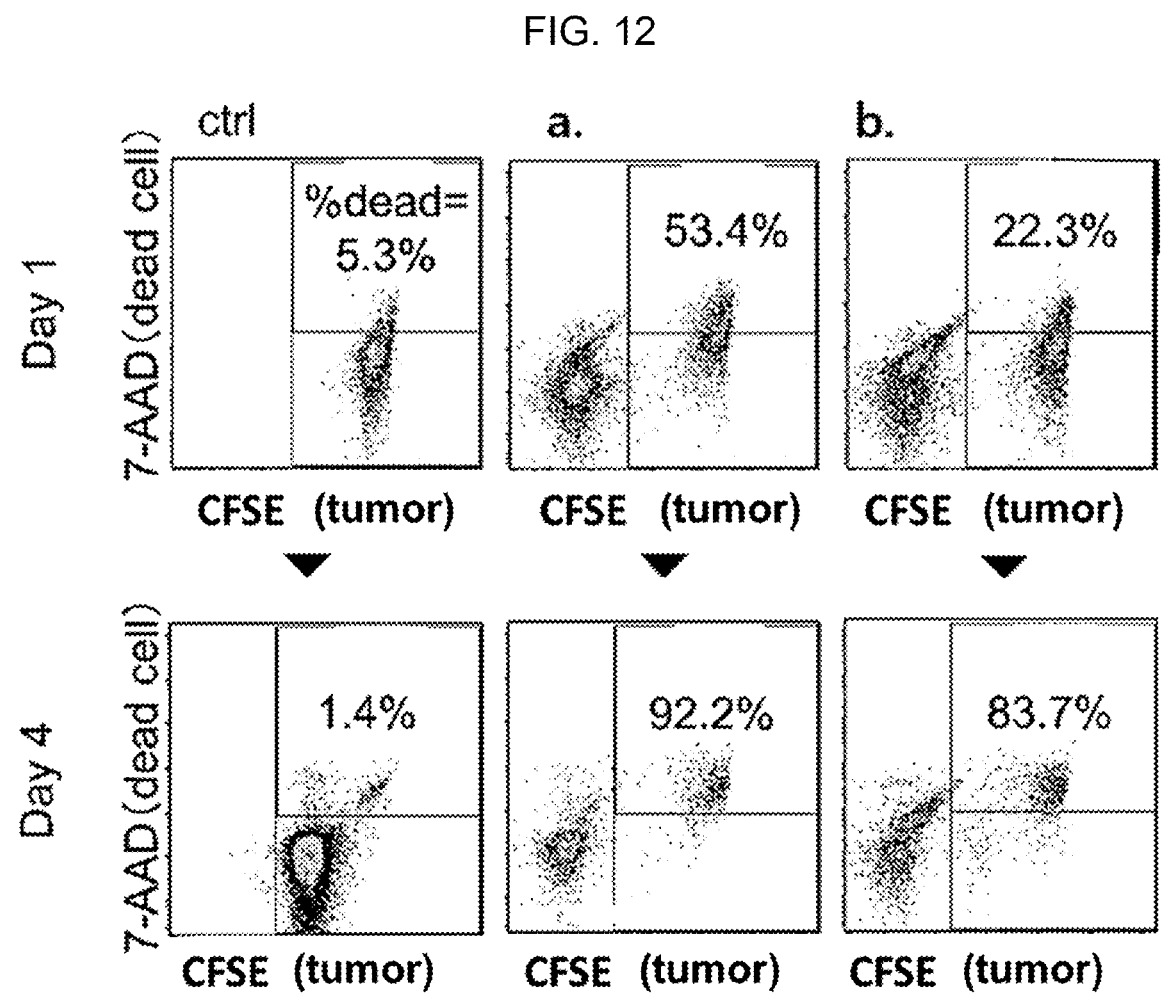

FIG. 12 shows results of determination of cytotoxic activity after 1 day and after 4 days from the initiation of mixed culture with Jurkat cells for cells on day 35 of differentiation induction in the case where culture was performed in various media under a condition free from using feeder cells. (Example 6)

Figure 13:
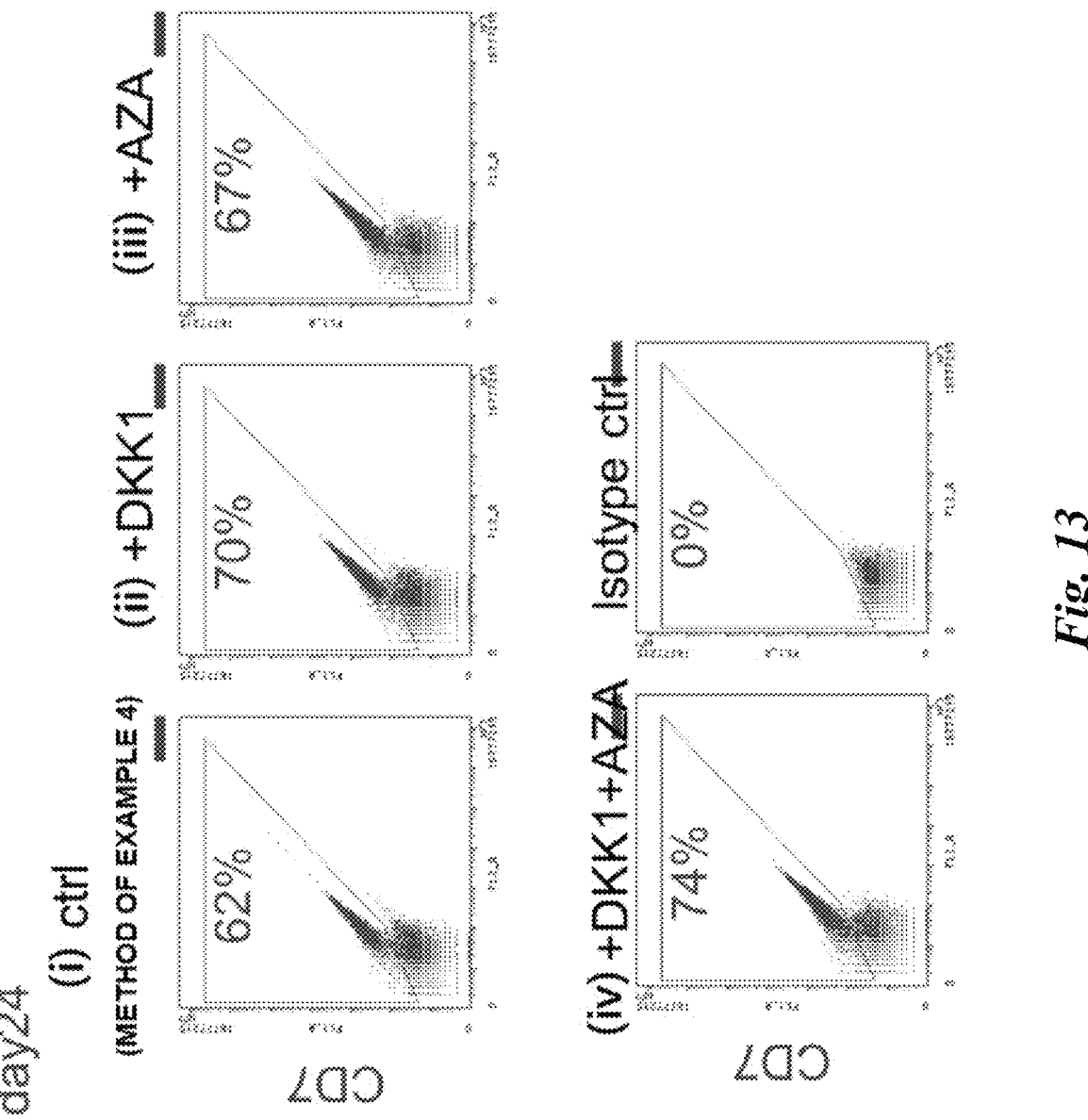

FIG. 13 shows results of evaluation of the expression of CD7 serving as a T cell differentiation marker by flow cytometry for cells on day 24 of differentiation induction under a condition free from using feeder cells. (Example 7)

FIG. 14 shows results obtained by performing differentiation induction into T cells through mixed culture with magnetic beads coated with VCAM1 and DLL4 instead of coating a culture dish under a condition free from using feeder cells, and evaluating the expression of CD7 serving as a T cell differentiation marker by flow cytometry for cells on day 24 of differentiation induction. (Example 8)

FIGS. 15A and 15B are illustrations of a protocol for differentiation induction of γδT cells generated in Example 9 from iPS cells. (Example 9)

Figure 16A:
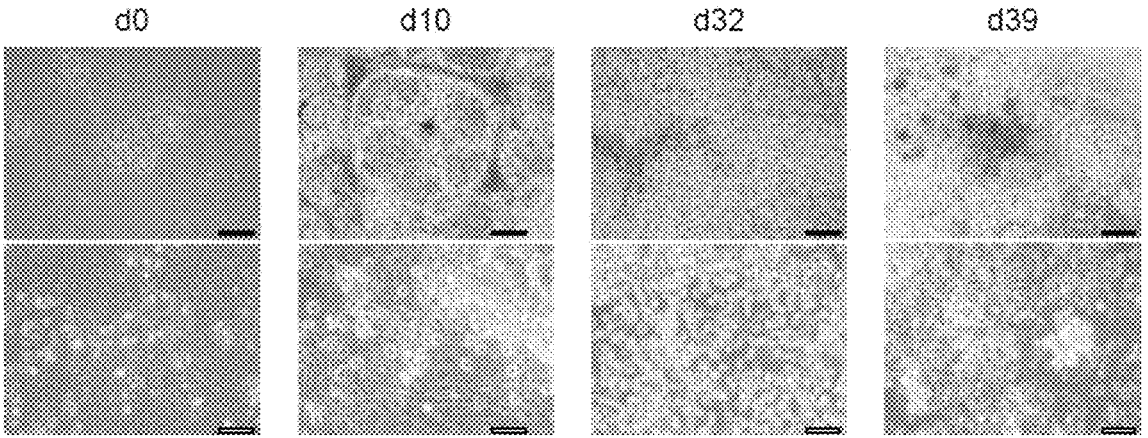
Figure 16B:
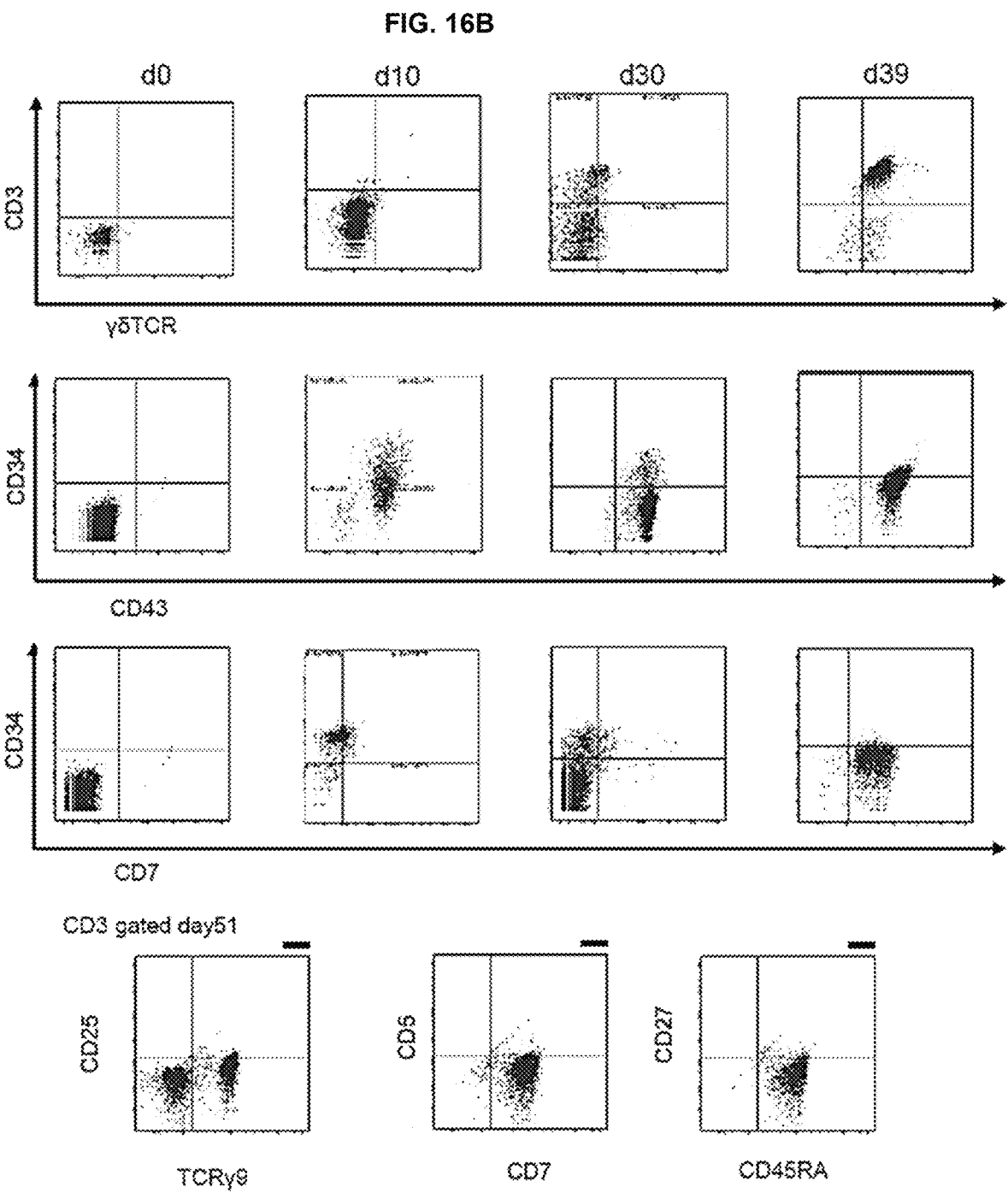

FIG. 16A shows results of observation of the morphology of cells in the process of differentiation with a phase-contrast microscope. FIG. 16B shows results of determination of cell surface markers by flow cytometry for cells in the process of differentiation. (Example 9)

Figure 17A:
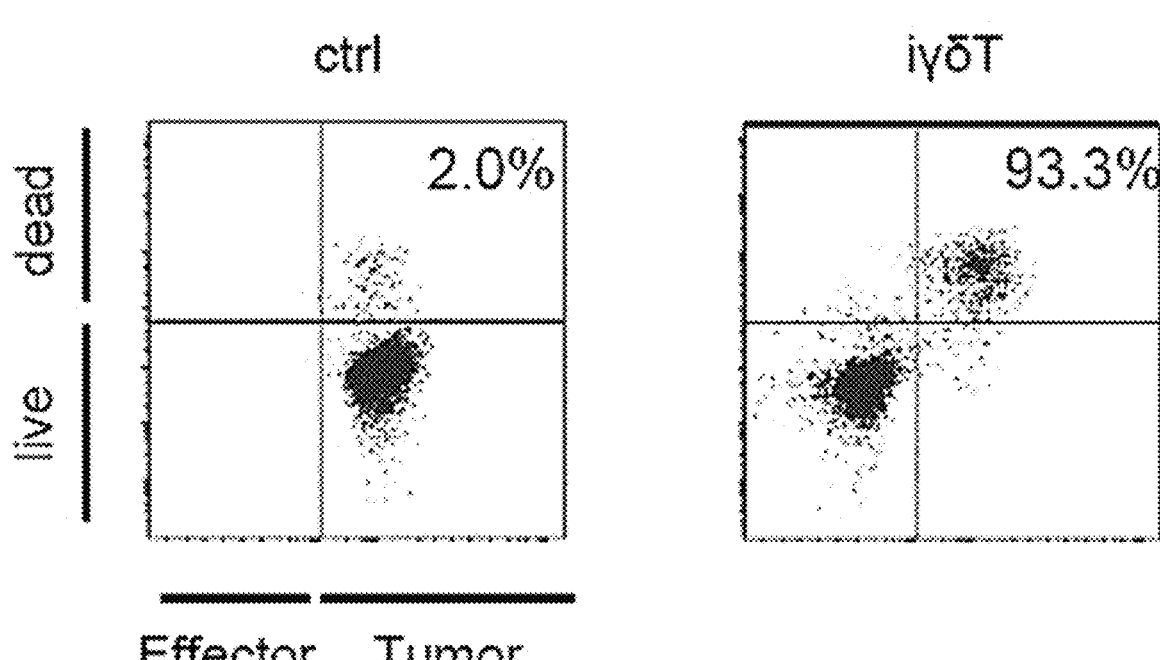
Figure 17C:
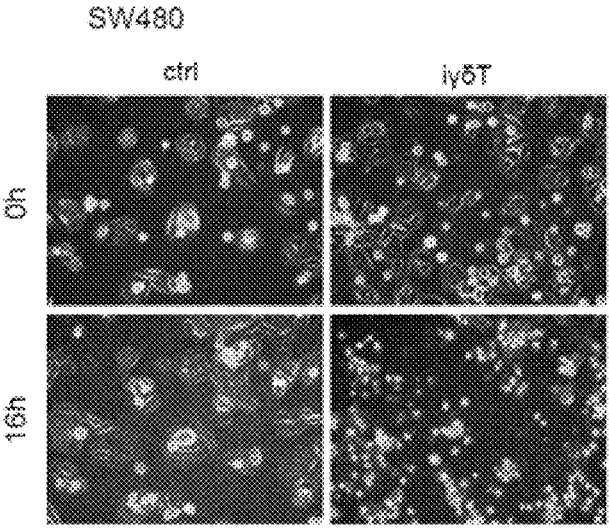
Figure 17D:
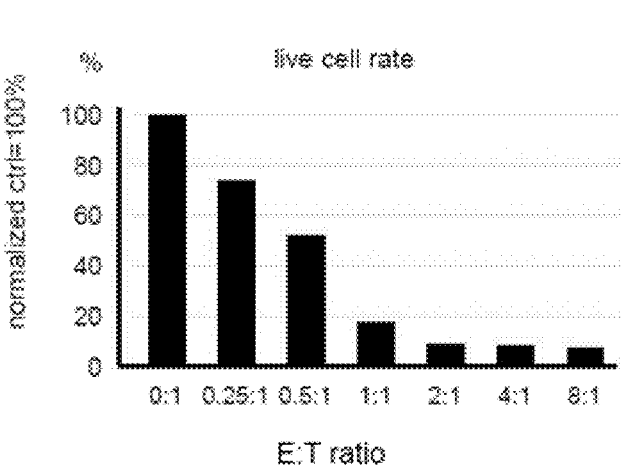

FIGS. 17A to 17D show results of determination of antitumor activity on various tumor cells for γδT cells on day 38 of differentiation induction. FIG. 17A shows results of determination of cytotoxic activity on Jurkat cells. FIG. 17B shows results of determination of cytotoxic activity on Huh-7 cells. FIG. 17C shows results of determination of cytotoxic activity on SW480 cells. FIG. 17D shows live cell rates in the case where an E:T ratio was gradually changed in mixed culture of iPS cell-derived γδT cells (E) and Jurkat cells (T). (Example 9)

Figure 18A:
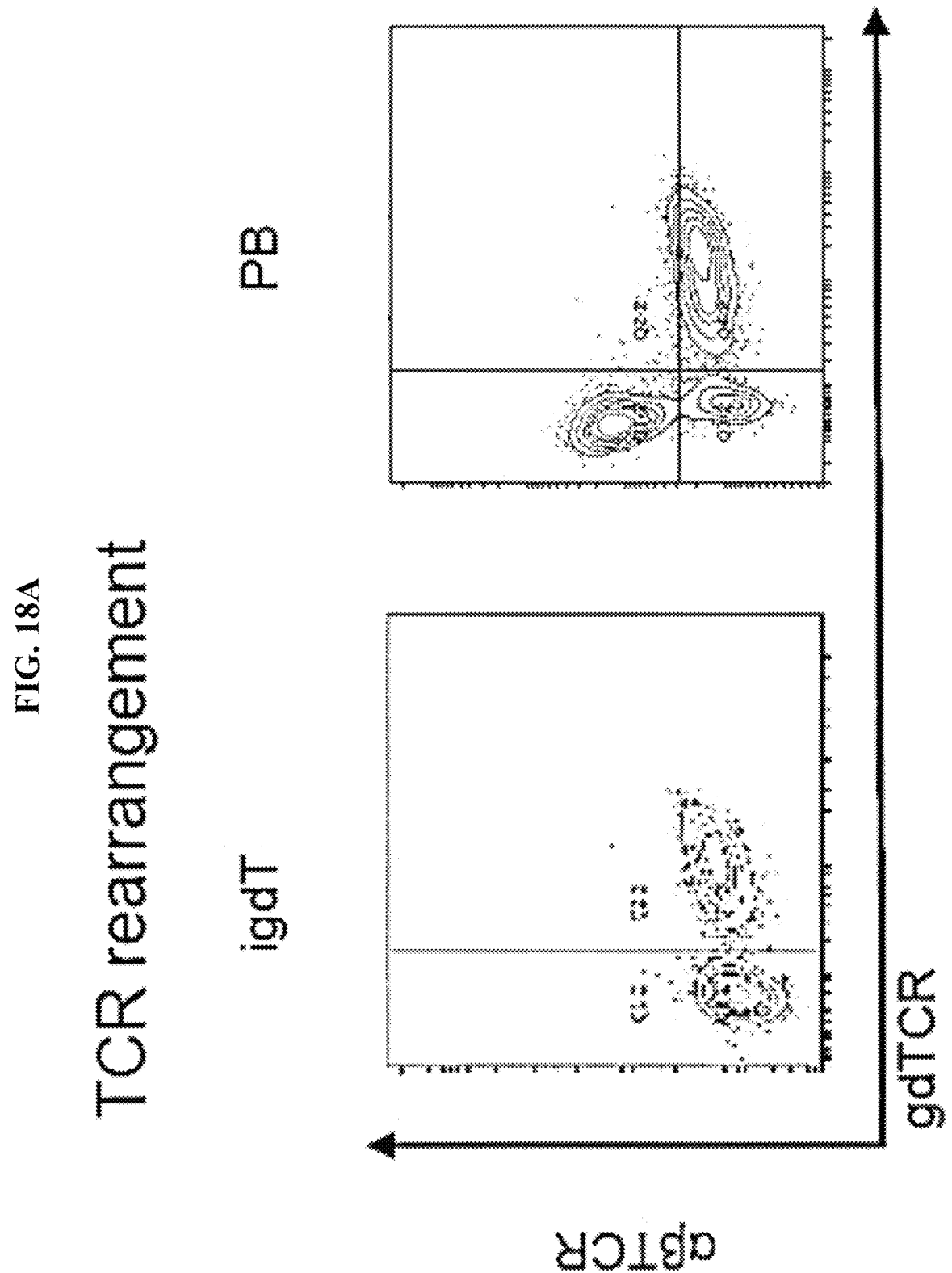
Figure 18B:
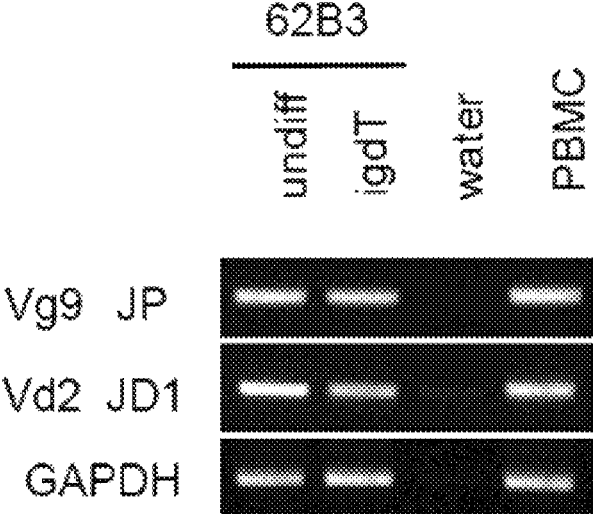
Figure 18C:
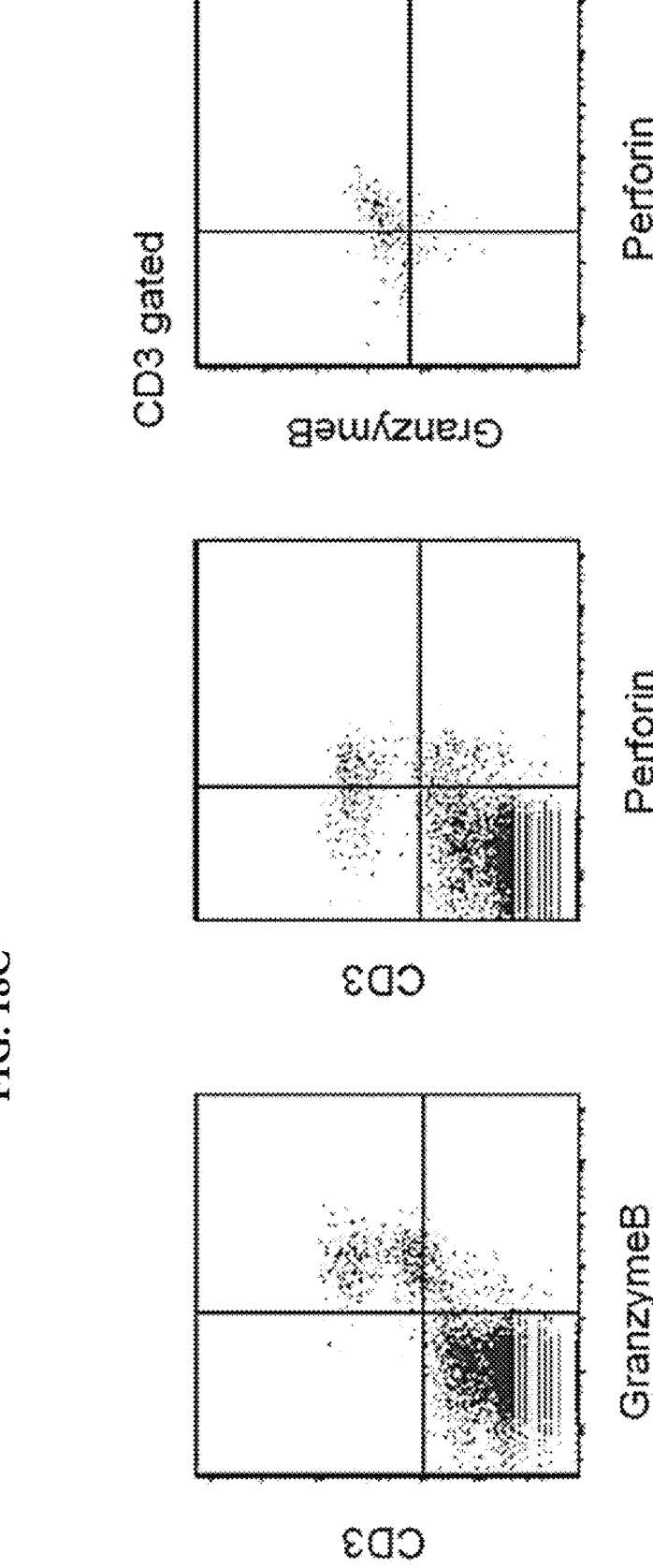
Figure 18D:
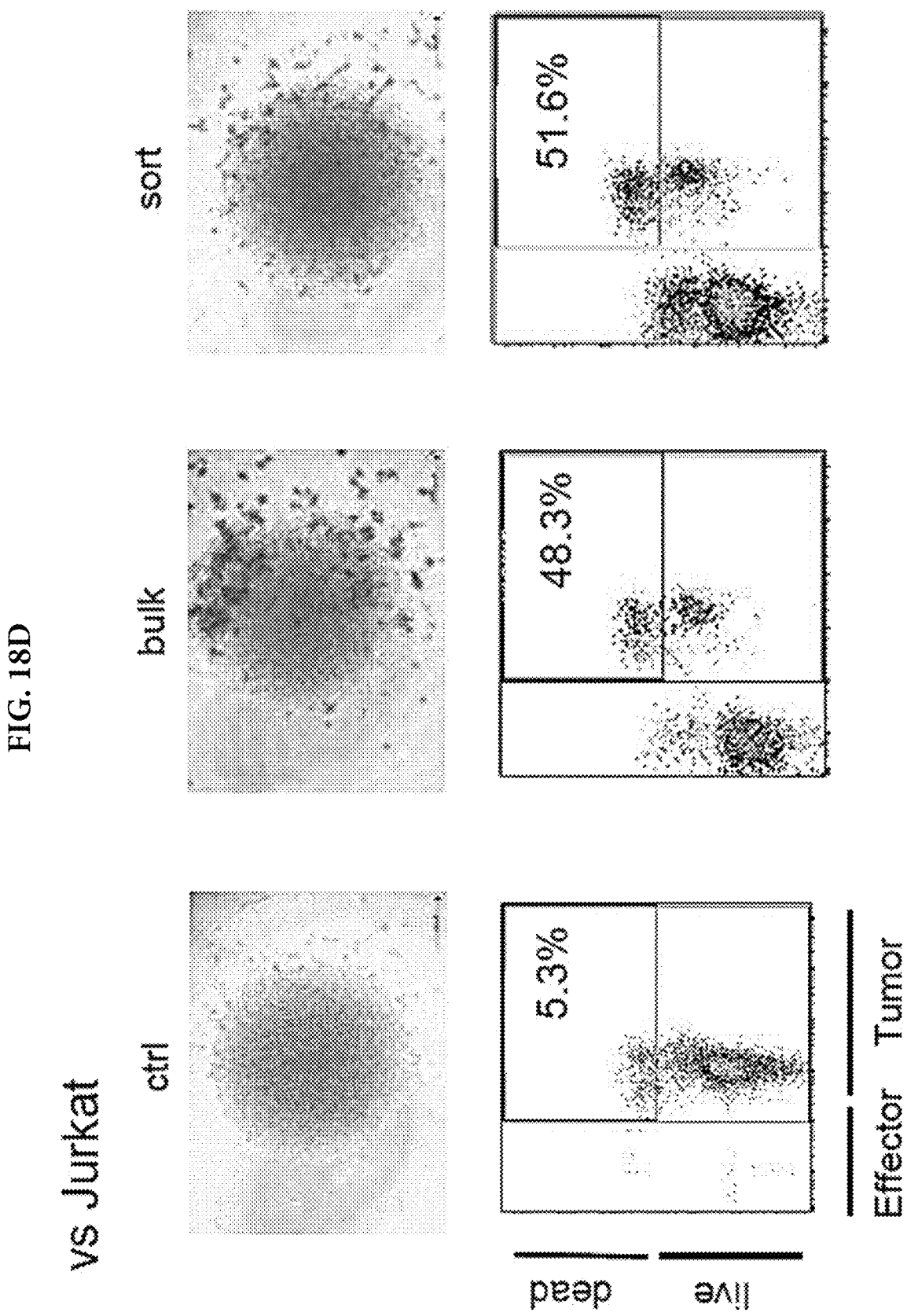

FIGS. 18A to 18D show results of determination of the retention of TCR rearrangement and a cytotoxic mechanism for γδT cells on day 36 of differentiation induction. FIG. 18A shows results of evaluation of the expression of αβTCR on cell surfaces for unpurified γδT cells (igdT) and peripheral blood mononuclear cells (PB). FIG. 18B shows results of determination of the rearrangement of TCR genes (Vγ9 and Vδ2) by genomic PCR. FIG. 18C shows results of determination of the expression of granzyme B and perforin in γδT cells. FIG. 18D shows results of determination of cytotoxic activity for purified γδT cells (igdT). Whether or not the γδT cells were purified did not make a large difference in dead cell rate. (Example 9)

Figure 19:
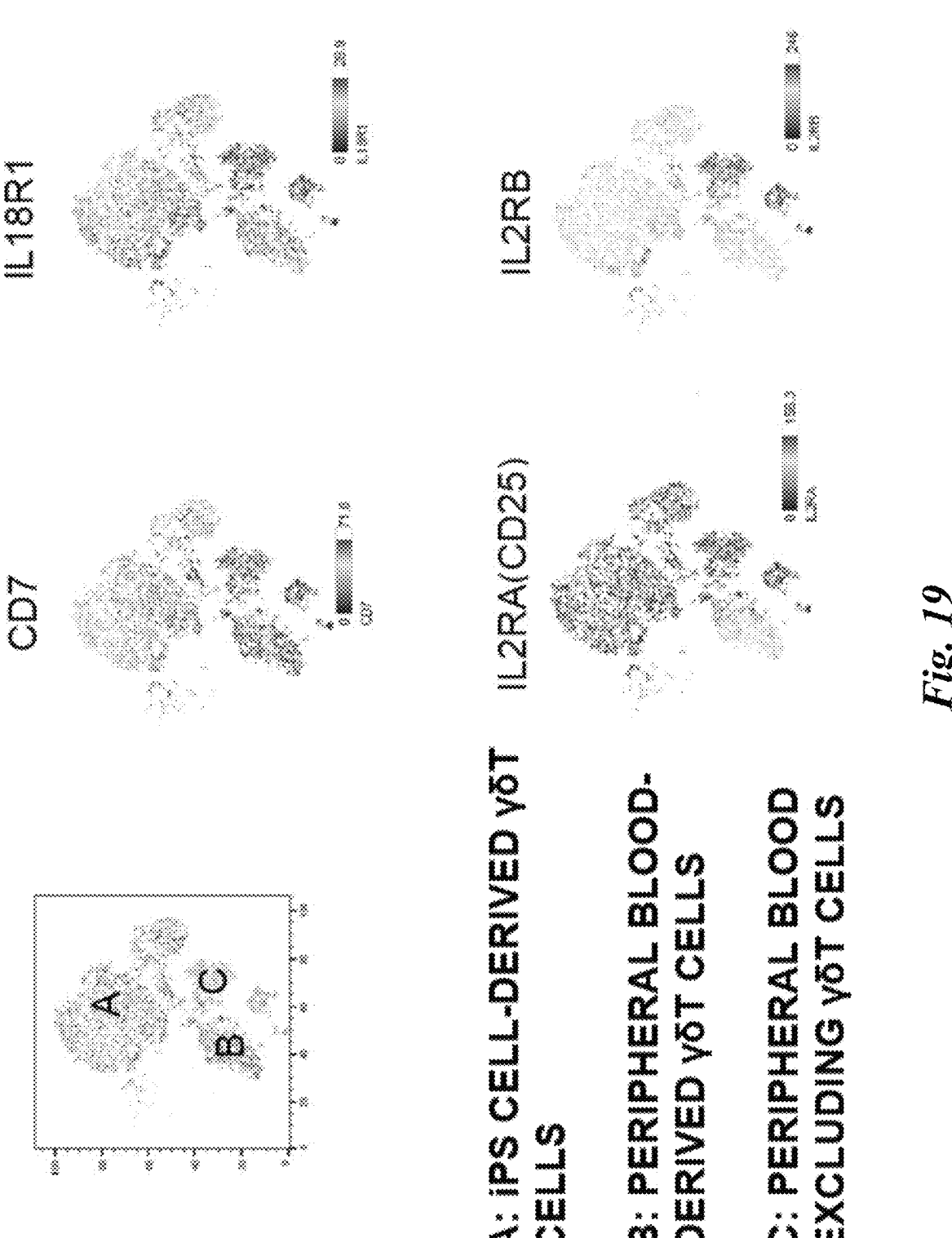

FIG. 19 shows results of determination of gene expression patterns in iPS cell-derived γδT cells and γδT cells separated from peripheral blood by single-cell RNA-seq analysis. (Example 10)

FIG. 20 shows results of analysis of CD25 among cell surface expression markers in iPS cell-derived γδT cells and γδT cells separated from peripheral blood by flow cytometry. (Example 10)

Figure 21:
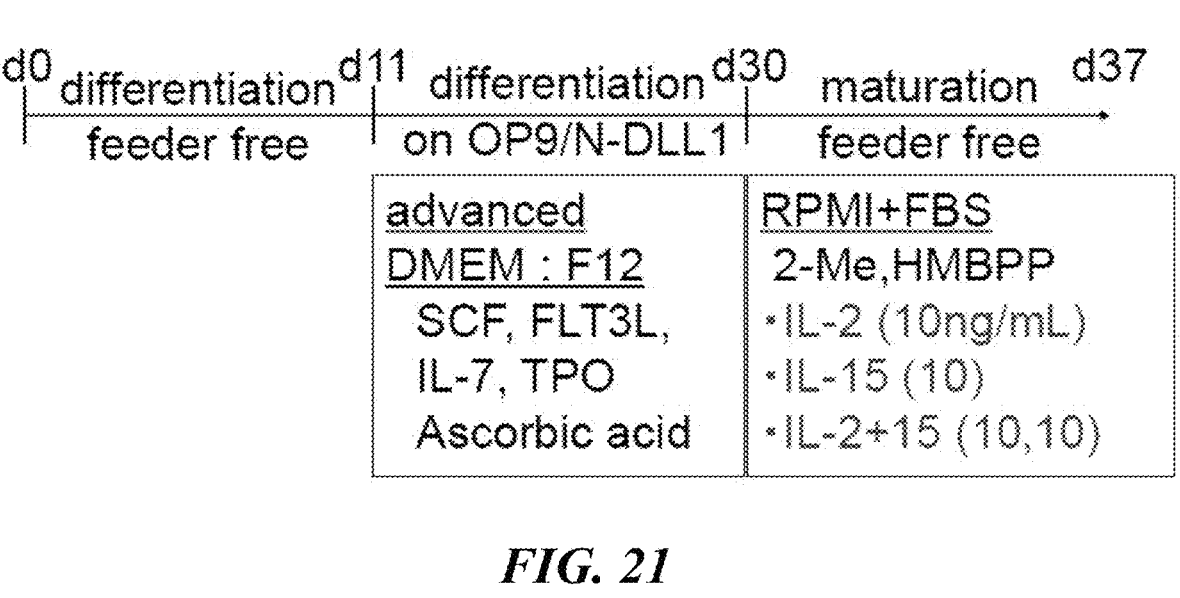

FIG. 21 is an illustration of a protocol for differentiation induction of γδT cells from iPS cells, for investigating a method of activating iPS cell-derived γδT cells. (Example 11)

Figure 22A:
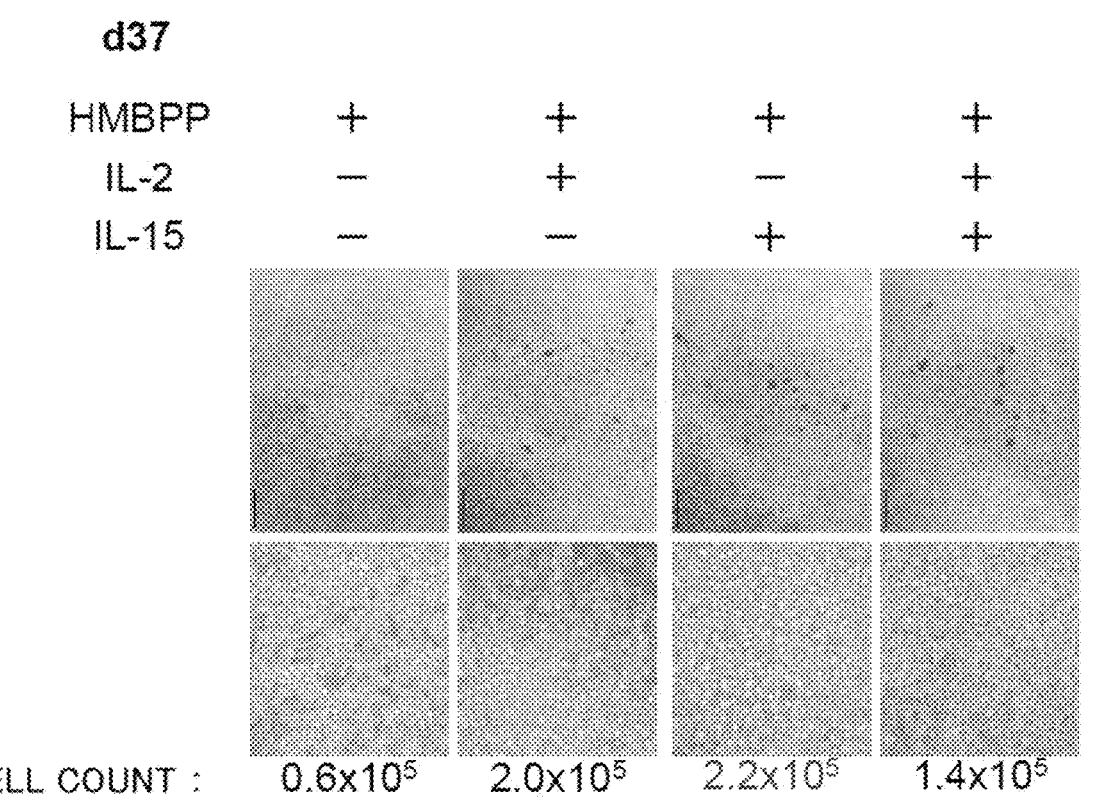
Figure 22B:
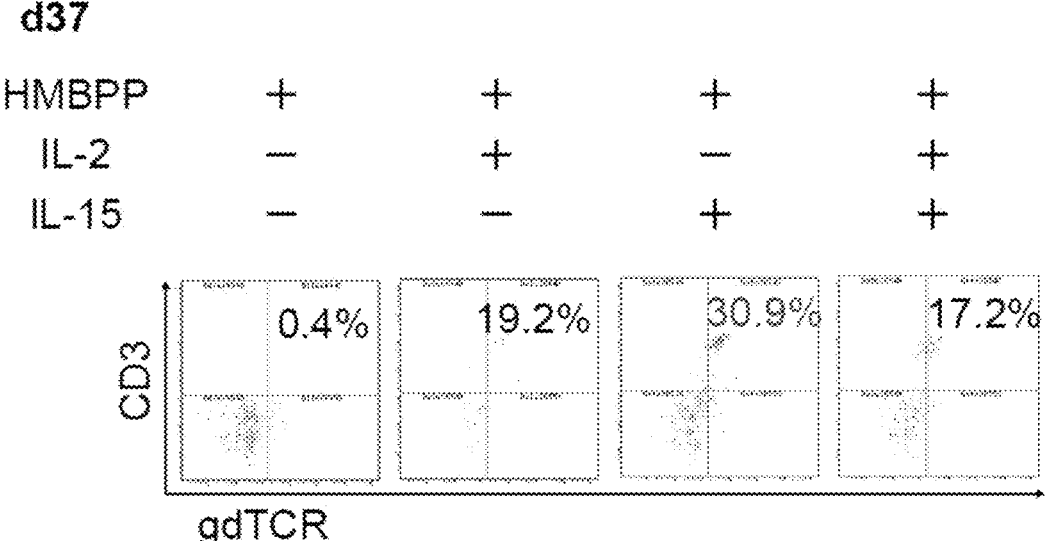

FIGS. 22A and 22B show results of an investigation about IL-2 and/or IL-15 in the method of activating iPS cell-derived γδT cells. FIG. 22A shows results of determination of live cell counts, and FIG. 22B shows results of evaluation of CD3⁺/γδTCR⁺ cells by flow cytometry. (Example 11)

Figure 23A:
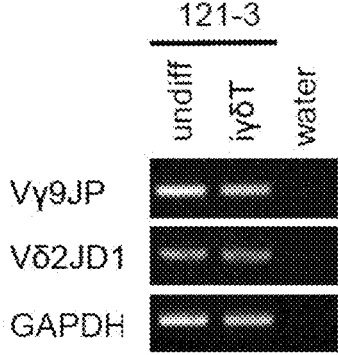
Figure 23B:
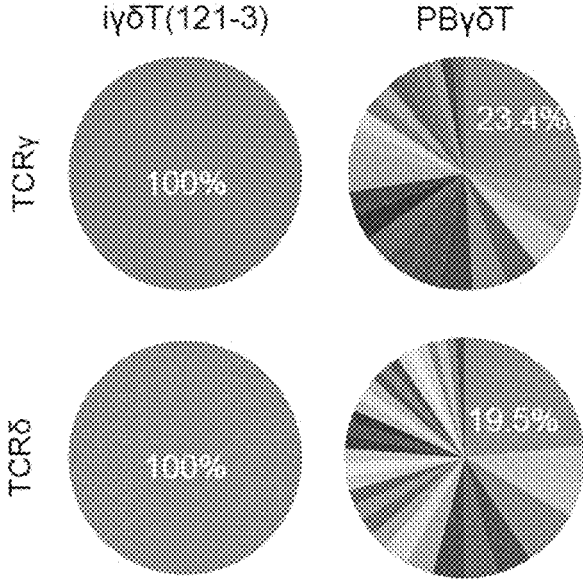

FIGS. 23A and 23B show results for γδT cells obtained by differentiation induction from a 121-3 line of γδT cell-derived iPS cells. FIG. 23A shows results of determination of the rearrangement of TCR genes (Vγ9 and Vγ2) of undifferentiated iPS cells (121-3 line) and γδT cells obtained by differentiation induction therefrom by genomic PCR. FIG. 23B shows results of determination of the sequences of TCRγs and TCRδs of the γδT cells and γδT cells obtained by subjecting peripheral blood mononuclear cells to expansion culture with a next-generation sequencer. (Example 12)

Figure 24:
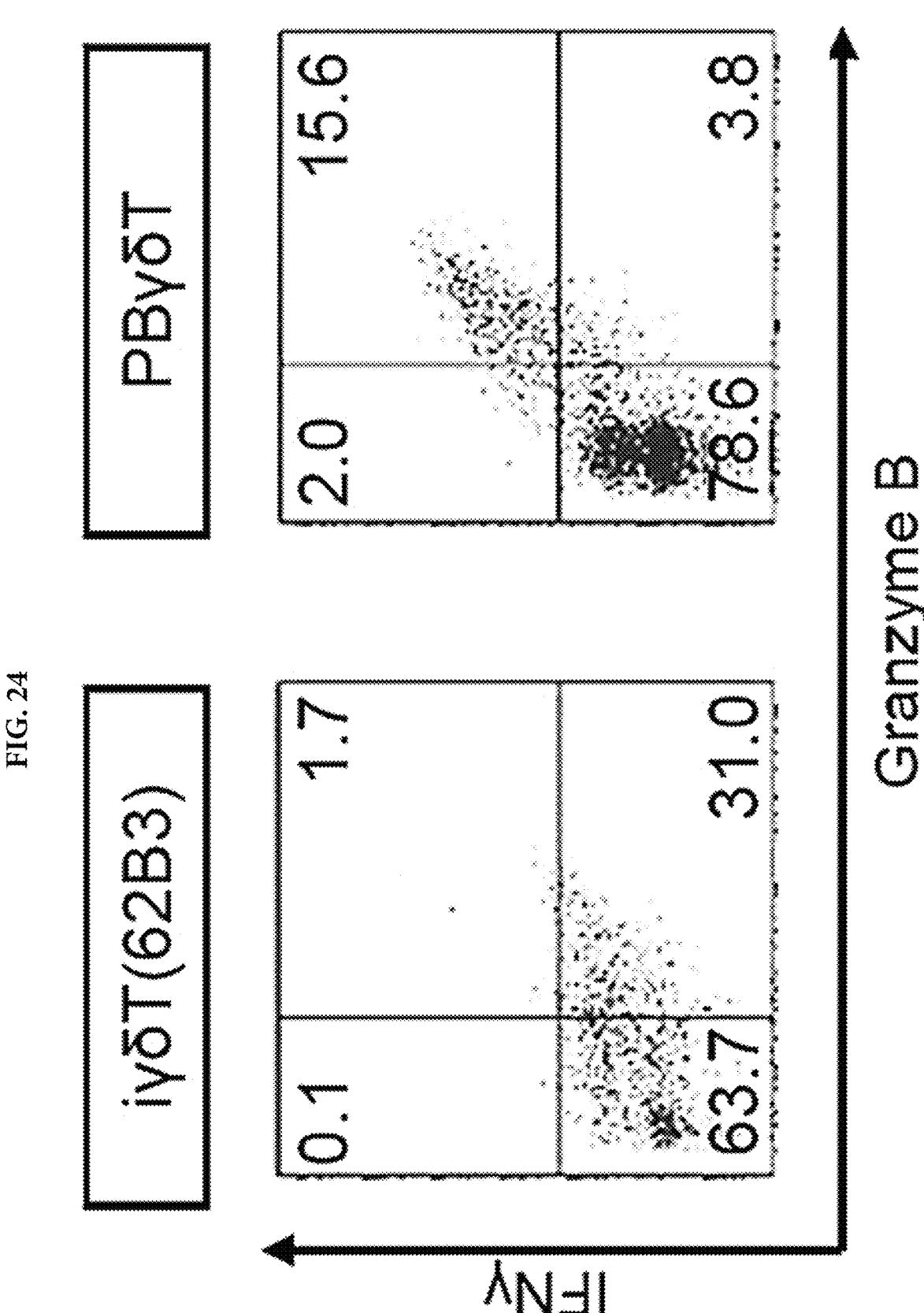

FIG. 24 shows results of evaluation by flow cytometry of the expression of IFNγ after iPS cell-derived γδT cells on day 39 of differentiation induction or γδT cells obtained by subjecting peripheral blood mononuclear cells to expansion culture were cocultured with Jurkat cells for 4 hours. (Example 13)

Figure 25:
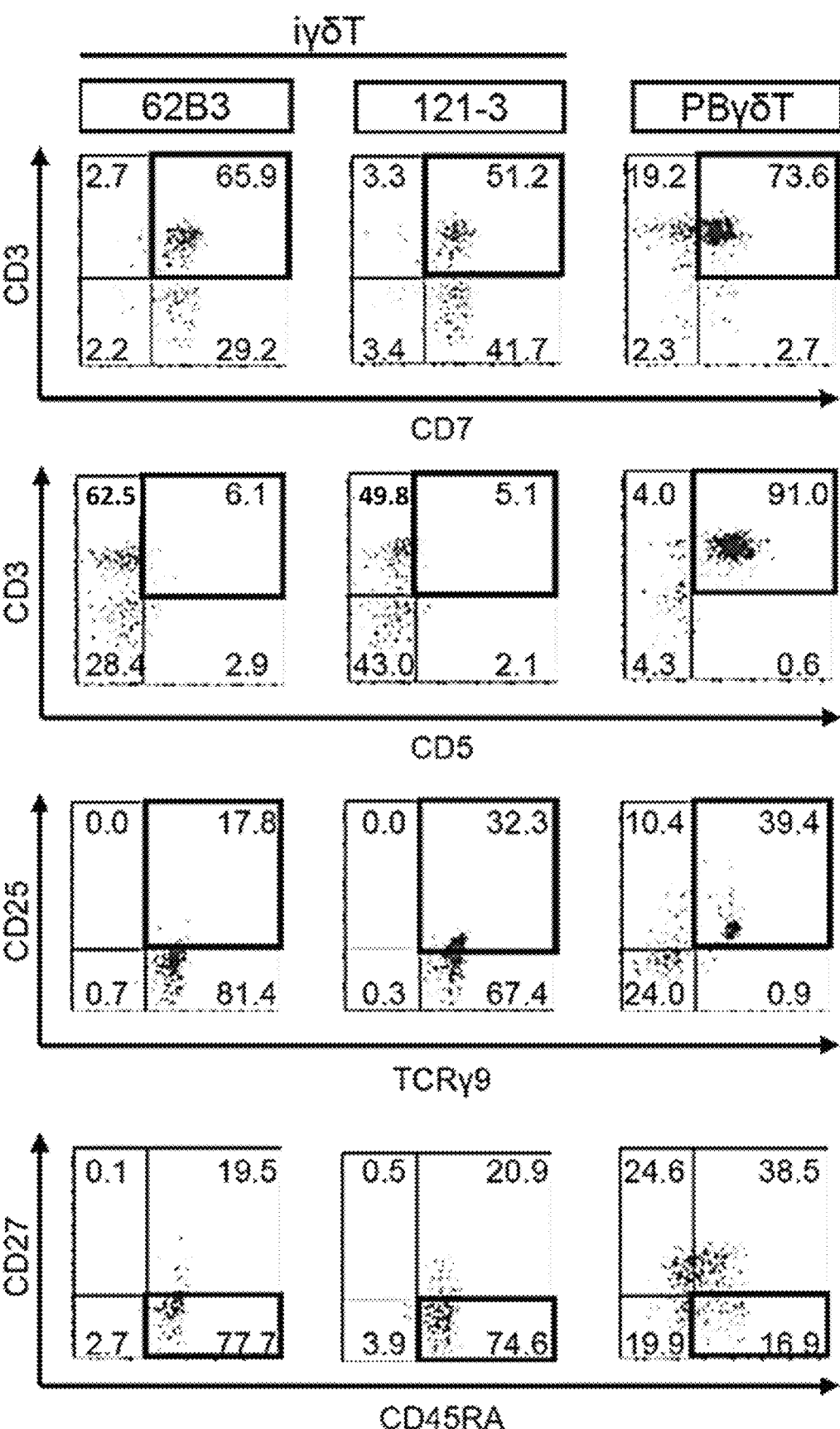

FIG. 25 shows results of evaluation by flow cytometry of the expression of various surface markers in a cell population including iPS cell-derived γδT cells on day 40 of differentiation induction obtained by differentiation induction performed by a method involving using feeder cells and a cell population (CD3-positive or TCRγ9-positive) including γδT cells obtained by subjecting peripheral blood mononuclear cells to expansion culture. (Example 14)

Figure 26A:
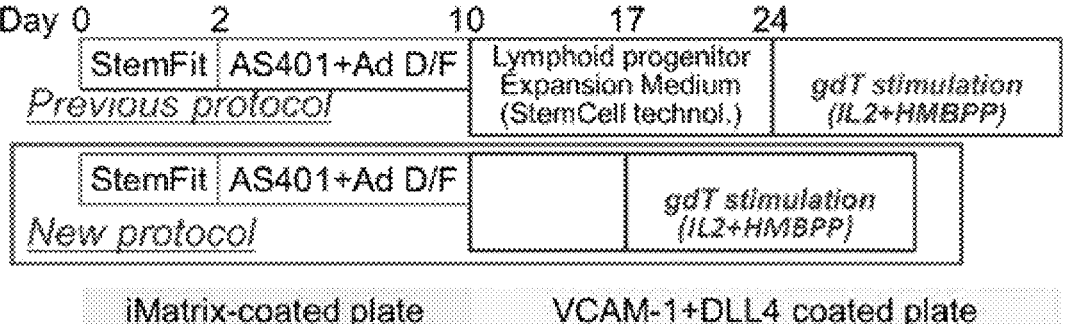
Figures 26B, 26C:
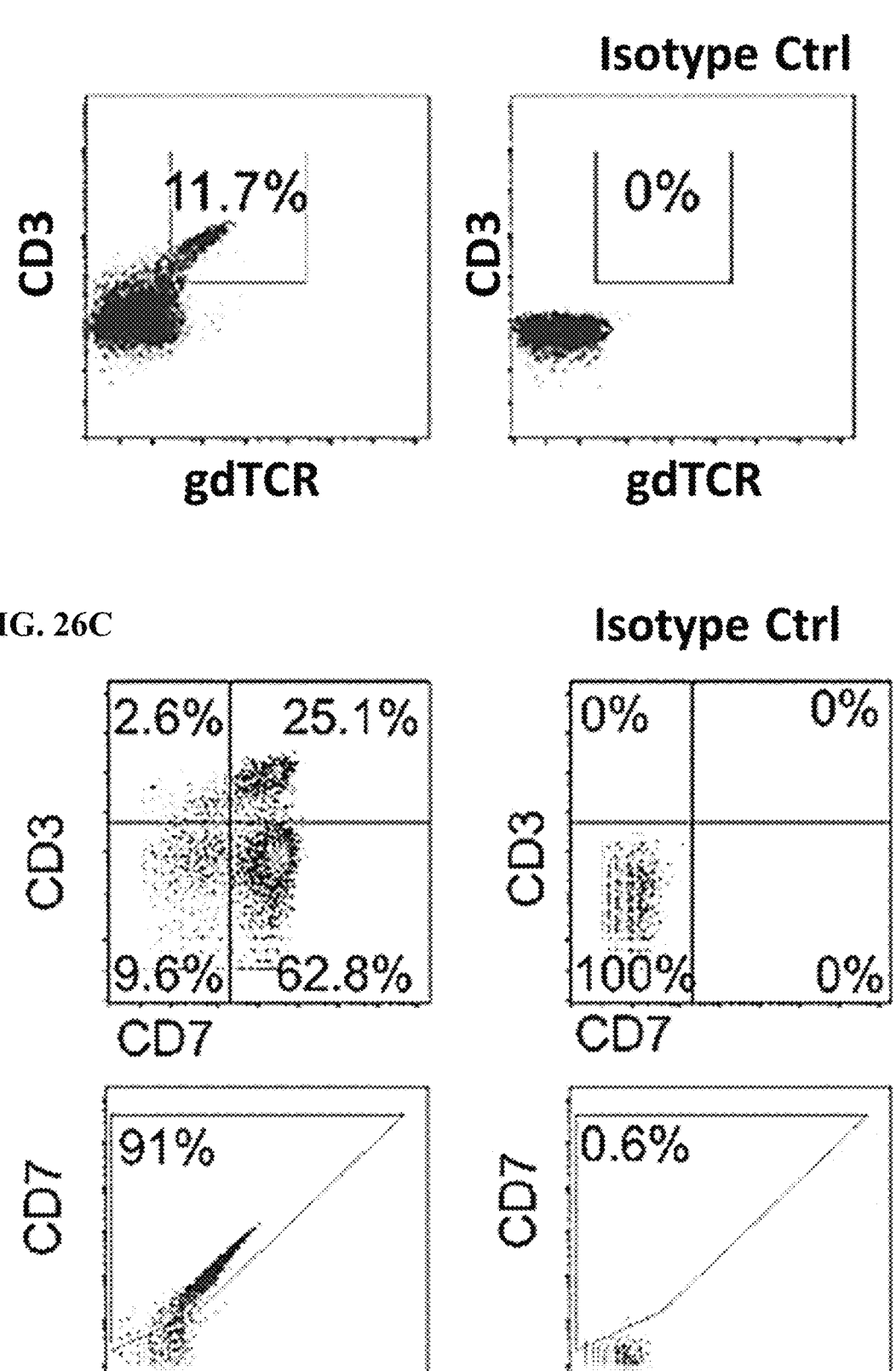

FIG. 26A is an illustration of a protocol involving performing a step of stimulating γδT cells from day 17. FIG. 26B shows results of evaluation of the expression of CD3/γδTCR by flow cytometry for cells on day 17 of differentiation induction. FIG. 26C shows results of evaluation of the expression of CD3/CD7 by flow cytometry for cells on day 24 of differentiation induction. (Example 15)

Figure 27A:
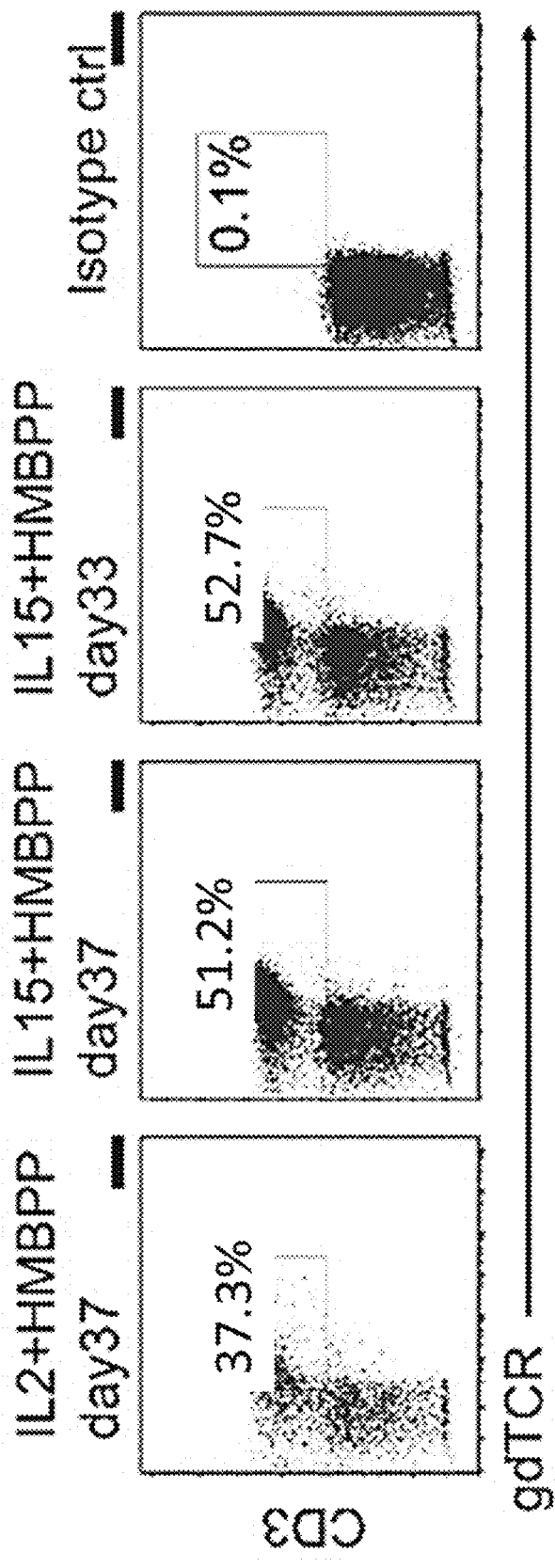
Figure 27B:
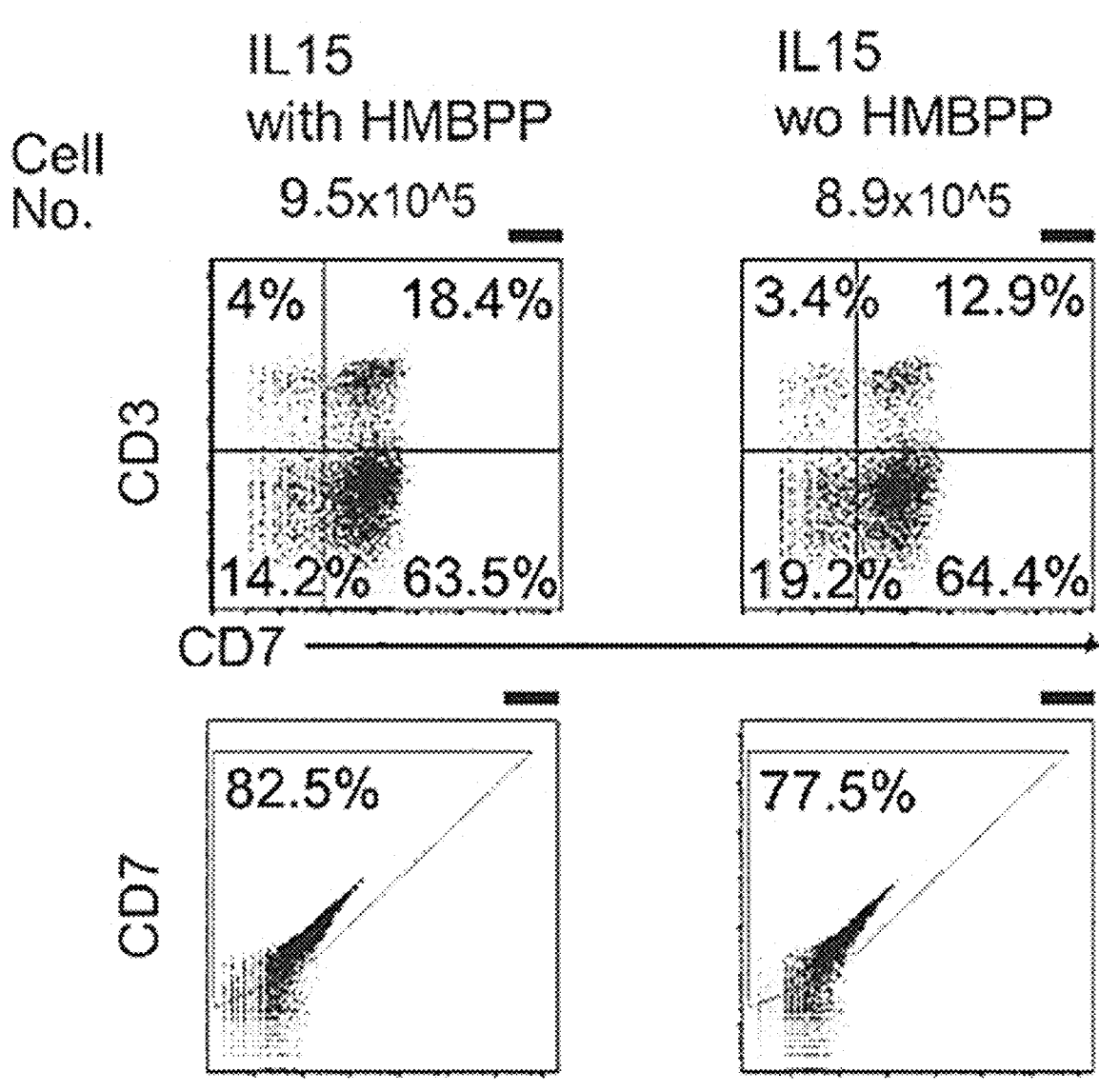

FIGS. 27A and 27B show results of an investigation about IL-2 or IL-15, or IL-15 or IL-15+HMBPP in a method of activating iPS cell-derived γδT cells. FIG. 27A shows results of evaluation of the expression of CD3/γδTCR by flow cytometry for cells on day 37 or day 33 of differentiation induction. FIG. 27B shows results of evaluation of the expression of CD3/CD7 by flow cytometry for cells on day 23 of differentiation induction. (Example 16)

FIG. 28 shows results of determination of cytotoxic activity on Jurkat cells after freezing and thawing of cells on day 24 of differentiation induction under a condition free from using feeder cells. (Example 17)

Figure 29A:
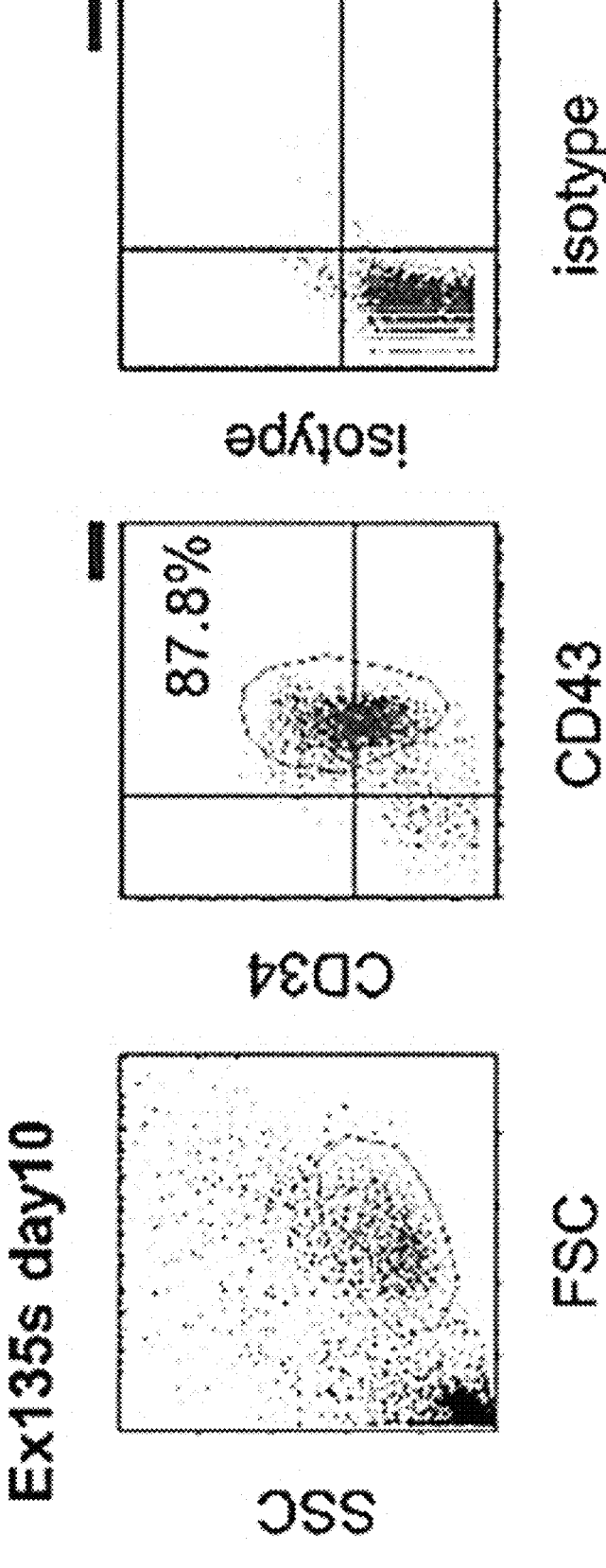
Figure 29B:
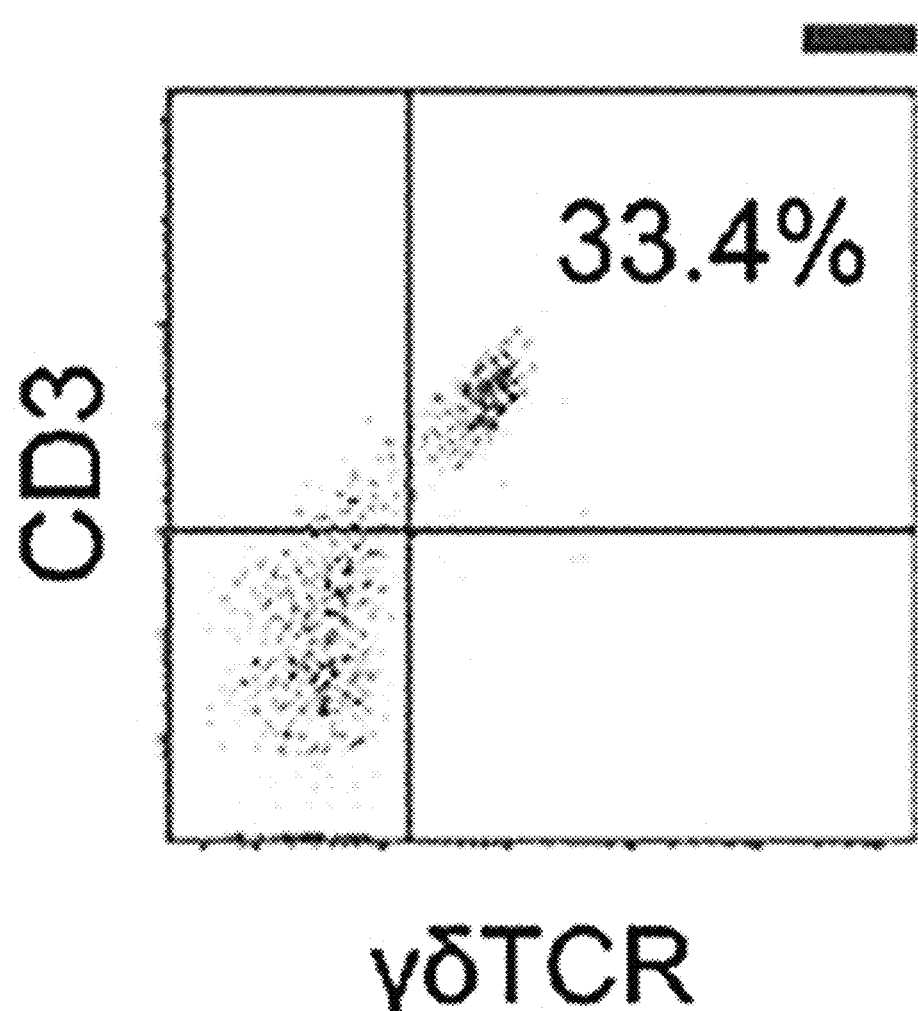
Figure 29C:
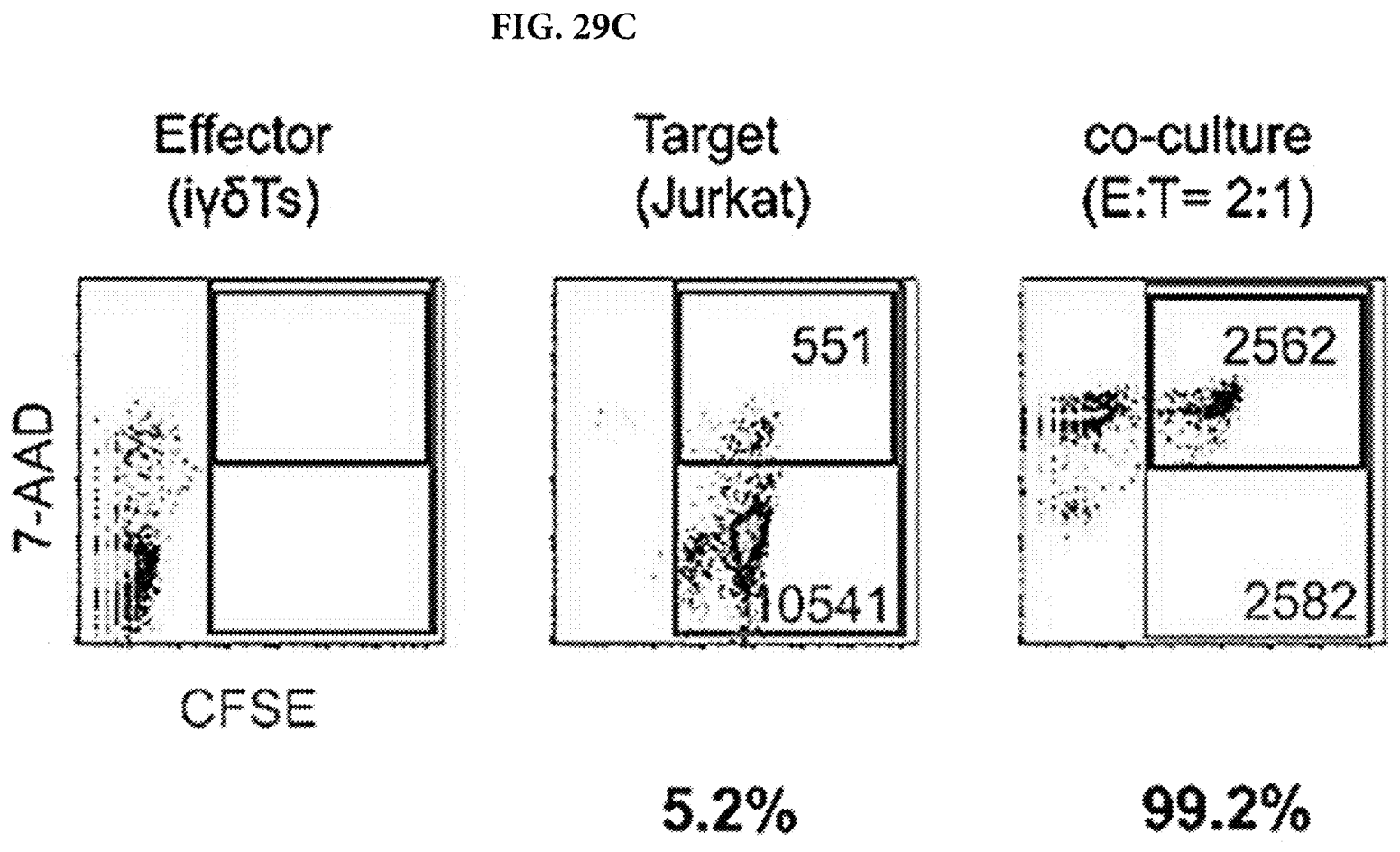

FIG. 29A shows results of evaluation of the expression of CD34/CD43 by flow cytometry for cells on day 10 of differentiation induction. FIG. 29B shows results obtained by further freezing and thawing the cells on day 10 of differentiation induction, and evaluating the expression of CD3/γδTCR by flow cytometry for cells on day 37 of differentiation induction. FIG. 29C shows results of determination of cytotoxic activity on Jurkat cells for the cells on day 37 of differentiation induction. (Example 18)

Figure 30A:
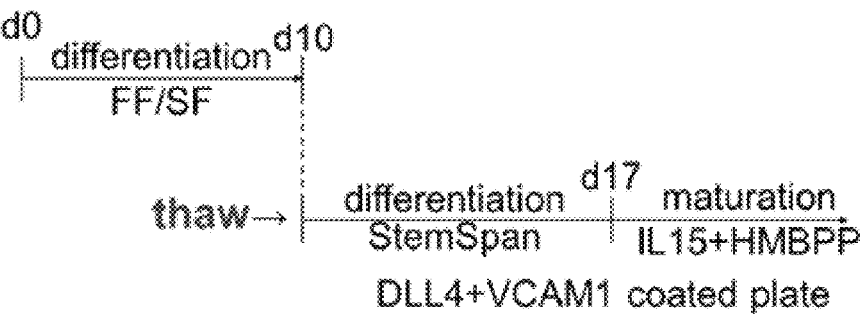
Figure 30B:
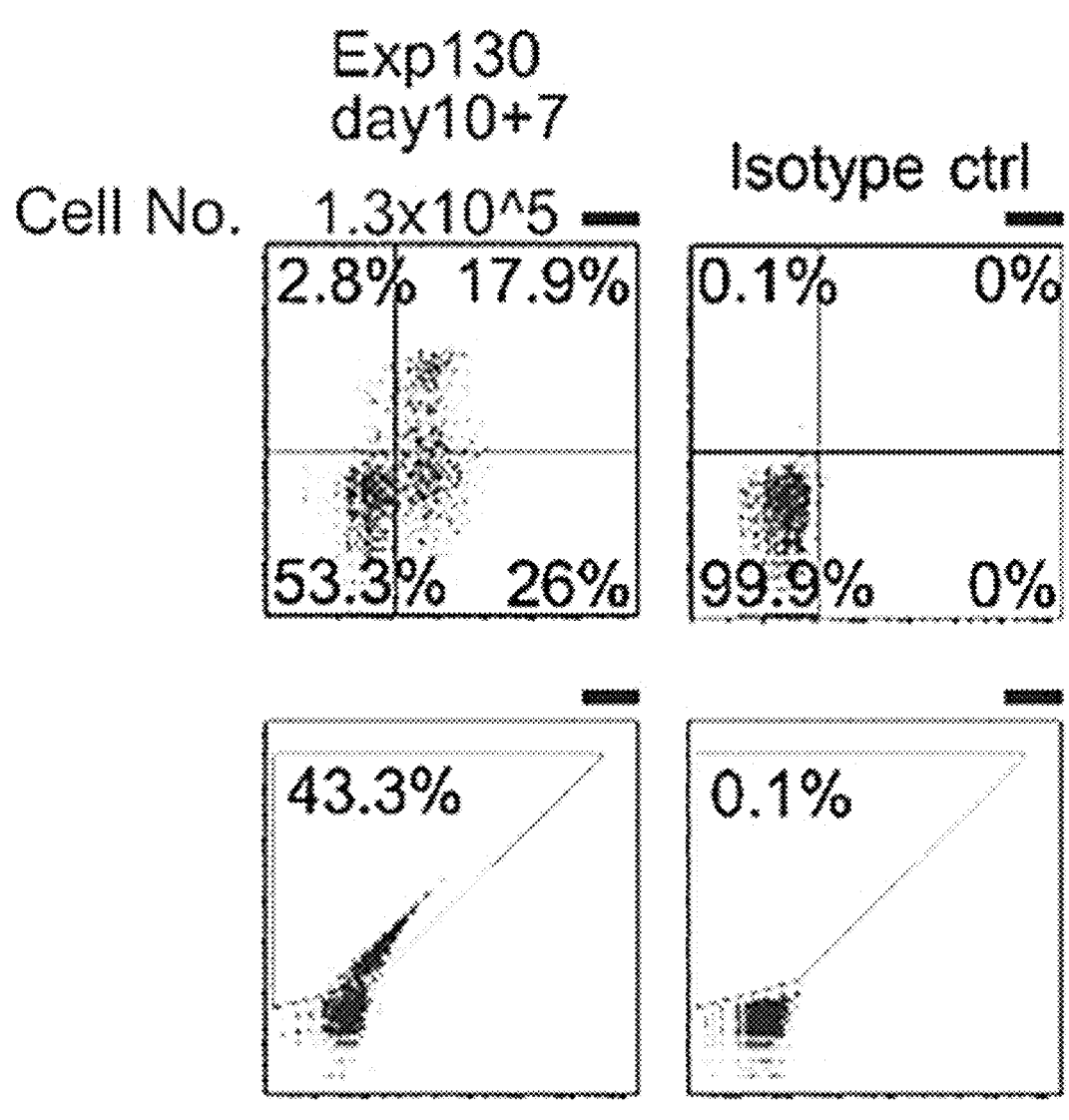
Figure 30C:
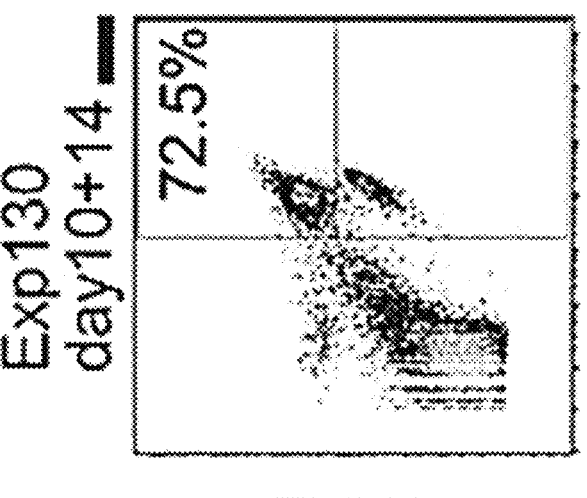

FIG. 30A is an illustration of a protocol in which iPS cell-derived hematopoietic progenitor cells are frozen and thawed, and then subjected to differentiation induction under a serum-free condition free from using feeder cells. FIG. 30B shows results of evaluation of the expression of CD3/γδTCR by flow cytometry for cells on day 17 of differentiation induction. FIG. 30C shows results of determination of cytotoxic activity on Jurkat cells for cells on day 24 of differentiation induction. (Example 19)

Figure 31A:
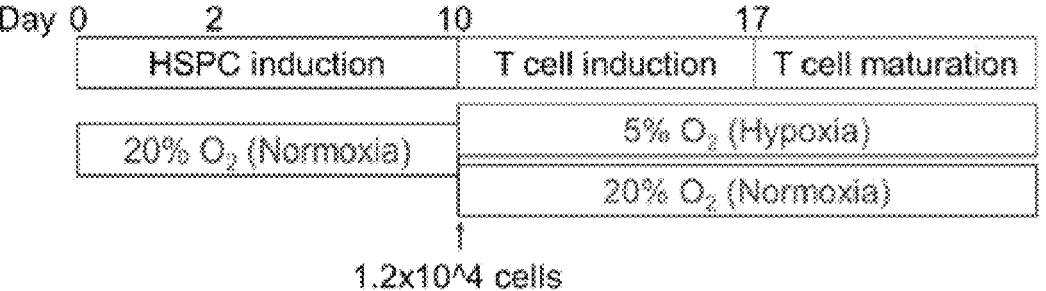
Figure 31B:
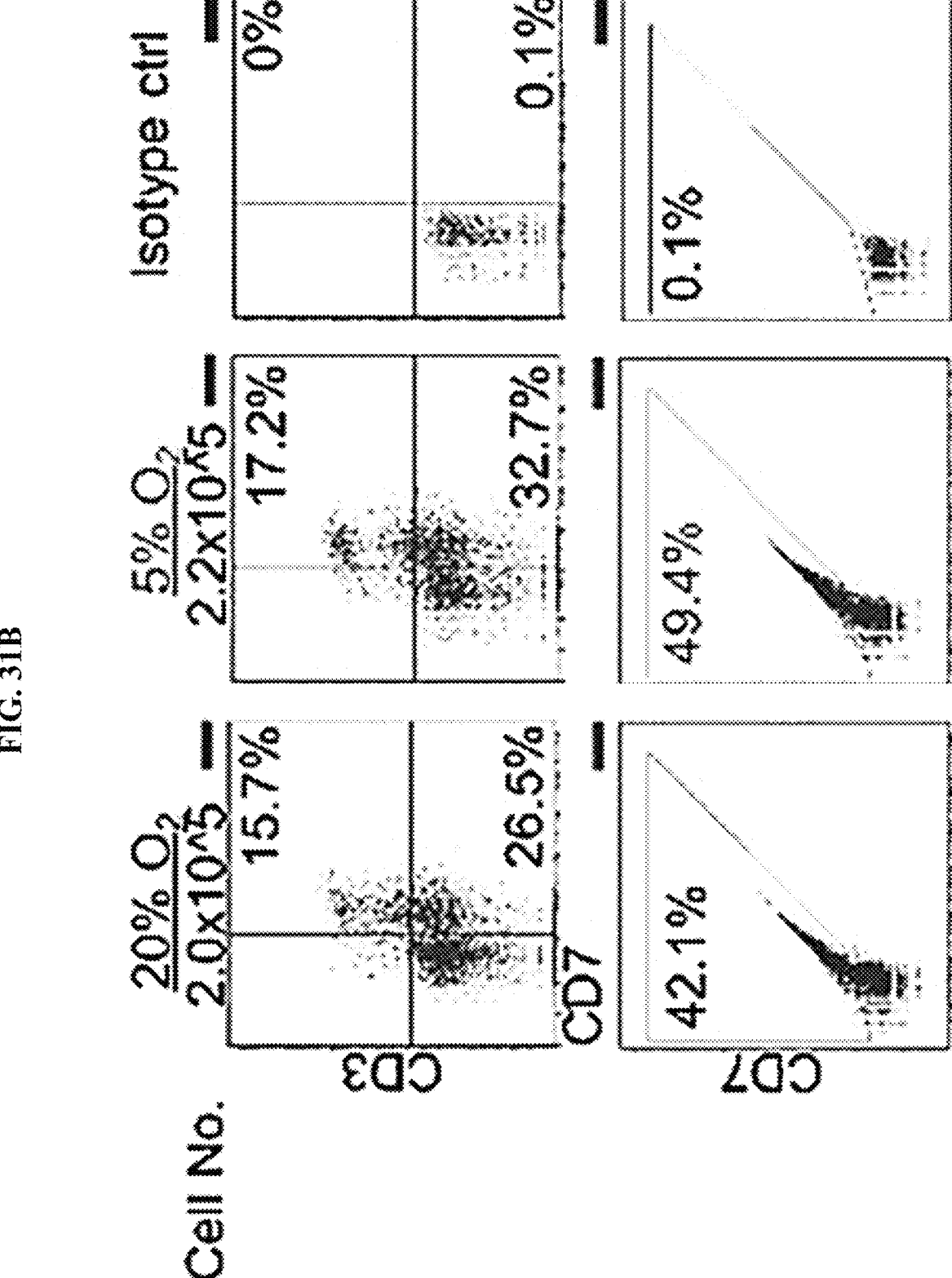
Figure 31C:

FIG. 31A is an illustration of a protocol for inducing differentiation of hematopoietic progenitor cells into γδT cells under a hypoxic condition. FIG. 31B shows results of evaluation of the expression of CD3/CD7 by flow cytometry for cells on day 17 of differentiation induction. FIG. 31C shows results of determination of cytotoxic activity on Jurkat cells for cells on day 29 of differentiation induction. (Example 20)

Figure 32A:
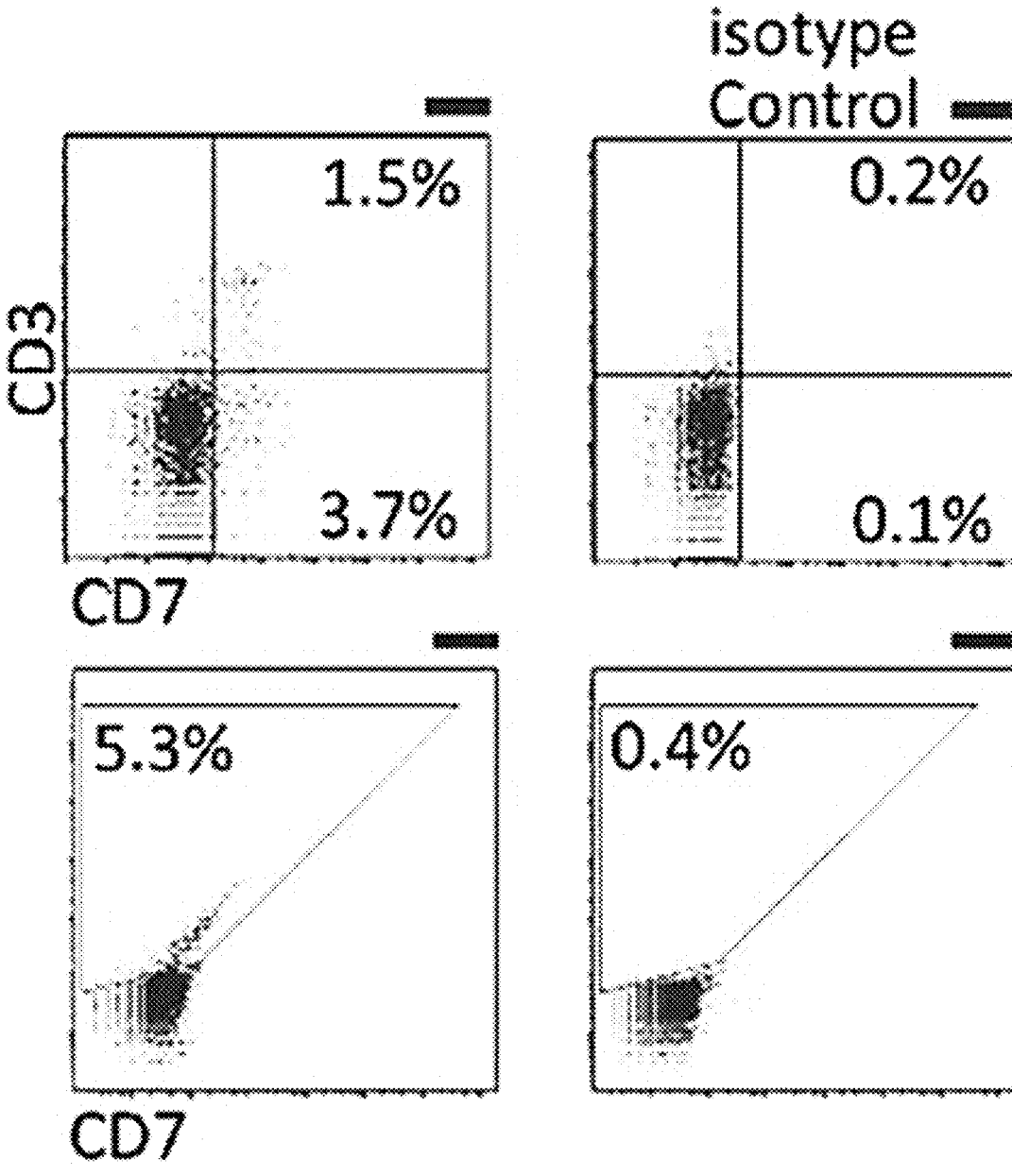
Figure 32B:
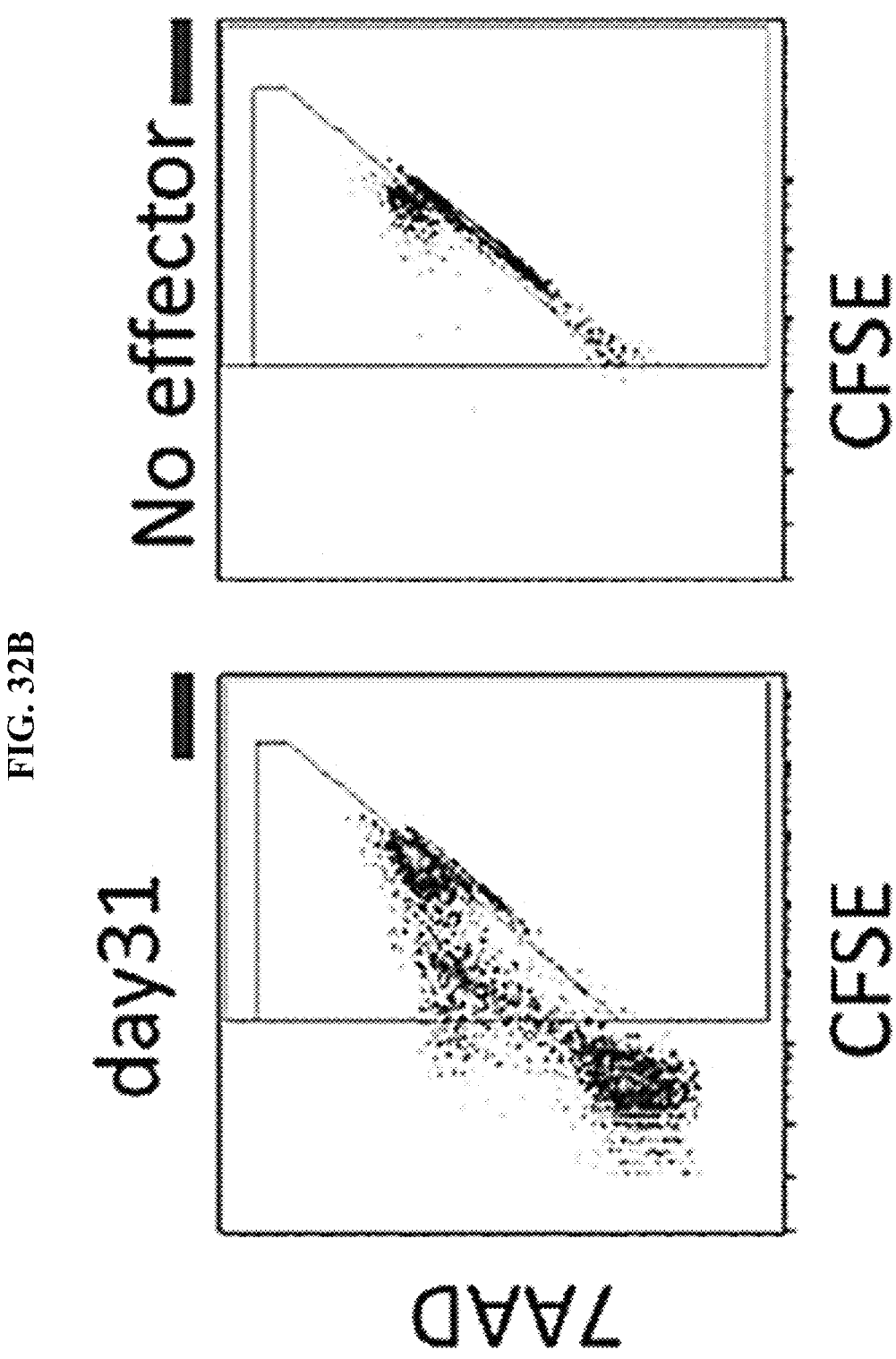

FIGS. 32A and 32B show that iPS cell-derived γδT cells were induced to differentiate under an animal-derived component-free condition. FIG. 32A shows results of evaluation of the expression of CD3/CD7 by flow cytometry for cells on day 17 of differentiation induction. FIG. 32B shows results of determination of cytotoxic activity on Jurkat cells for cells on day 31 of differentiation induction. (Example 21)

Figure 33A:
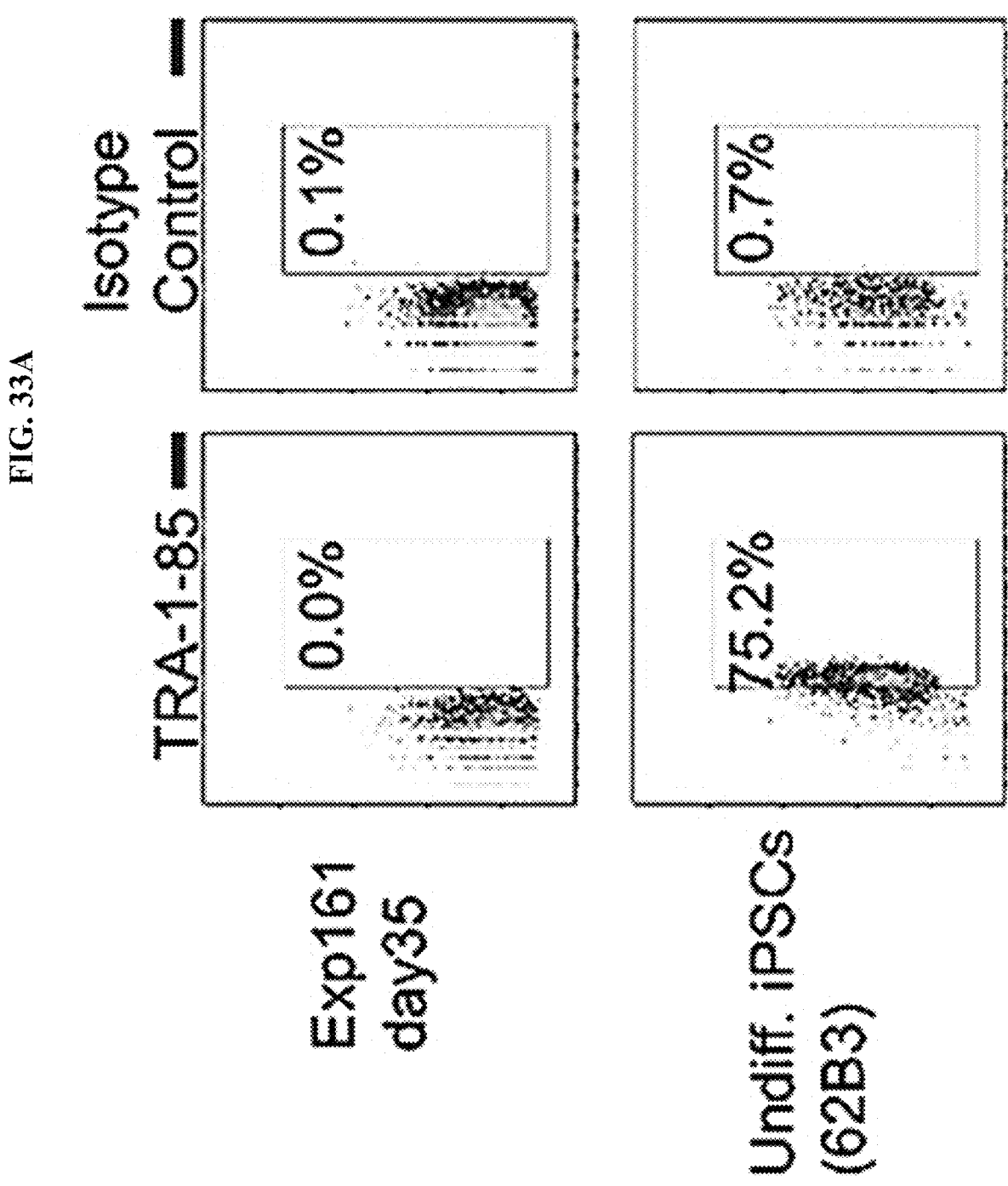
Figure 33B:
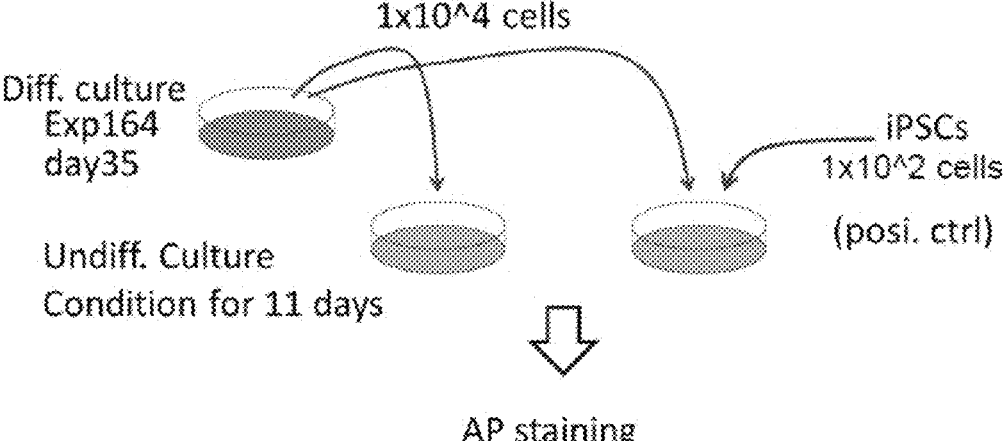
Figure 33C:
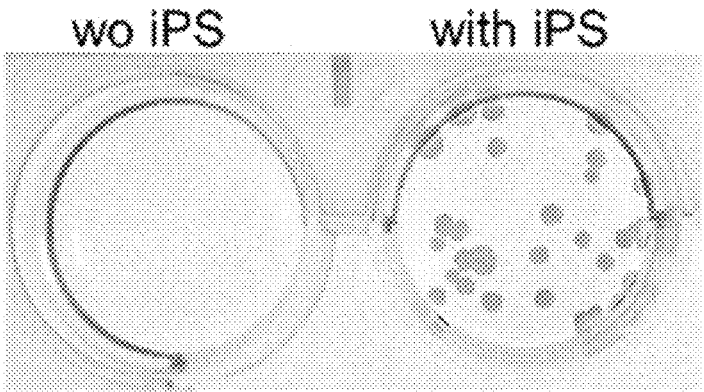

FIGS. 33A-33C show that undifferentiated cells are not present in a cell population. FIG. 33A shows results of evaluation by flow cytometry of the expression of an undifferentiation marker TRA-1-85 in a cell population on day 35 of differentiation induction under a serum-free condition free from using feeder cells. FIG. 33B is an illustration of a protocol for determining whether colonies of undifferentiated cells appear in a cell population. FIG. 33C shows that colonies of undifferentiated cells do not appear in a cell population. (Example 22)

Figure 34A:
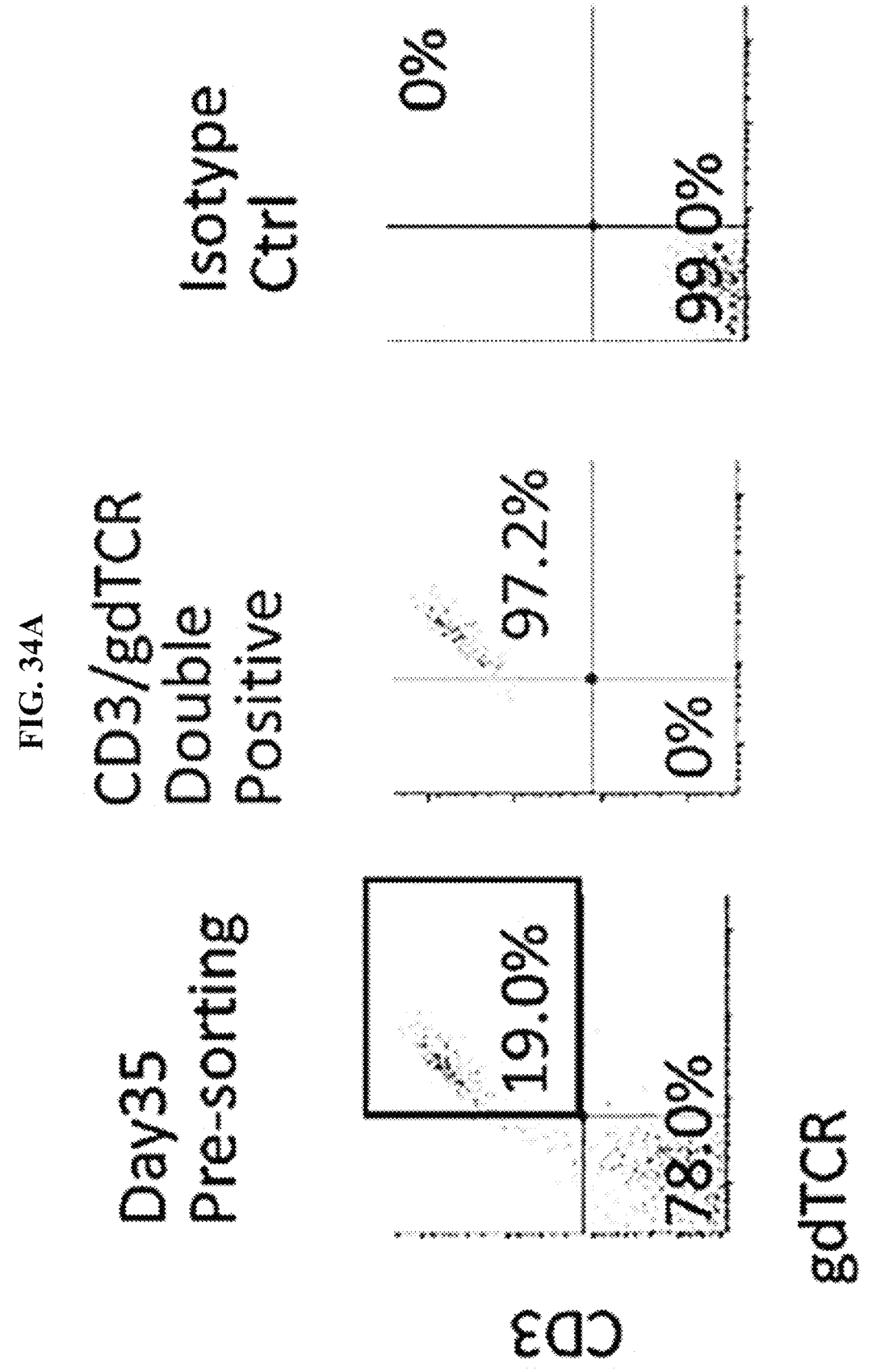
Figure 34B:
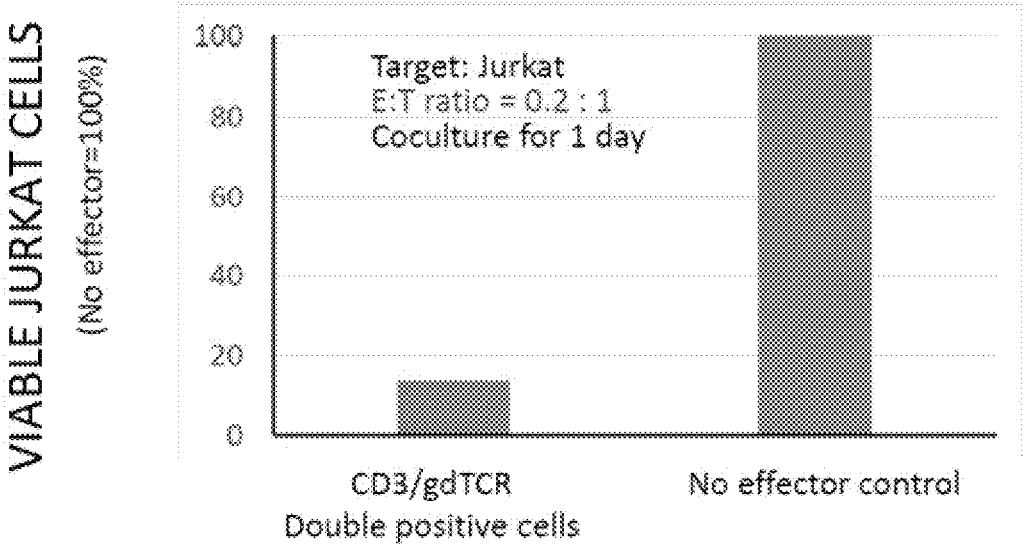

FIG. 34A shows the purification of CD3/γδT-positive cells from a cell population under a serum-free condition free from using feeder cells. FIG. 34B shows results obtained by further determining cytotoxic activity on Jurkat cells for purified cells. (Example 23)

DESCRIPTION OF EMBODIMENTS

The present invention relates to an iPS cell-derived γδT cell, which is a T cell derived from an iPS cell, wherein the T cell has antigen-specific cytotoxic activity in a MHC-unrestricted manner.

Human mature T cells are classified into two groups: αβ-type T cells having a T cell receptor (TCR) made up of an α-chain and a β-chain; and γδ-type T cells having a TCR made up of a γ-chain and a δ-chain. As used herein, the term "γδT cell" refers to the γδ-type T cell. In blood, the αβT cells account for a vast majority, whereas the γδT cells are a minority of from 1% to 5% of all T cells. The γδT cells undergo rearrangement of TCR genes in order to bind to diverse antigens and leave memory cells, and hence may be regarded as a component of the acquired immune system. Besides, the γδT cells also have a function of, for example, attacking tumor cells through antigen recognition similar to that by NK cells, which are innate immune cells, without requiring antigen recognition by a TCR. In addition, it is considered that the γδT cells have the functions of both the innate immune system and the acquired immune system. Meanwhile, against a tumor antigen, αβT cell-derived cytotoxic T cells (CTLs) may be said to be an acquired immune system requiring antigen information from dendritic cells. Thus, the γδT cells and the αβT cells completely differ from each other not merely in ratio of presence in blood, but also in their functions, and it is known that the processes of differentiation of the two types of cells also differ from each other (Non Patent Literature 3).

As used herein, the term "iPS cell" refers to an undifferentiated cell established by reprogramming a somatic cell by any of various methods. iPS cells serving as a starting material in the present invention are suitably iPS cells that are not iPS cells having a rearranged αβTCR gene. The iPS cells are most suitably iPS cells having a rearranged γδTCR gene. The iPS cells having a rearranged γδTCR gene are hereinafter sometimes referred to simply as "γδTCR-type iPS cells". As used herein, the term "rearranged γδTCR gene" refers to a gene encoding a TCR in which both of the rearrangement of a TCRG region and the rearrangement of a TCRD region have occurred. The TCRG region is made up of Vγ-Jγ, and the TCRD region is made up of Vδ-Dδ-Jδ.

Herein, the iPS cells may be generated by a method known per se or any method to be developed in the future. For example, the iPS cells may be generated on the basis of descriptions in Patent Literature 1 and Non Patent Literature 1.

(Method of Generating iPS Cell)

The iPS cell to be used for generating the γδT cell of the present invention may be generated by a method known per se or any method to be developed in the future. Specifically, for example, the iPS cell may be generated by a method described in Patent Literature 1 or Non Patent Literature 1. For example, the iPS cell may be generated by a method of generating iPS cells including the following steps 1) to 3):

1) a step of stimulating collected blood cells with IL-2 and a bisphosphonate (e.g., one kind or a plurality of kinds selected from zoledronic acid, pamidronic acid, alendronic acid, risedronic acid, ibandronic acid, incadronic acid, etidronic acid, minodronic acid, salts thereof, and hydrates thereof, preferably zoledronic acid);

2) a step of introducing at least four kinds of genes capable of expressing cell reprogramming factors (e.g., OCT3/4, SOX2, KLF4, and c-MYC) into the blood cells through use of a Sendai virus (SeV) vector; and 3) a step of culturing the cells having introduced therein the genes.

(Culture of iPS Cells)

As a basal medium that may be used for maintenance culture of the iPS cells, there may be used any of various stem cell maintenance media, such as StemFit™ AK02N (product name), StemFit™ AK03N (product name), Repro-Stem (product name), iPSellon (product name), Essential 8 (product name), and TeSR-E8 (product name). In particular, StemFit™ AK02N (product name) is preferred. The amount of a substance to be added to each medium may be appropriately increased or decreased depending on purposes. As an example of the substance to be added, Y27632, which is a Rho-Associated Coil Kinase (ROCK) inhibitor, may be used. In order to promote cell adhesion and growth, for example, a laminin-511-E8 fragment may be used for a culture substrate such as a culture dish. Specifically, iMatrix-511 silk (product name) or iMatrix-511 (product name) may be used. The manufacturers/distributors of reagents and the like to be used are not particularly limited as long as equivalent functions can be exhibited. At the time of the passage of the iPS cells, a protease such as trypsin may be used in detaching the cells from the culture vessel, and for example, TrypLE Select (product name) may be used.

(Differentiation Induction from iPS Cells into Hematopoietic Progenitor Cells)

In the step of differentiation induction treatment from the iPS cells into the γδT cells, first, the iPS cells are induced to differentiate into hematopoietic progenitor cells. In the method of generating an iPS cell-derived γδT cell of the present invention, the step of differentiation induction treatment from the hematopoietic progenitor cells into the γδT cells using as a starting material cells obtained by inducing the iPS cells to differentiate into the hematopoietic progenitor cells may be regarded as the method of generating an iPS cell-derived γδT cell. The method of generating an iPS cell-derived γδT cell may further include the step from the iPS cells to the hematopoietic progenitor cells. In addition, cells obtained by freezing and thawing the iPS cell-derived hematopoietic progenitor cells may be used in the method of the present invention. A freezing period is not particularly limited, but may be, for example, from 2 weeks to 1 year. In any case, the iPS cells of the present invention are suitably iPS cells that are not iPS cells having a rearranged αβTCR gene. The iPS cells is most suitably γδTCR-type iPS cells.

The step of differentiation induction from the iPS cells into the hematopoietic progenitor cells is not particularly limited, and a method known per se or any step to be developed in the future may be adopted. In the step of differentiation induction into the hematopoietic progenitor cells, the medium may be appropriately supplemented with one kind or a plurality of kinds selected from cytokines, such as FMS-like tyrosine kinase 3 ligand (FLT3L), stem cell factor (SCF), bone morphogenetic protein-4 (BMP4), basic fibroblast growth factor (bFGF), vascular endothelial growth factor (VEGF), IL-6, insulin-like growth factors (IGF-1), IL-7, IL-11, erythropoietin (EPO), thrombopoietin (TPO), IL-15, and IL-3. The medium may also be appropriately supplemented with fetal bovine serum (FBS) or fetal calf serum (FCS).

The differentiation induction treatment from the iPS cells of the present invention into the hematopoietic progenitor cells may be performed, for example, under a condition free from using feeder cells through culture in media described in the following 1-1) to 1-4). The culture may be performed in the following manner: until the hematopoietic progenitor cells are obtained, there may be used Y27632, which is a ROCK inhibitor, at a final concentration of from 0 μM to 50 μM, preferably from 1 μM to 30 μM, more preferably 10 μM, and a laminin-511 E8 fragment such as iMatrix-511 (product name) at from 0 μl to 50 μl, preferably from 1 μl to 30 μl, more preferably about 5 μl; and the medium is changed to StemFit™ AK02N free of the ROCK inhibitor and laminin-511-E8 the next day, and the medium is changed once every few days, for example, every 2 days. The frequency of medium change, medium change amount, and the like are not particularly limited, and an appropriate frequency and amount may be appropriately decided. In addition, the number of cells to be seeded may be appropriately increased or decreased. In addition, the manufacturers/distributors of reagents and the like to be used are not particularly limited as long as equivalent functions can be exhibited. The entire culture may be performed under the conditions of 37±0.5° C. and 5% $CO_2$. For passage, a protease such as trypsin, for example, TrypLE Select (product name) may be used in detaching the cells from the culture vessel.

1-1) Day 0 of Differentiation Induction

StemFit™ AK02N (product name) may be used as a basal medium. Culture may be performed in a culture system further including a GSK-3α/β inhibitor (CHIR99021, CAS number: 252917-06-9) at from 0 μM to 20 μM, preferably from 0.5 μM to 10 μM, more preferably 4 μM, BMP4 at from 0 ng/ml to 400 ng/ml, preferably from 10 ng/ml to 200 ng/ml, more preferably 80 ng/ml, and VEGF at from 0 ng/ml to 400 ng/ml, preferably from 10 ng/ml to 200 ng/ml, more preferably 80 ng/ml.

1-2) Day 2 of Differentiation Induction

Advanced DMEM/F12 (product name) or Essential 6 (product name) may be used as a basal medium. Culture may be performed in a culture system further including a selective ALK5, 4, 7 inhibitor (SB431542) at from 0 μM to 20 μM, preferably from 0.5 μM to 10 μM, more preferably from 2 μM to 4 μM, bFGF at from 0 ng/ml to 200 ng/ml, preferably from 1 ng/ml to 100 ng/ml, more preferably 50 ng/ml, SCF at from 0 ng/ml to 200 ng/ml, preferably from 1 ng/ml to 100 ng/ml, more preferably 50 ng/ml, and VEGF at from 0 ng/ml to 400 ng/ml, preferably from 10 ng/ml to 200 ng/ml, more preferably 80 ng/ml. In addition to the foregoing, L-glutamine, penicillin/streptomycin, a differentiation induction supplement for iPS/ES cells (e.g., StemFit (product name) For Differentiation: hereinafter "AS401"), or the like may be further appropriately selected and added. The optimal addition amounts thereof may be appropriately decided.

1-3) Day 4 of Differentiation Induction

Advanced DMEM/F12 (product name) or StemPro-34 SFM (product name) may be used as a basal medium. Culture may be performed in a culture system further including L-glutamine at from 0 mM to 20 mM, preferably from 0.5 mM to 10 mM, more preferably 2 mM, IL-3 at from 0 ng/ml to 200 ng/ml, preferably from 1 ng/ml to 100 ng/ml, more preferably 50 ng/ml, IL-6 at from 0 ng/ml to 200 ng/ml, preferably from 1 ng/ml to 100 ng/ml, more preferably 50 ng/ml, FLT3L at from 0 ng/ml to 200 ng/ml, preferably from 1 ng/ml to 100 ng/ml, more preferably 50 ng/ml, SCF at from 0 ng/ml to 200 ng/ml, preferably from 1 ng/ml to 100 ng/ml, more preferably 50 ng/ml, VEGF at from 0 ng/ml to 200 ng/ml, preferably from 1 ng/ml to 100 ng/ml, more preferably 20 ng/ml, and EPO at from 0 IU/ml to 100 IU/ml, preferably from 1 IU/ml to 50 IU/ml, more preferably 10 IU/ml. In addition to the foregoing, penicillin/streptomycin, a differentiation induction supplement for iPS/ES cells (e.g., AS401), or the like may be further appropriately selected and added. The optimal addition amounts thereof may be appropriately decided.

1-4) Day 6 to Day 8 of Differentiation Induction

Advanced DMEM/F12 (product name) or StemPro-34 SFM (product name) may be used as a basal medium. Culture may be performed in a culture system further including L-glutamine at from 0 mM to 50 mM, preferably from 1 mM to 20 mM, more preferably 2 mM, IL-3 at from 0 ng/ml to 200 ng/ml, preferably from 1 ng/ml to 100 ng/ml, more preferably 50 ng/ml, IL-6 at from 0 ng/ml to 200 ng/ml, preferably from 1 ng/ml to 100 ng/ml, more preferably 50 ng/ml, SCF at from 0 ng/ml to 200 ng/ml, preferably from 1 ng/ml to 100 ng/ml, more preferably 50 ng/ml, and EPO at from 0 IU/ml to 100 IU/ml, preferably from 1 IU/ml to 50 IU/ml, more preferably 10 IU/ml. In addition to the foregoing, penicillin/streptomycin, a differentiation induction supplement for iPS/ES cells (e.g., AS401), or the like may be further appropriately selected and added. The optimal addition amounts thereof may be appropriately decided.

(Feeder Cells)

Feeder cells may be cocultured in the culture of the iPS cells or the differentiation induction treatment of the iPS cells. As the feeder cells, there may be used one kind or a plurality of kinds of cell lines selected from, for example, mouse embryonic fibroblasts (MEFs), OP9, OP9/DLL1, OP9-DL4, and 10T1/2/DL4 cells. Meanwhile, when cells obtained by inducing differentiation of the iPS cells are to be administered to a human in cell therapy or the like, a stable production method free of any animal-derived substance is desired. In the present invention, differentiation induction into the γδT cell of the present invention may be performed without using feeder cells by using the above-mentioned laminin-511 E8 fragment and medium components in a well-designed manner.

(Differentiation Induction from iPS Cell-Derived Hematopoietic Progenitor Cells into γδT Cells)

The process of differentiation induction from the iPS cell-derived hematopoietic progenitor cells into the γδT cells may be performed as coculture with feeder cells, or may be performed as culture under a condition free from using feeder cells. Further, culture may be performed under a serum-free condition, and culture may be performed under an animal-derived component-free condition. In addition, the process of differentiation induction from the iPS cell-derived hematopoietic progenitor cells into the γδT cells may involve culture under a hypoxic condition. The expression "under a hypoxic condition" means that an $O_2$ concentration under culture conditions in the process of differentiation induction from the iPS cell-derived hematopoietic progenitor cells into the γδT cells is lower than an $O_2$ concentration at which culture is generally performed. The $O_2$ concentration at which the culture under a hypoxic condition is performed is not particularly limited, but is, for example, less than 20% (v/v), preferably less than 10% (v/v).

In addition, a γδT cell stimulant may be added in order to obtain desired γδT cells, or may not be added depending on culture conditions. Examples of the γδT cell stimulant include a phosphoric acid compound that is a metabolite of a mevalonate pathway or a non-mevalonate pathway serving as an isoprenoid biosynthesis pathway, or a derivative thereof. Examples of the phosphoric acid compound that is a metabolite of the mevalonate pathway or the non-mevalonate pathway serving as the isoprenoid biosynthesis pathway include (E)-4-hydroxy-3-methyl-but-2-enyl pyrophosphate (HMBPP) and isopentenyl diphosphate (IPP). An example of the derivative is bromohydrin pyrophosphate (BrHPP). Another example of the γδT cell stimulant is a specific inhibitor of a farnesyl pyrophosphate (FPP) synthase serving as a rate-limiting enzyme of the biosynthesis pathway. The specific inhibitor of the FPP synthase promotes the accumulation of the phosphoric acid compound in cells. Examples of the FPP synthase-specific inhibitor include nitrogen-containing bisphosphonates (N-BPs), specifically zoledronic acid and pamidronate. Further, IL-15 and IL-2 each also have a function as a γδT cell stimulant.

A. System Involving Coculture with Feeder Cells

A-1) Day 10~ of Differentiation Induction

For example, in culture from day 10 (hematopoietic progenitor cells) onward after the differentiation induction from the iPS cells by the above-mentioned treatments 1-1) to 1-4), αMEM (product name) may be used as a basal medium. The culture may be performed in a culture system further including FBS at from 0% to 30%, preferably from 0% to 20%, more preferably from 10% to 20%, SCF at from 0 ng/ml to 100 ng/ml, preferably from 1 ng/ml to 50 ng/ml, more preferably 10 ng/ml, IL-7 at from 0.1 ng/ml to 20 ng/ml, preferably from 0.5 ng/ml to 10 ng/ml, more preferably 5 ng/ml, FLT3L at from 0.1 ng/ml to 50 ng/ml, preferably from 1 ng/ml to 20 ng/ml, more preferably 5 ng/ml, and L-ascorbic acid at from 1 μg/ml to 1,000 g/ml, preferably from 10 μg/ml to 500 μg/ml, more preferably 100 μg/ml. Further, the culture system may include IL-2 at from 0 ng/ml to 200 ng/ml, preferably from 1 ng/ml to 100 ng/ml, more preferably 10 ng/ml, or may include TPO at from 0 ng/ml to 200 ng/ml, preferably from 1 ng/ml to 100 ng/ml, more preferably 10 ng/ml. In addition to the foregoing, penicillin/streptomycin or the like may be further appropriately selected and added. In addition, a 0.1% Polyvinyl alcohol+4% B27 (product name) supplement or the like may be used in place of FBS. The manufacturers/distributors of reagents and the like to be used are not particularly limited as long as equivalent functions can be exhibited. The optimal addition amounts thereof may be appropriately decided. The culture may be performed by seeding the cells (hematopoietic progenitor cells) on day 10 after differentiation induction into a culture substrate such as a culture dish seeded with feeder cells. The medium is changed, for example, every 2 days, and the supernatant may be collected on day 12, day 18, and day 24 after differentiation induction by pipetting and transferred onto fresh feeder cells to continue culture. The frequency of medium change, medium change amount, and the like are not particularly limited, and an appropriate frequency and amount may be appropriately decided.

A-2) Day 30 or Day 31~ of Differentiation Induction

The cells that have been cultured from day 10 to day 30 or day 31 after differentiation induction through use of the above-mentioned medium may be cultured under a condition free from using feeder cells. In the culture under such condition, RPMI 1640 medium may be used as a basal medium. The culture may be performed in a medium further containing FBS at from 0% to 30%, preferably from 0% to 20%, more preferably from 10% to 20%. A 0.1% Polyvinyl alcohol+4% B27 (product name) supplement or the like may be used in place of FBS. Further, the culture may be performed in a culture system including IL-2 and/or IL-15 at from 0 ng/ml to 200 ng/ml, preferably from 1 ng/ml to 100 ng/ml, more preferably 10 ng/ml, or the culture may be performed in a culture system including Immunace (product name) at from 0 IU/ml to 1,000 IU/ml, from 10 IU/ml to 500 IU/ml, preferably 100 IU/ml and 2-Mercaptoethanol (2-Me) at from 0 µM to 100 M, from 1 µM to 50 µM, preferably 10 µM. In addition to the foregoing, penicillin/streptomycin or the like may be further appropriately added.

Further, for example, HMBPP may be added as a γδT cell stimulant. Its addition concentration only needs to be a concentration at which the γδT cells are stimulated and which does not cause cytotoxicity, and is not particularly limited, but may be set to, for example, from 0 nM to 100 nM, preferably from 0.01 nM to 20 nM, more preferably 1 nM.

B. System Involving Culture Free from Using Feeder Cells

B-1) Day 10~ of Differentiation Induction

For example, culture from day 10 (hematopoietic progenitor cells) onward after the differentiation induction from the iPS cells by the above-mentioned treatments 1-1) to 1-4) may involve culture using a culture substrate coated with vascular cell adhesion molecule-1 (VCAM1), and delta-like protein 4 (DLL4) or delta-like protein 1 (DLL1). From day 10 to day 24 of differentiation induction, culture may be performed in, for example, Lymphoid progenitor Expansion Medium (product name) included in a StemSpan™ T cell generation kit (product name). Medium change was performed in accordance with the protocol of the StemSpan™ kit. Specifically, it may be appropriate that the medium be further added on day 13 of differentiation induction, and the medium be changed on each of day 17 and day 20 of differentiation induction. Around day 17 to day 24 of differentiation induction, the medium may be changed to T cell progenitor Maturation Medium (product name) included in the above-mentioned kit. It may be appropriate that the above-mentioned medium be further added on day 27 of differentiation induction, and thereafter, the medium be changed about twice a week, such as day 31 and day 34 of differentiation induction. The frequency of medium change, medium change amount, and the like are not particularly limited, and an appropriate frequency and amount may be appropriately decided.

B-2) Around Day 17 to Day 24~ of Differentiation Induction

Culture may be continued by the method described in B-1), but culture may be performed in a medium supplemented with a γδT cell stimulant from around day 17 to day 24 of differentiation induction. The decreasing tendency of the number of cells, which is sometimes observed from around day 17 to day 24 of differentiation induction, is ameliorated by the supplementation with the γδT cell stimulant. Specifically, the culture may be performed in the medium described in A-2 that is supplemented with IL-2 and/or IL-15, and γδT cell stimulants, such as HMBPP and the FPP synthase-specific inhibitor. The culture may also be performed in the medium described in A-2 that is free of FBS and is similarly supplemented with HMBPP. The culture may also be performed in RPMI 1640 medium containing AS401 and being supplemented with IL-2 and/or IL-15, and HMBPP, instead of the medium described in A-2.

B-3) Day 10~ of Differentiation Induction

Culture may be continued by a method involving further incorporating Dickkopf-1 (DKK1) and/or azelaic acid (AZA) into the medium conditions described in B-1). Further, from around day 17 to day 24 of differentiation induction, culture may be performed in a medium supplemented with a γδT cell stimulant. From around day 17 to day 24 of differentiation induction, specifically, culture may be performed in the medium described in A-2 that is supplemented with HMBPP. The culture may also be performed in the medium described in A-2 that is free of FBS and is similarly supplemented with HMBPP. The culture may also be performed in RPMI 1640 medium containing AS401 and being supplemented with IL-2 and/or IL-15, and a γδT cell stimulant such as HMBPP, instead of the medium described in A-2.

C. Culture using Beads

The cells that have been cultured by the differentiation induction method of the present invention may be cultured using beads. The size of the beads is not particularly limited, and may be smaller than the size of cells, or may be equal to or larger than the size of cells. For example, when the cells on day 10 of differentiation induction are cultured under the above-mentioned various conditions, the culture may be performed by mixing the beads into the medium. The beads only need to be beads of a material usable for cell culture, and are not particularly limited, but specifically, Dynabeads Protein G (product name) may be used. The culture may be performed under a condition free from using feeder cells by coating the beads with, for example, VCAM1 and DLL4.

D. Culture Using Animal-Derived Component-Free Medium

D-1) Day 10~ of Differentiation Induction

The cells that have been cultured by the differentiation induction method of the present invention may be cultured under a condition involving using an animal-derived component-free medium. For example, culture from day 10 (hematopoietic progenitor cells) onward after the differentiation induction from the iPS cells by the above-mentioned treatments 1-1) to 1-4) may involve culture using a culture substrate coated with vascular cell adhesion molecule-1 (VCAM1), and delta-like protein 4 (DLL4) or delta-like protein 1 (DLL1). Around day 10 to day 24 of differentiation induction, for example, RPMI 1640 containing AS401 may be used as a basal medium for the animal-derived component-free medium. The medium may further contain, for example, SCF, IL-7, FLT3L, L-ascorbic acid, IL2, and TPO described in A-1.

D-2) Around Day 17 to Day 24~ of Differentiation Induction

From around day 17 to day 24 of differentiation induction, culture may be performed in the medium described in A-2 that is supplemented with IL-2, IL-15, and the γδT cell stimulant. Such medium may use RPMI 1640 containing AS401 as a basal medium. From around day 17 to day 24 of differentiation induction, specifically, culture may be performed in a medium supplemented with one or a plurality of IL-2, IL-15, and HMBPP.

(γδT Cells Obtained Through Differentiation Induction)

The γδT cells generated by the differentiation induction method of the present invention are T cells having a peculiar T cell receptor (TCR) made up of a γ-chain and a δ-chain on the surface thereof. For such cell surface, the expressions of cell markers, such as CD3, CD7, CD8a, CD45RA, and γδTCR, may be determined. The γδT cells of the present invention preferably express, in particular, one or a plurality selected from CD7, CD8a, and CD45RA, and meanwhile, are preferably free from expressing one or a plurality selected from CD25, IFNγ, CD5, and CD27. The obtained iPS cell-derived γδT cells have a feature of having antigen-specific cytotoxic activity in a MHC-unrestricted manner. Further, a difference is found between the patterns of cell surface markers in the γδT cells generated by inducing differentiation of iPS cells of the present invention and γδT cells separated from peripheral blood. For example, for CD7 and CD8a, the iPS cell-derived γδT cells show higher expression tendencies, and for IL2RA (CD25), CD5, and IFNγ, the γδT cells separated from peripheral blood show higher expression tendencies. In addition, for example, for CD45RA, the iPS cell-derived γδT cells show a higher expression tendency, and for CD27, the γδT cells separated from peripheral blood show a higher expression tendency.

The γδT cells thus caused to undergo differentiation induction may be isolated by appropriately selecting a known technique. An example of such known technique is such flow cytometry as described in Examples to be described later, involving using an antibody against a cell surface marker and a cell sorter. In the case of isolating "T cells having desired antigen specificity" from a human, a method involving performing purification using, for example, an affinity column on which a desired antigen is immobilized may be adopted.

A cell population of the purified γδT cells is made up of homogeneous cells, and is distinguished from a cell population made up of γδT cells separated from peripheral blood. The γδT cell population of the present invention has higher cytotoxic activity in an antigen-specific manner than a γδT cell population separated from peripheral blood.

The cell population including the γδT cells includes, for example, many cells having base sequences identical to each other in a complementarity determining region (CDR) of a TCR gene. The cell population has a feature in that γδT cells having base sequences identical to each other particularly in a CDR3 region among CDRs are included in the γδT cells that make up the cell population at a high ratio, for example, at a ratio of 90% or more. The cell population including the γδT cells of the present invention may include $1 \times 10^5$ or more γδT cells.

Further, the cell population including the γδT cells of the present invention includes γδT cells, which show a higher expression amount than γδT cells separated from peripheral blood in terms of expression amount of CD7 and/or CD8a, at a ratio of 90% or more of the γδT cells that make up the cell population. Further, in terms of expression amount of one or a plurality selected from CD25, INFγ, and CD5, γδT cells showing a lower expression amount than γδT cells separated from peripheral blood are included at a ratio of 90% or more of the γδT cells that make up the cell population. Further, γδT cells showing a higher expression amount of CD45RA than γδT cells separated from peripheral blood and ex vivo expanded, and a lower expression amount than the γδT cells separated from peripheral blood and ex vivo expanded in terms of expression amount of CD27 are included at a ratio of 70% or more of the γδT cells that make up the cell population.

In addition, the cell population including the γδT cells of the present invention has a feature in that 10% or less of the γδT cells that make up the cell population are undifferentiated cells, and further, it is suitable that no undifferentiated cells be present in the γδT cells that make up the cell population. Whether or not a given cell is an undifferentiated cell may be determined, for example, with a marker indicating undifferentiation such as TRA-1-85.

The γδT cells generated through treatment by the differentiation induction treatment method of the present invention have an excellent immune function, and hence may be used for, for example, treatment or prevention of a disease, such as a tumor, an infectious disease (e.g., viral infectious disease), or an autoimmune disorder. Further, the cell population of the γδT cells produced by the method of the present invention may be utilized as an antigen-specific cellular immunotherapeutic agent or a pharmaceutical composition by being incorporated thereinto as an active ingredient. The γδT cells generated through treatment by the differentiation induction treatment method of the present invention can be utilized for such formulation even after being frozen and thawed. The γδT cell population is expected to be also applicable to an immune cell treatment method making use thereof. The γδT cell population of the present invention is expected to further enhance the effect of the γδT cells by being used in combination with an immune checkpoint inhibitor. The immune checkpoint inhibitor is not limited to ones known per se and ones to be developed in the future, but examples thereof include drugs targeting immune checkpoints, such as PD-1, PD-L1, and CTLA-4. Further, like NK cells, the γδT cells are expected to have an antibody-dependent cellular cytotoxicity (ADCC) action of enhancing the effect of a molecularly targeted therapeutic agent/antibody formulation used for the treatment of any of various cancers (e.g., Herceptin or Rituxan), and hence can be expected to have a high therapeutic effect when used in combination with any such antibody formulation. The pharmaceutical composition containing the γδT cell population of the present invention may be prepared through formulation by a known pharmaceutical method.

In such formulation, a pharmacologically acceptable carrier or medium, specifically, sterile water or physiological saline, a vegetable oil, a solvent, a base, an emulsifier, a suspending agent, a surfactant, a stabilizer, a vehicle, an antiseptic agent, a binder, a diluent, a tonicity agent, a soothing agent, an extender, a disintegrant, a buffer, a coating agent, a lubricant, a colorant, a solubilizing agent, other additives, or the like may be appropriately combined. In addition, the pharmaceutical composition may be used in combination with, for example, a known pharmaceutical composition or immunostimulator to be used for the treatment or prevention of the above-mentioned disease. When the pharmaceutical composition of the present invention is administered, its dose is appropriately selected depending on, for example, the age, body weight, symptoms, and health status of a subject, and the kind of the composition.

The present invention also encompasses an antigen-specific cellular immune treatment method, including administering the iPS cell-derived γδT cell of the present invention. The present invention also encompasses a treatment method for a disease, such as cancer, an infectious disease, or an autoimmune disorder, the method including administering the iPS cell-derived γδT cell of the present invention. In the method of the present invention, the dose of the active ingredient for a subject varies depending on, for example, the body weight, age, and symptoms of the subject, and an administration method, but could be appropriately selected by a person skilled in the art.

EXAMPLES

The present invention is specifically described below by way of Examples for a better understanding of the present invention. Needless to say, however, the present invention is by no means limited to these Examples and the like.

(Example 1) Differentiation Induction from iPS Cells

In this Example, a differentiation induction treatment method for γδT cells generated from γδTCR-type iPS cells generated by a method of Non Patent Literature 1 is described.

(1-1) Culture of γδTCR-type iPS Cells (62B3 Line)

γδTCR-type iPS cells (62B3 line) cultured under a condition free from using feeder cells were passaged into a 6-well plate at $2 \times 10^3$/well, and subjected to maintenance culture. In the maintenance culture, StemFit™ AK02N (manufactured by Ajinomoto) containing 1.6 μg/well of iMatrix-511 (manufactured by Nippi) was used. 0.5× TrypLE™ select (manufactured by Thermo Fisher) was used for detaching and dispersing the cells at the time of the passage, and a medium obtained by supplementing Stem-Fit™ AK02N with Y27632 (manufactured by Wako Pure Chemical Industries) at a final concentration of 10 μM and 3.2 μl of iMatrix-511 was used for passage culture. The next day, the medium was changed to StemFit™ AK02N free of Y27632 and iMatrix-511, and thereafter, the medium was changed every 2 days. The medium was added at 1.5 ml/well. Culture in all cases, including the following steps and Examples to be described later, was performed under the conditions of 37±0.5° C. and 5% $CO_2$.

(1-2) Day 0 of Differentiation Induction

After 7 days from the passage in (1-1) described above, the medium was changed to a medium shown in Table 1 (Step 1) at 2 ml/well.

TABLE 1

| | | Step 1 | |
|---|---|---|---|
| | Manufacturer | Product number | Concentration |
| Stem Fit | Ajinomoto | AK02N | |
| CHIR99021 | TOCRIS | 4423 | 4 μM |
| rh BMP4 | R&D | 314-BP | 80 ng/ml |
| rh VEGF | R&D | 293-VE | 80 ng/ml |

(1-3) Day 2 of Differentiation Induction

After 2 days from (1-2) described above, the medium was changed to a medium shown in Table 2 (Step 2) at 2 mi/well.

TABLE 2

| | | Step 2 | |
|---|---|---|---|
| | Manufacturer | Product number | Concentration |
| Advanced DMEM/F12 | gibco | 12634-10 | |
| AS401 | Ajinomoto | 20170228A | 20% (v/v) |
| L-Glutamine | gibco | 25030-081 | 2 mM |
| Penicillin-Streptomycin | gibco | 15140-122 | 50 Unit/ml Pen 50 μg/ml Strep |
| SB43152 | FUJIFILM Wako Pure Chemical Corporation | 033-24631 | 2 μM |
| rh VEGF | R&D | 293-VE | 80 ng/ml |
| bFGF | Wako | 060-04543 | 50 ng/ml |
| SCF | R&D | 255-SC | 50 ng/ml |

(1-4) Day 4 of Differentiation Induction

After 2 days from (1-3) described above, the medium was changed to a medium shown in Table 3 (Step 3) at 2 ml/well.

TABLE 3

| | | Step 3 | |
|---|---|---|---|
| | Manufacturer | Product number | Concentration |
| Advanced DMEM/F12 | gibco | 12634-10 | |
| AS401 | Ajinomoto | 20170228A | 20% (v/v) |
| L-Glutamine | gibco | 25030-081 | 2 mM |
| Penicillin-Streptomycin | gibco | 15140-122 | 50 Unit/ml Pen 50 μg/ml Strep |
| SCF | R&D | 255-SC | 50 ng/ml |
| IL3 | Reprotech | AF-200-03 | 50 ng/ml |
| IL6 | R&D | 206-IL-050 | 50 ng/ml |
| Flt3L | R&D | 308-FK-025 | 50 ng/ml |
| rh VEGF | R&D | 293-VE | 20 ng/ml |
| EPO | Kyowa Hakko Kirin | | 10 IU/ml |

(1-5) Day 6 of Differentiation Induction

After 2 days from (1-4) described above, the medium was changed to a medium shown in Table 4 (Step 4) at 2 ml/well.

TABLE 4

| | | Step 4 | |
|---|---|---|---|
| | Manufacturer | Product number | Concentration |
| Advanced DMEM/F12 | gibco | 12634-10 | |
| AS401 | Ajinomoto | 20170228A | 20% (v/v) |
| L-Glutamine | gibco | 25030-081 | 2 mM |
| Penicillin-Streptomycin | gibco | 15140-122 | 50 Unit/ml Pen 50 μg/ml Strep |
| SCF | R&D | 255-SC | 50 ng/ml |
| IL6 | R&D | 206-IL-050 | 50 ng/ml |
| EPO | Kyowa Hakko Kirin | | 10 IU/ml |

(1-6) Day 8 of Differentiation Induction

After 2 days from (1-5) described above, the medium was changed to the same medium as the medium shown in Table 4 (Step 4) at 2 ml/well.

(1-7) Evaluation of Cells on Day 10 of Differentiation Induction

Figure 1A:
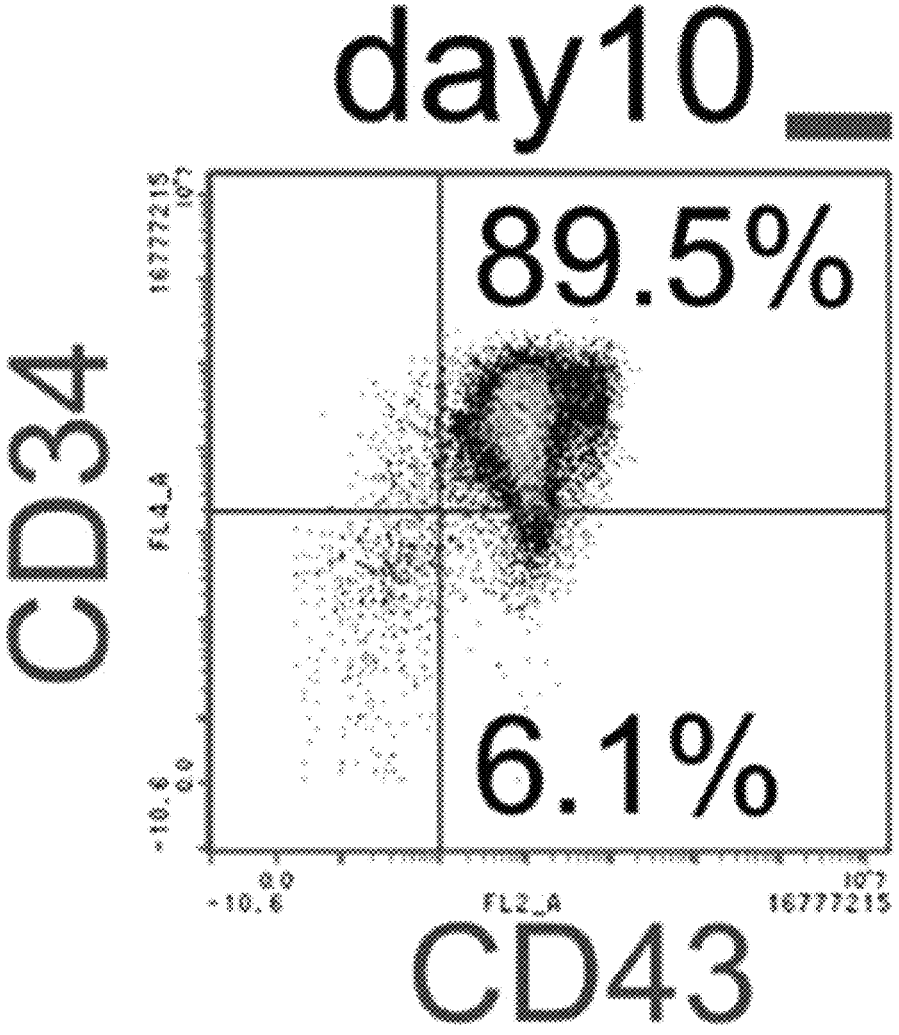
FIG. 1A shows results of evaluation of the expression of CD34/CD43 by flow cytometry for cells on day 10 of differentiation induction.

The expression of CD34/CD43 was evaluated by flow cytometry. CD34$^+$/CD43$^+$ cells and CD34$^-$/CD43$^+$ cells were detected in large numbers. That is, the cells had differentiated into hematopoietic progenitor cells (FIG. 1A).

(1-8) Day 10 of Differentiation Induction

The cells except for those subjected to flow cytometry in (1-7) described above were seeded into a 12-well culture dish seeded with OP9/N-DLL1 cells serving as feeder cells. A medium having the composition shown in Table 5 was used in a medium amount of 1 ml/well, and half of the medium was changed every 2 days.

TABLE 5

| | Step 5 | | |
| | day 10– Manufacturer | Product number | Concentration |
| --- | --- | --- | --- |
| 20% FBS/αMEM | gibco | 11900-016 | |
| Penicillin-Streptomycin | gibco | 15140-122 | 50 Unit/ml Pen 50 μg/ml Strep |
| IL2 | Reprotech | 200-02 | 10 ng/ml |
| IL7 | R&D | 207-IL-010 | 5 ng/ml |
| Flt3L | R&D | 308-FK-025 | 5 ng/ml |
| L-Ascorbic acid | Nacalai | 03420-52 | 100 μg/ml |

(1-9) Evaluation of Cells on Day 31 of Differentiation Induction

The expression of CD3/γδTCR was evaluated by flow cytometry. As a result, a large number of CD3$^+$/TCR$^+$ cells were detected to verify differentiation into TCR cells (FIG. 1$i$). The obtained cells are hereafter in this Example referred to as "iPS cell-derived γδT cells."

(1-10) Evaluation of Cells on Day 31 of Differentiation Induction

Cytotoxicity assay against Jurkat cells (derived from human leukemia T cells) was performed. At effector:target (E:T) ratio=2:1, 5×10$^4$ Jurkat cells (T) stained with a fluorescent dye CFSE were added per well of a 96-well culture dish, and 1×10$^5$ of the iPS cell-derived γδT cells (E) were added thereto, followed by 16 hours of culture. Dead cells were stained by 7-amino-actinomycin D (7-AAD) staining. Cell death (7-AAD-positive) was recognized for many of the Jurkat cells (CFSE-positive cells). That is, it was recognized that the iPS cell-derived γδT cells had a cytotoxic function. Even though activating stimulation culture of the γδT cells was not performed in this Example, cytotoxic activity was recognized.

(Example 2) Differentiation Induction from iPS Cells

In this Example, with regard to the γδT cells generated by differentiation induction treatment from the γδTCR-type iPS cells generated by the method of Non Patent Literature 1, medium components from day 10 of differentiation induction onward and medium components from day 31 of differentiation induction onward differ from those of Example 1. In particular, the medium components from day 31 of differentiation induction onward include HMBPP serving as a γδT cell stimulant.

(2-1) Until day 10 of differentiation induction treatment, the same treatments as in (1-1) to (1-6) of Example 1 were performed.

(2-2) Day 10~ of Differentiation Induction

The cells generated in (1-6) of Example 1 described above were seeded into a 12-well culture dish seeded with OP9/N-DLL1 cells serving as feeder cells. 1 ml/well of a medium having the composition of a medium shown in Table 6 (Step 5) was entirely changed every 7 days.

TABLE 6

| | Step 5 (Example 2) | | |
| | day 10– Manufacturer | Product number | Concentration |
| --- | --- | --- | --- |
| 20% FBS/αMEM | gibco | 11900-016 | |
| Penicillin-Streptomycin | gibco | 15140-122 | 50 Unit/ml Pen 50 μg/ml Strep |
| SCF | R&D | 255-SC | 100 ng/ml |
| Flt3L | R&D | 308-FK-025 | 100 ng/ml |
| TPO | Peprotech | AF-300-18-10 | 100 ng/ml |
| IL-7 | R&D | 207-IL-010 | 100 ng/ml |
| L-Ascorbic acid | Nacalai | 03420-52 | 100 μg/ml |

(2-3) Evaluation of Cells on Day 17 of Differentiation Induction

Figure 2A:
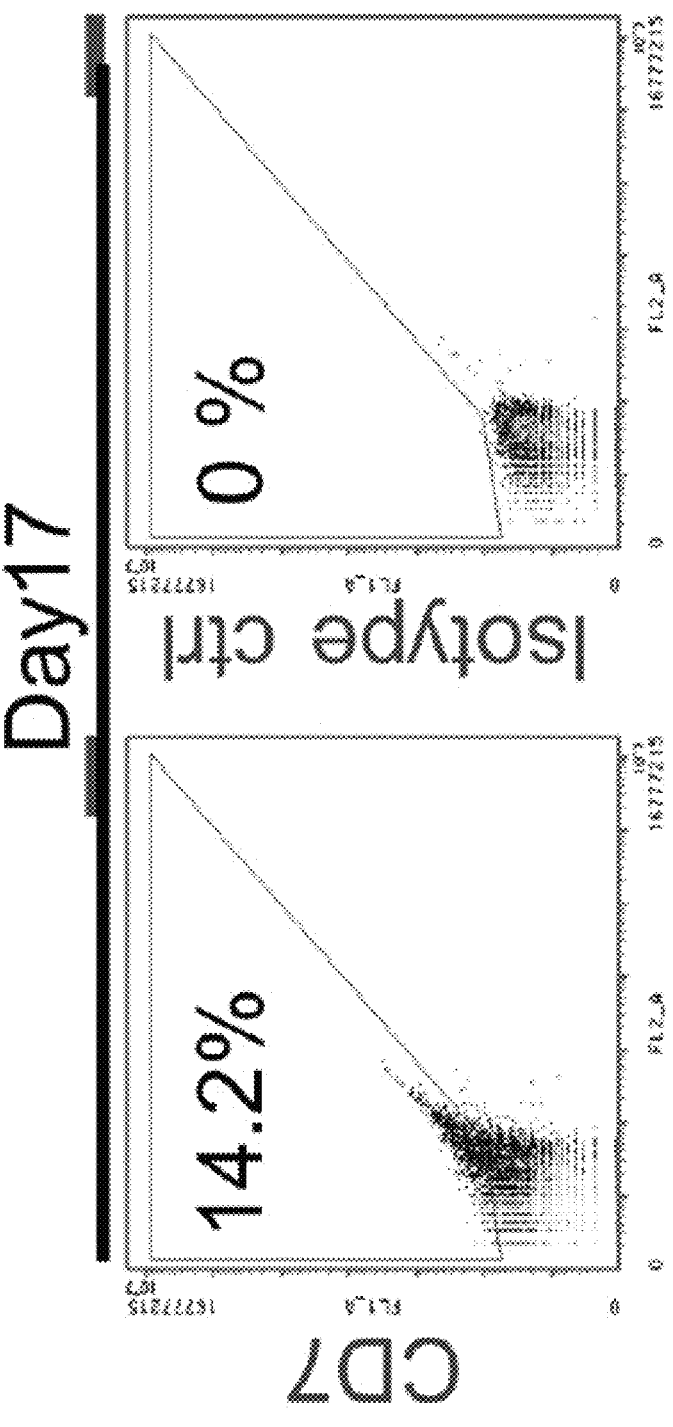
FIG. 2A shows results of evaluation of the expression of CD7 (T cell differentiation marker) by flow cytometry for cells on day 17 of differentiation induction.

The expression of CD7 (T cell differentiation marker) was evaluated by flow cytometry. CD7-positive cells were found, revealing that differentiation had proceeded into T cells (FIG. 2A).

(2-4) Day 31~ of Differentiation Induction

With a γδT cell stimulation medium shown in Table 7, half of the medium was changed every 2 days. The γδT cell stimulation medium contains HMBPP.

TABLE 7

| | γδT stimulation medium | | |
| | day 31– Manufacturer | Product number | Concentration |
| --- | --- | --- | --- |
| RPMI 1640 | Nacalai | 30264-85 | |
| FBS | SIGMA | F7524 | 10% (v/v) |
| Penicillin-Streptomycin | gibco | 15140-122 | 50 Unit/ml Pen 50 μg/ml Strep |
| IL-2 | Reprotech | 200-02 | 100 ng/ml |
| HMBPP | cayman chemical company | 13580 | 1 nM |

(2-5) Evaluation of Cells on Day 54 of Differentiation Induction

Figure 2B:
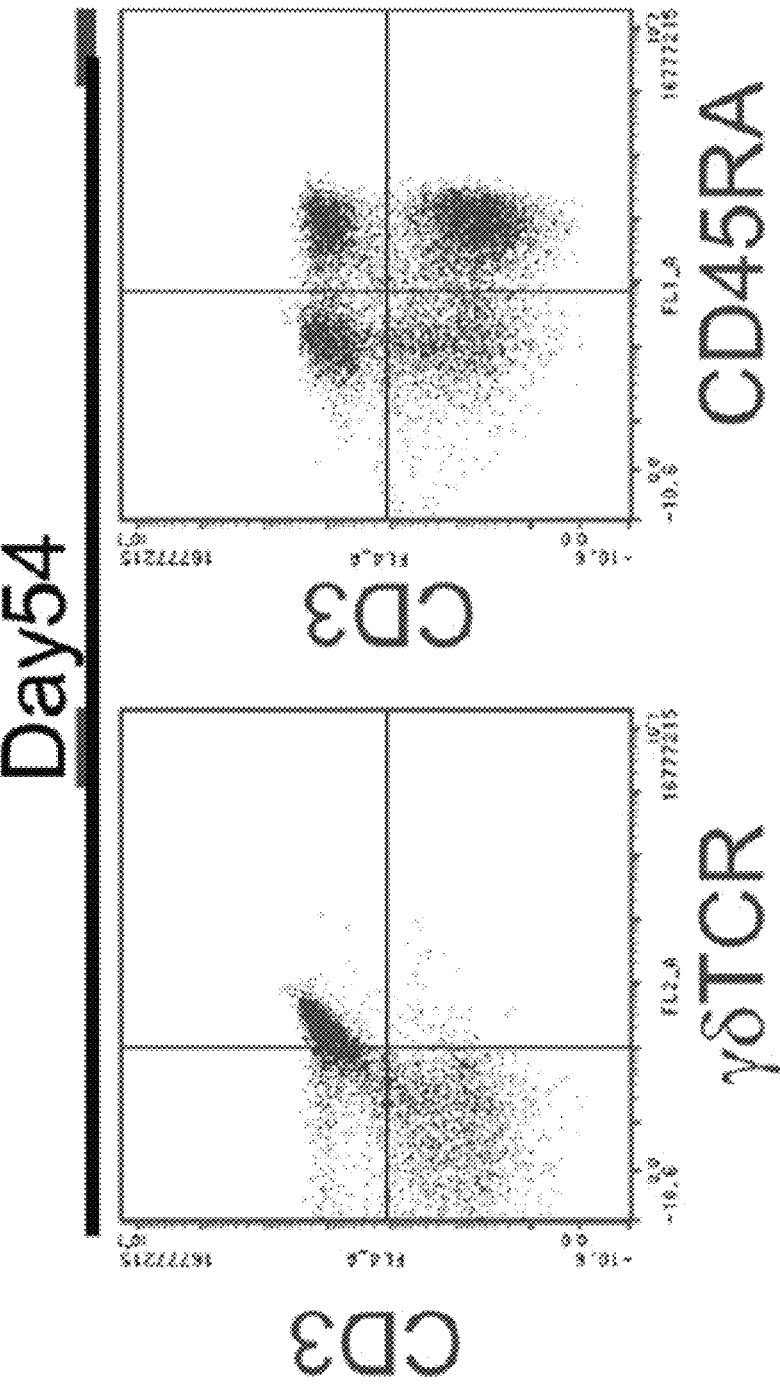
FIG. 2B shows results of evaluation of the expression of CD3/γδTCR/CD45RA by flow cytometry for cells on day 54 of differentiation induction. (Example 2)

The expression of CD3/γδTCR was evaluated by flow cytometry. A large number of CD3$^+$/TCR$^+$ cells were detected to verify differentiation into TCR cells. That is, it was recognized that the obtained cells were iPS cell-derived γδT cells. In addition, the expression CD45RA, generally used as an indicator of the maturation of T cells, was also evaluated, and as a result, it was revealed that CD3$^+$ cells included both CDRA$^+$ cells and CDRA$^-$ cells (FIG. 2B).

(Example 3) Differentiation Induction from iPS Cells Under Condition Involving Using Feeder Cells In this Example, description is made of γδT cells generated by differentiation induction treatment from γδTCR-type iPS cells generated by the method of Non Patent Literature 1 in the same manner as in Example 1. Differentiation induction treatment was performed in the same manner as in Example 1, and from day 31 onward, half of the γδT cell stimulation medium (containing HMBPP and FBS) was changed every 2 days in the same manner as in (2-4) of Example 2. Then, evaluation of marker expression and cytotoxicity assay were performed.

(3-1) Until Day 10 of Differentiation Induction Treatment, the Same Treatments as in (1-1) to (1-6) and (1-8) Described in Example 1 were Performed.

(3-2) Evaluation of Cells on Day 17 of Differentiation Induction

Figure 3A:
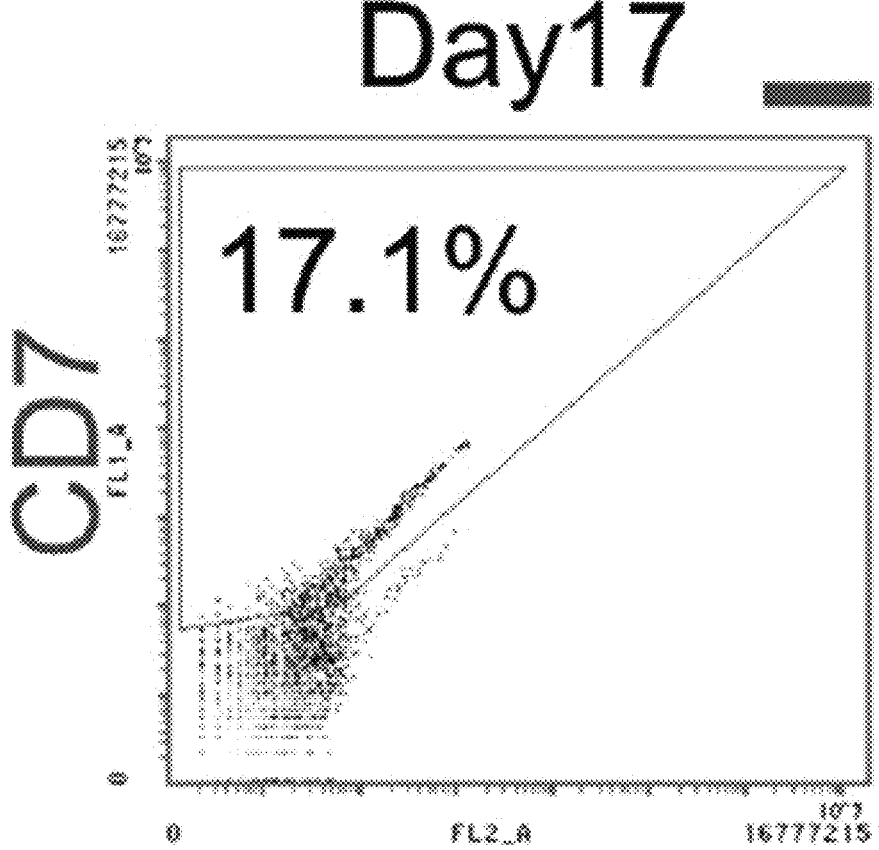
FIG. 3A shows results of evaluation of the expression of CD7 by flow cytometry for cells on day 17 of differentiation induction.

The expression of CD7 (T cell differentiation marker) was evaluated by flow cytometry. CD7-positive cells were detected, revealing that differentiation had proceeded into T cells (FIG. 3A).

(3-3) Evaluation of Cells on Day 55 of Differentiation Induction

Figure 3B:
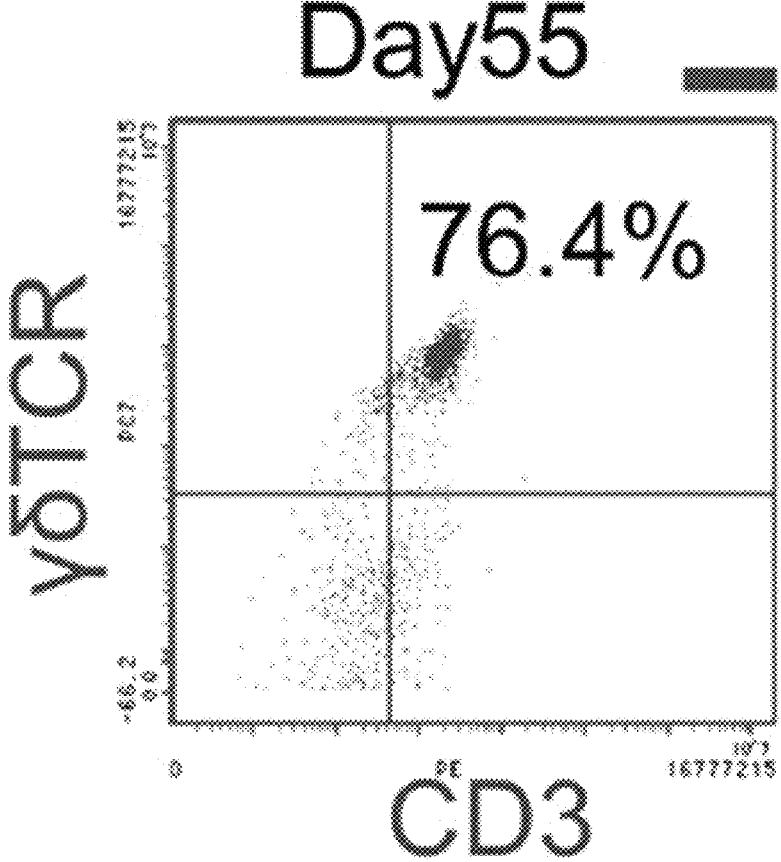
FIG. 3B shows results of evaluation of the expression of CD3/γδTCR by flow cytometry for cells on day 55 of differentiation induction.

The expression of CD3/γδTCR was evaluated by flow cytometry. A large number of $CD3^+/TCR^+$ cells were detected to verify differentiation into γδT cells (FIG. 3B). The obtained cells are hereafter in this Example referred to as "iPS cell-derived γδT cells."

(3-4) Evaluation of Cells on Day 55 of Differentiation Induction

Figure 3C:
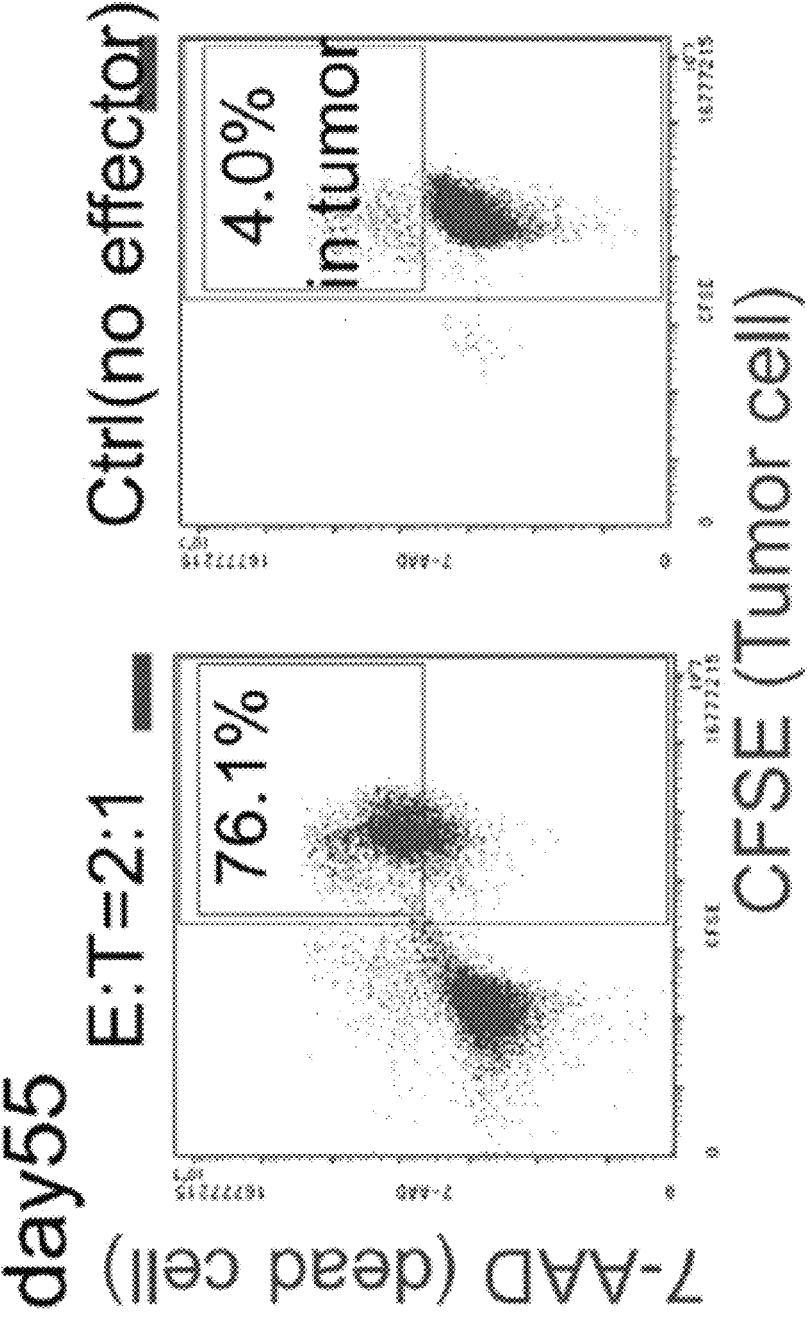
FIG. 3C shows results of determination of cytotoxic activity on Jurkat cells for cells on day 55 of differentiation induction. (Example 3)

Cytotoxicity assay against Jurkat cells was performed. $5×10^4$ Jurkat cells stained with CFSE were added per well of a 96-well culture dish, and $1×10^5$ of the iPS cell-derived γδT cells on day 55 of differentiation induction were further added, followed by 16 hours of culture at E:T ratio=2:1. After that, 7-AAD staining (dead cell staining) was performed. Many of the Jurkat cells (CFSE-positive cells) were 7-AAD-positive, and thus many dead cells were recognized. That is, it was recognized that the iPS cell-derived γδT cells had a cytotoxic function against tumor cells (FIG. 3C).

Figure 4:
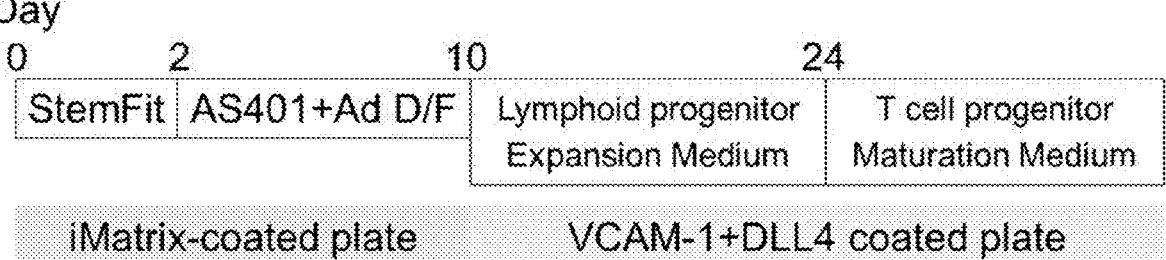
FIG. 4 is an illustration of a protocol for differentiation induction from iPS cells under a condition free from using feeder cells. (Example 4)

(Example 4) Differentiation Induction from iPS Cells Under Condition Free from Using Feeder Cells In this Example, with regard to γδT cells generated by differentiation induction treatment from γδTCR-type iPS cells generated by the method of Non Patent Literature 1 in the same manner as in Example 1, a differentiation induction method under a condition free from using feeder cells is described. In this Example, differentiation induction treatment was performed by the following procedure in accordance with a protocol illustrated in FIG. 4.

(4-1) Until day 8 of differentiation induction treatment, the same treatments as in (1-1) to (1-6) described in Example 1 were performed.

(4-2) Day 10 of Differentiation Induction

With use of a 48-well culture dish coated with VCAM1 and DLL4, a suspension of $1.2×10^4$ of cells on day 10 of differentiation induction in 250 μl of Lymphoid progenitor Expansion Medium included in the StemSpan™ T cell generation kit (Stem Cell Technologies) was seeded per well. PBS(−) having dissolved therein 5 μg/ml VCAM1 and 10 μg/ml DLL4 was added to a commercially available 48-well culture dish that had not been subjected to hydrophilic treatment for cell adhesion (cell culture-non-treated) at 100 μl per well, and the whole was left at rest at 4° C. overnight. The solution was removed, and the culture dish was washed with PBS(−) once and used as a culture dish coated with VCAM1 and DLL4. In the step involving using Lymphoid progenitor Expansion Medium, culture was performed under a condition involving using neither feeder cells nor serum.

(4-3) Thereafter, medium change was performed in accordance with the protocol of the StemSpan™ kit. Specifically, 250 μl of the medium was further added on day 13 of differentiation induction, and half of the medium was changed on each of day 17 and day 20 of differentiation induction. On day 24 of differentiation induction, the medium was changed to T cell progenitor Maturation Medium included in the above-mentioned kit. The above-mentioned medium was further added on day 27 of differentiation induction, and thereafter, half of the medium was changed twice a week, such as day 31 and day 34 of differentiation induction.

Figure 5:
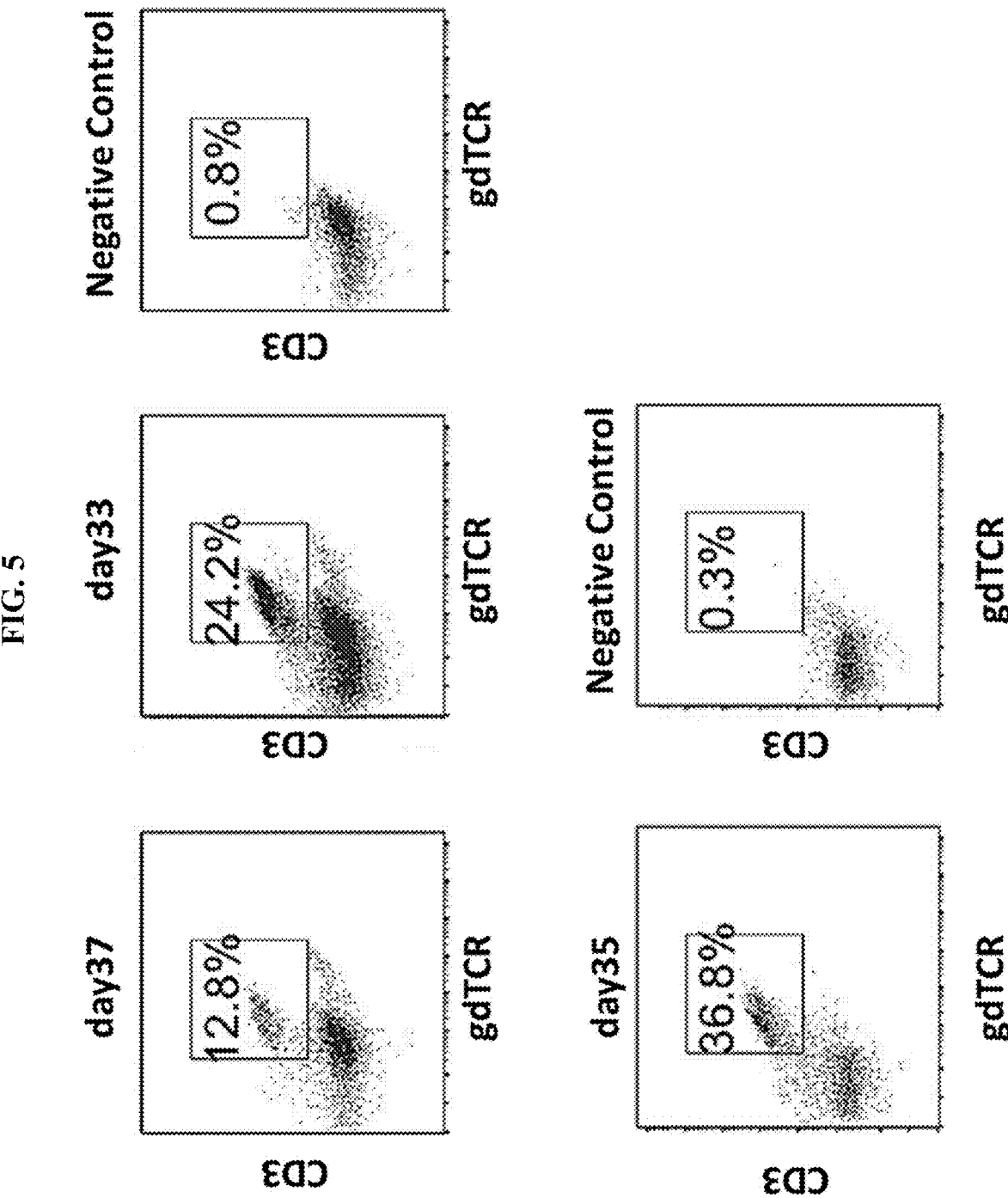
FIG. 5 shows results of evaluation of the expression of CD3/γδTCR by flow cytometry for cells on day 33, day 35, and day 37 of differentiation induction under a condition free from using feeder cells. (Example 4)

(4-4) Evaluation of Cells on Day 33, Day 35, and Day 37 of Differentiation Induction The expression of CD3/γδTCR was evaluated by flow cytometry. A large number of $CD3^+/TCR^+$ cells were detected to verify differentiation into TCR cells and identify the cells as iPS cell-derived γδT cells (FIG. 5). The results shown are the results of three independent differentiation induction experiments. The days on which evaluation was performed (initiation of differentiation induction was defined as day 0) are shown in the figure.

Figure 6:
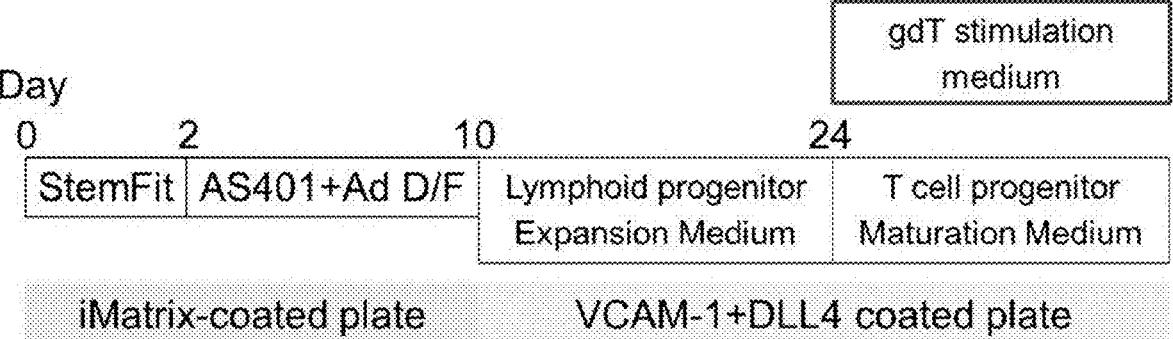
FIG. 6 is an illustration of a protocol for differentiation induction from iPS cells under a condition free from using feeder cells. (Example 5)

(Example 5) Differentiation Induction from iPS Cells Under Condition Free from Using Feeder Cells In this Example, with regard to γδT cells generated by differentiation induction treatment from γδTCR-type iPS cells in the same manner as in Example 4, a differentiation induction method under a condition free from using feeder cells is described. In this Example, differentiation induction treatment was performed by the following procedure in accordance with a protocol illustrated in FIG. 6.

(5-1) The same treatments as in (4-1) to (4-3) of Example 4 were performed, and from day 10 to day 24 of differentiation induction, culture was performed under a condition involving using neither feeder cells nor serum.

(5-2) Day 24 of Differentiation Induction

The medium was changed to the γδT cell stimulation medium (containing HMBPP and FBS) shown in Table 7 in (2-4) of Example 2, and thereafter, half of the medium was changed every 3 days.

(5-3) Evaluation of Cells on Day 37 of Differentiation Induction

Figure 7A:
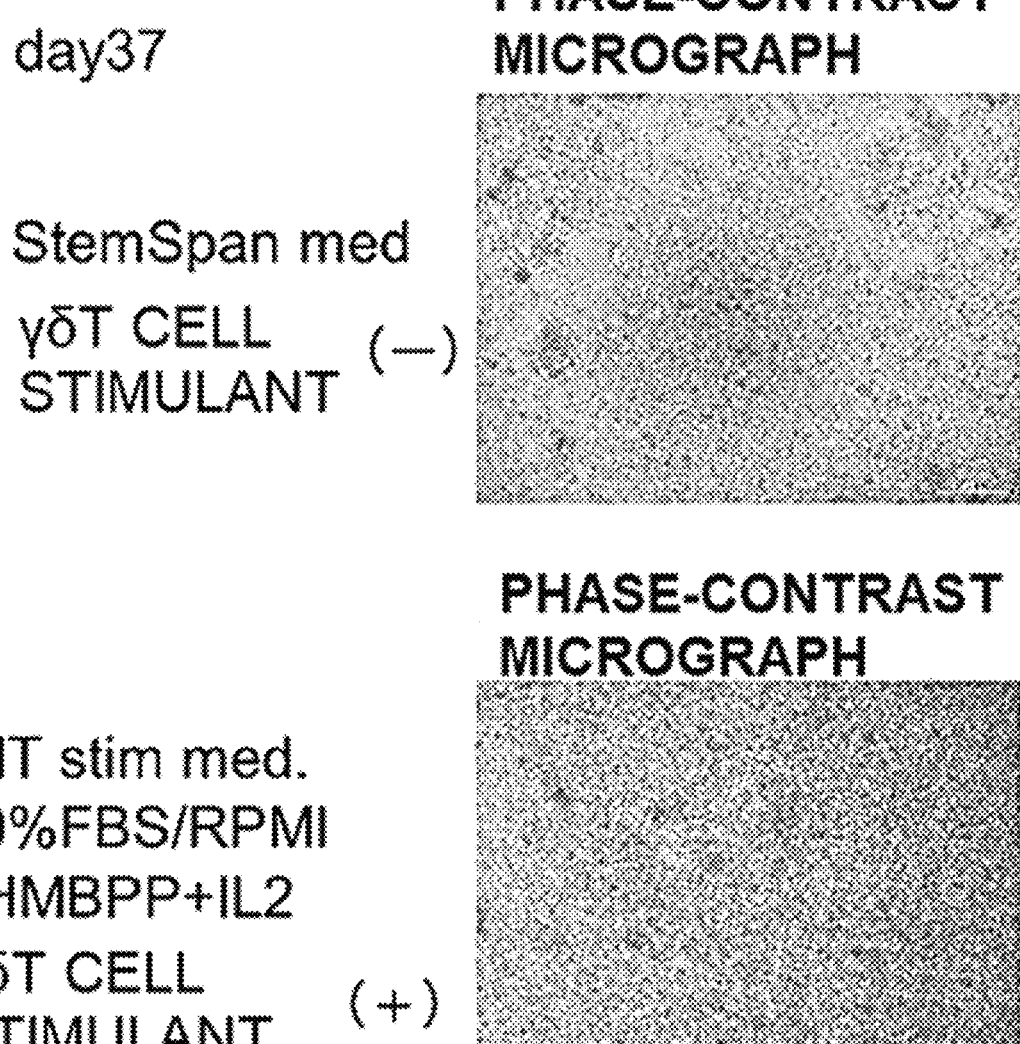
FIG. 7A shows results of observation of cells with a phase-contrast microscope for cells on day 37 of differentiation induction.
Figure 7B:
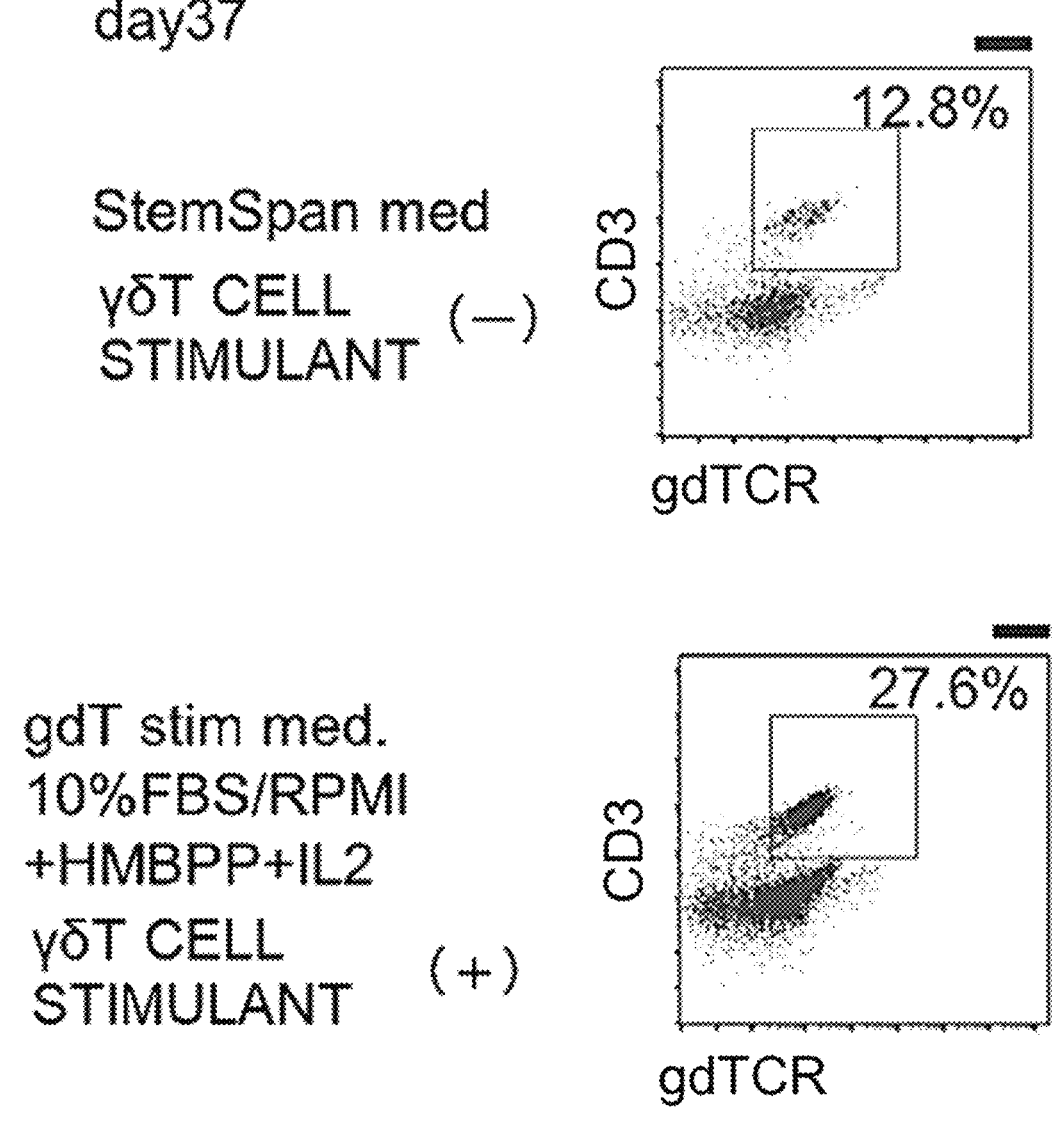
FIG. 7B shows results obtained by further evaluating the expression of CD3/γδTCR by flow cytometry. (Example 5)

The cells were observed for the number of cells using a phase-contrast microscope. The cells generated through culture in the γδT cell stimulant (HMBPP)-free medium in Example 4 were also similarly observed. As a result, when culture was performed in the γδT cell stimulation medium, a clearly larger number of cells were observed (FIG. 7A). Further, the expression of CD3/γδTCR was evaluated by flow cytometry, and as a result, a large number of $CD3^+/TCR^+$ cells were detected to verify differentiation into TCR cells (FIG. 7B). It was recognized that the obtained cells were iPS cell-derived γδT cells.

Figure 8:
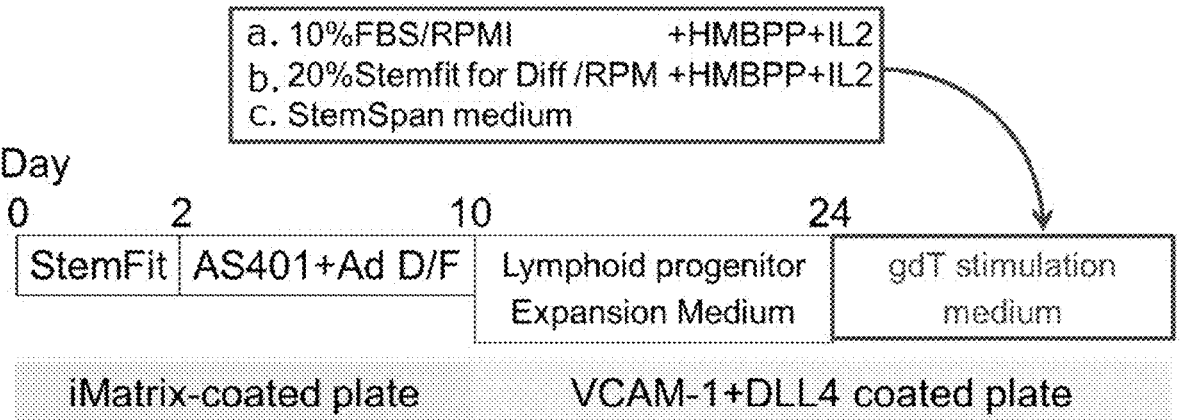
FIG. 8 is an illustration of a protocol for differentiation induction from iPS cells under a condition free from using feeder cells. (Example 6)

(Example 6) Differentiation Induction from iPS Cells Under Condition Free from Using Feeder Cells In this Example, with regard to γδT cells generated by differentiation induction treatment from γδTCR-type iPS cells in the same manner as in Example 4, a differentiation induction method under a condition free from using feeder cells is described. In this Example, differentiation induction treatment was performed by the following procedure in accordance with a protocol illustrated in FIG. 8.

(6-1) The same treatments as in (4-1) to (4-3) of Example 4 were performed, and from day 10 to day 24 of differentiation induction, culture was performed under a condition involving using neither feeder cells nor serum.

(6-2) Day 24 of Differentiation Induction

On day 24 of differentiation induction, the medium was changed to each of a. the γδT cell stimulation medium (containing HMBPP and FBS) shown in Table 7 in (2-4) of Example 2, b. RPMI 1640 (containing HMBPP) medium containing AS401 in place of the basal medium (10% FBS/RPMI 1640) of the γδT cell stimulation medium shown in Table 7, and c. Lymphoid progenitor Expansion Medium included in the StemSpan™ kit, and the medium was changed by the same technique as in (5-2) of Example 5.

(6-3) Evaluation 2 of Cells on Day 32 of Differentiation Induction

Cells on day 32 of differentiation induction were observed for the number of cells using a phase-contrast microscope. In c. the medium included in the StemSpan™ kit, the number of cells is clearly small, whereas in b. the serum-free medium, a cell density equivalent to that in a. the serum medium was observed (FIG. 9). Further, for the above-mentioned cells, the expression of CD3/γδTCR was evaluated by flow cytometry. Under each of the conditions, a large number of CD3$^+$/TCR$^+$ cells were detected to identify the cells as iPS cell-derived γδT cells (FIG. 10). The obtained cells are hereafter in this Example referred to as "iPS cell-derived γδT cells."

(6-4) Evaluation 1 of Cells on Day 35 of Differentiation Induction

Among cells on day 35 of differentiation induction, cells obtained under the a. and b. medium conditions were used and subjected to cytotoxicity assay against Jurkat cells by the same technique as in (1-10) of Example 1. 5×10$^4$ Jurkat cells stained with CFSE were added per well of a 96-well culture dish, 1×10$^5$ of the iPS cell-derived γδT cells on day 35 of differentiation induction were further added, and evaluation was performed after 1 day (d1) and after 4 days (d4) from the initiation of mixed culture at E:T ratio=2:1. As a result, cell aggregates indicating the activation of T cells were found. As compared to a control (ctrl) with no effector cells (iPS cell-derived γδT cells) added, it was observed that the cells obtained under the a. and b. medium conditions clearly appeared to be fewer (FIG. 11). After 1 day from the initiation of mixed culture, cytotoxicity was clear even under the serum-free medium condition b., though to a lesser extent as compared to the a. medium condition, and after 4 days, even more evident cytotoxic activity was recognized (FIG. 12).

(Example 7) Differentiation Induction from iPS Cells Under Condition Free from Using Feeder Cells In this Example, γδT cells were generated by subjecting γδTCR-type iPS cells to differentiation induction treatment in the same manner as in Example 4. [0078](7-1) Culture was performed by performing the same treatments as in (4-1) and (4-2) of Example 4.

(7-2) However, day 10 of differentiation induction was performed under: the same condition (i) as in (4-2); (ii) the condition of adding Dickkopf-1 (DKK1) thereto at a final concentration of 30 ng/ml; (iii) the condition of adding azelaic acid (AZA) thereto at a final concentration of 5 mM; and (iv) the condition of adding both Dickkopf-1 (DKK1) and AZA thereto at the same concentrations as in (ii) and (iii), respectively.

(7-3) Thereafter, medium change was performed in accordance with the protocol of the StemSpan™ kit. That is, 250 μl of each medium described in (7-2) was added on day 13 of differentiation induction, and half of each medium was changed on day 17 and day 20 of differentiation induction.

(7-4) Evaluation of Cells on Day 24 of Differentiation Induction

For cells on day 24 of differentiation induction, the expression of CD7 serving as a T cell differentiation marker was evaluated by flow cytometry. As a result, it was found that DKK1 and AZA each had a positive effect on differentiation induction efficiency, and treatment with combined use thereof achieved a higher effect (FIG. 13).

(Example 8) Differentiation Induction Method Involving Using Magnetic Beads

In this Example, differentiation induction into T cells was performed through mixed culture with magnetic beads coated with VCAM1 and DLL4 instead of coating a culture dish under a condition free from using feeder cells.

(8-1) Until day 8 of differentiation induction treatment, the same treatments as in (1-1) to (1-6) of Example 1 were performed.

(8-2) Preparation of Solution of Magnetic Beads Coated with VCAM1 and DLL4

Magnetic beads (Dynabeads™ Protein G (manufactured by Invitrogen)) were vortexed, 5 μl thereof and 1 ml of PBS were placed into a tube, and the tube was left at rest on a magnetic stand for magnetic bead capture for 1 minute. PBS was removed, and the tube was removed from the stand, followed by the addition of 200 μl of PBS, 4.26 μl of VCAM1 (100 μg/ml solution), and 4.26 μl of DLL4 (100 μg/ml solution). The tube was left at rest at room temperature for 15 minutes. The tube was left at rest on the magnetic stand for 1 minute, the solution was removed, and the tube was removed from the stand. 500 μl of Lymphoid progenitor Expansion Medium included in the StemSpan™ kit was added, and pipetting was performed for suspension.

(8-3) Day 10 of Differentiation Induction 4.75×10$^5$ of the cells generated in (8-1) described above were suspended in 500 μl of the magnetic bead solution prepared in (8-2), seeded into a 24-well low-attachment culture dish (PrimeSurface™), and cultured.

(8-4) 500 μl of the above-mentioned medium was added on day 13 of differentiation induction, and half of the medium was changed on each of day 17 and day 20 of differentiation induction.

(8-5) Evaluation of Cells on Day 24 of Differentiation Induction

For cells on day 24 of differentiation induction, the expression of CD7 serving as a T cell differentiation marker was evaluated by flow cytometry. As a result, it was recognized that, although at a ratio as low as 0.3%, CD7-positive cells were clearly present as compared to a control (isotype control). That is, it was revealed that differentiation into T cells was also able to be performed by this method involving mixed culture with magnetic beads (FIG. 14).

(Example 9) γδT Cells Generated from γδTCR-Type iPS Cells

In this Example, the characteristics of γδT cells generated from γδTCR-type iPS cells (iPS cell-derived γδT cells) were determined. First, a method of generating iPS cell-derived γδT cells is described, and then various characteristics of the cells are described.

(9-1) Method of Generating iPS Cell-Derived γδT Cells

γδT cells were generated by a method illustrated in FIG. 15.

Establishment of iPS Cells

γδTCR-type iPS cells generated by the method of Non Patent Literature 1 were used. Stemfit™ AK02N (Ajinomoto) was used for maintenance culture of the iPS cells. 0.5×TrypLE™ select (manufactured by Thermo Fisher) was used for passage. In each step of differentiation induction treatment into hematopoietic progenitor cells, a 6-well culture plate was used, and cells were seeded at $2 \times 10^3$ cells/well. Every day, the medium was aspirated, and the entire medium of 2.0 ml/well was changed.

Day 0 of Differentiation Induction: State of γδTCR-Type iPS Cells (HPC1)

Stemfit AK02N (Ajinomoto, Tokyo, Japan, AK02N)

CHIR99021 (Tocris, Bristol, UK, 4423) 4 M

BMP4 (R&D, Minneapolis, MN, 314-BP) 80 ng/ml

VEGF (R&D, Minneapolis, MN, 293-VE) 80 ng/ml

Day 2 of Differentiation Induction: (HPC2)

Essential 6 (Thermofisher, Waltham, MA, A1516501)

SB431542 (WAKO, Osaka, Japan, 033-24631) 2 M bFGF (WAKO, Osaka, Japan, 060-04543) 50 ng/ml SCF (R&D, Minneapolis, MN, 255-SC) 50 ng/ml VEGF (R&D, Minneapolis, MN, 293-VE) 80 ng/ml Day 4 of Differentiation Induction: (HPC3)

StemPRO34SFM (Thermofisher, Waltham, MA, 10639-011)

L-Glutamine (Life technologies, 25036-081) 2 mM

IL-3 (Peprotech, Cranbury, NJ, AF-200-03) 50 ng/ml

IL-6 (R&D, Minneapolis, MN, 206-IL) 50 ng/ml

FLT3L (R&D, Minneapolis, MN, 308-FK) 50 ng/ml

SCF (R&D, Minneapolis, MN, 255-SC) 50 ng/ml

VEGF (R&D, Minneapolis, MN, 293-VE) 20 ng/ml

EPO (Kyowa Kirin, Tokyo, Japan) 10 IU/ml

Day 6 and Day 8 of Differentiation Induction: (HPC4)

StemPRO34SFM (Thermofisher, Waltham, MA, 10639-011)

L-Glutamine (Life technologies, 25036-081) 2 mM

IL-6 (R&D, Minneapolis, MN, 206-IL) 50 ng/ml

SCF (R&D, Minneapolis, MN, 255-SC) 50 ng/ml

EPO (Kyowa Kirin, Tokyo, Japan) 10 IU/ml

Day 10~ of Differentiation Induction: Culture on Feeder Cells (OP9/N-DLL1) in T Cell Differentiation Medium Described Below Accutase (Nacalai Tesque, Kyoto, Japan, 12679-54) was used for the passage of the cells. Thereafter, half of the medium was changed every 2 days. In addition, on day 12, day 18, and day 24, the supernatant was collected by pipetting and seeded onto fresh feeder cells (OP9/N-DLL1).

(T Cell Differentiation Medium)

αMEM (Gibco, 11900-016)

FBS (Sigma-Aldrich, St. Louis, MO, F7524) 20%

SCF (R&D, Minneapolis, MN, 255-SC) 10 ng/ml

TPO (R&D, Minneapolis, MN) 10 ng/ml

IL-7 (R&D, Minneapolis, MN, 207-IL) 5 ng/ml

FLT3L (R&D, Minneapolis, MN, 308-FK) 5 ng/ml

L-ascorbic acid (Nacalai Tesque, Kyoto, Japan, 30264-56) 100 µg/ml

Day 30~ of Differentiation Induction: Culture in γδT Activation Medium

The cells treated with Accutase were suspended in a γδT activation medium described below, and cultured in a feeder cell-free medium. Thereafter, half of the medium was changed every 2 days. Cells on days 7 to 14 of activation culture were subjected to cytotoxicity assay.

(γδT Activation Medium)

RPMI 1640 (Nacalai Tesque, Kyoto, Japan, 30264-56)

FBS (Sigma-Aldrich, St. Louis, MO, F7524) 10%

HMBPP (Cayman chemical, Ann Arbor, MI, 13580) 1 nM

Immunace (Shionogi pharmaceuticals, Osaka, Japan) 100 IU/ml

2-Me (Nacalai Tesque, Kyoto, Japan) 10 M (9-2) Process of Differentiation from γδTCR-Type iPS Cells into γδT Cells The morphology of cells in the process of differentiation was observed with a phase-contrast microscope (FIG. 16A), and cell surface markers were determined by flow cytometry (FIG. 16B).

d0: day 0 of differentiation induction: γδTCR-type iPS cells d10: day 10 of differentiation induction: cells differentiated into hematopoietic progenitor cells d30: day 30 of differentiation induction: γδT cells before activating stimulation of γδT cells d51: day 51 of differentiation induction: γδT cells after activating stimulation of γδT cells (9-3) Antitumor Effect With use of iPS cell-derived γδT cells on day 38 of differentiation induction, antitumor activity on various tumor cells was determined (FIG. 17). In these experiments, unpurified γδT cells were used. As a control, the condition of culturing tumor cells alone without the addition of the γδT cells was used.

A. Cytotoxicity assay against Jurkat cells (derived from human leukemia T cells) was performed. At effector:target (E:T) ratio=2:1, $5 \times 10^4$ Jurkat cells stained with a fluorescent dye CFSE were added per well of a 96-well culture dish, and $1 \times 10^5$ of the iPS cell-derived γδT cells were added thereto, followed by 16 hours of culture. After that, dead cells were stained by 7-AAD staining. As compared to the control, the γδT cells of the present invention clearly had higher cytotoxic activity on the Jurkat cells (FIG. 17A).

B. Cytotoxicity assay against Huh-7 cells (derived from human hepatoma cells) was performed. At effector:target (E:T) ratio=2:1, $5 \times 10^4$ Huh-7 cells stained with a fluorescent dye CFSE were added per well of a 96-well culture dish, and $1 \times 10^5$ of the iPS cell-derived γδT cells were added thereto, followed by 16 hours of culture. After that, observation with a phase-contrast microscope was performed to measure a tumor area. As compared to the control, the γδT cells of the present invention clearly had higher cytotoxic activity on the Huh-7 cells (FIG. 17B).

C. Cytotoxicity assay against SW480 cells (derived from human colon cancer) was performed. At effector:target (E:T) ratio=2:1, $5 \times 10^4$ SW480 cells stained with a fluorescent dye CFSE were added per well of a 96-well culture dish, and $1 \times 10^5$ of the iPS cell-derived γδT cells were added thereto, followed by 16 hours of culture. After that, observation with a phase-contrast microscope was performed to measure a tumor area. As compared to the control, the γδT cells of the present invention clearly had higher cytotoxic activity on the SW480 cells (FIG. 17C).

D. In the mixed culture of the iPS cell-derived γδT cells (E) and the Jurkat cells (T), the E:T ratio was gradually changed. A live cell rate at 0:1 was defined as 100%, and live cell rates were compared (FIG. 17D).

(9-4) Retention of TCR Rearrangement and Cytotoxic Mechanism

The retention of TCR rearrangement and a cytotoxic mechanism were determined using iPS cell-derived γδT cells on day 36 of differentiation induction (FIG. 18).

A. For unpurified iPS cell-derived γδT cells (igdT) and peripheral blood mononuclear cells (PB), the expression of an αβTCR on the cell surface was evaluated. The expression of the αβTCR was detected in PB, but the expression of the αβTCR was not detected in the γδT cells (igdT) of the present invention (FIG. 18A).

B. Genomic PCR for TCR Gene Rearrangement

The rearrangement of TCR genes (Vg9 and Vd2) was determined by genomic PCR. It was recognized that γδT cells (igdT) sorted by flow cytometry retained TCR gene rearrangement like the undifferentiated (undiff) state (FIG. 18B). Peripheral blood mononuclear cells (PBMC) were used as a positive control.

C. iPS cell-derived γδT cells (igdT) whose CD3 had been labeled in advance and Jurkat cells were cocultured under 3 μg/ml Brefeldin A. It was recognized that the iPS cell-derived γδT cells expressed granzyme B and perforin (FIG. 18C). As granzyme B and perforin are molecular entities of a cytotoxic function by T cells, it was recognized that the iPS cell-derived γδT cells of the present invention had cytotoxicity.

D. γδT cells (igdT) purified by flow cytometry (FACS) were subjected to cytotoxicity assay. The cytotoxicity assay was performed under the conditions of the method described in A. of (9-3). Jurkat cells cultured alone without the addition of the iPS cell-derived γδT cells were used as a control (ctrl) in FIG. 18D. In addition, the unpurified iPS cell-derived γδT cells are indicated as bulk, and the purified iPS cell-derived γδT cells are indicated as sort. Whether or not the iPS cell-derived γδT cells were purified did not make a large difference in dead cell rate (FIG. 18D).

E. HLA Types of iPS Cell Lines and Tumor Cells

The results of determination of the HLA types of the iPS cells used for the iPS cell-derived γδT cells of the present invention, and respective tumor cells used in Examples 3 and 6 and this Example are shown in Table 8. The HLA types of the iPS cells do not coincide with the HLA types of the respective tumor cells, but antitumor actions were found on the respective tumor cells (this Example, A. to C.). Thus, it was recognized that the iPS cell-derived γδT cells of the present invention had antigen-specific cytotoxic activity in a MHC-unrestricted manner.

TABLE 8

|  | HLA-A | | HLA-B | | HLA-C | | HLA-DRB1 | |
|---|---|---|---|---|---|---|---|---|
| 62B3* | 02:01 | 24:02 | 40:01 | 54:01 | 01:02 | 03:04 | 04:03 | 04:05 |
| 121-3* | 24:01 | 31:01 | 35:01 | 52:01 | 04:01 | 12:02 | 09:01 | 13:02 |
| Jurkat** | 03:01 | — | 07:02 | 35:03 | 04:01 | 07:02 | 07:01 | 15:01 |
| Huh-7** | 11:01 | — | 54:01 | — | 01:02 | — | 08:03 | — |
| SW480** | 02:01 | 24:02 | 07:02 | 15:18 | 07:02 | 07:04 | 01:03 | 13:01 |

*iPS cell line
**tumor cell line (Example 10) Comparison of iPS Cell-Derived γδT Cells and γδT Cells Separated from Peripheral Blood In this Example, cell surface expression marker genes in iPS cell-derived γδT cells (igdT) generated by inducing differentiation of iPS cells and γδT cells (PB-gdT) present in peripheral blood were compared. For the iPS cell-derived γδT cells of this Example, culture was performed by the method described in Example 1 and the method described in (9-1) of Example 9, and cells on day 36 to day 42 of differentiation induction were used. Cells obtained by culturing mononuclear cells separated from peripheral blood in the γδT activation medium described in (9-1) of Example 9 were used as γδT cells separated from peripheral blood of this Example.

(10-1) Single-Cell RNA-Seq Analysis

The iPS cell-derived γδT cells, and the γδT cells separated from peripheral blood and cells in peripheral blood excluding the γδT cells were analyzed for differences in marker gene expression by single-cell RNA-seq analysis. As a result, different expression patterns were shown for each of CD7, CD8a, IL18R1, IL2RA (CD25), IL2RB, and IFNγ (FIG. 19, Table 9).

TABLE 9

| igdT > PB-gdT | CD7, CD8a |
|---|---|
| igdT = PB-gdT | CD3E, δTCR, IL2RB, IL18R1, Perforin, Granzyme B, NKG7 |
| igdT < PB-gdT | IL2RA, IFNγ |

(10-2) Analysis of CD25 by Flow Cytometry

The expressions of CD25 in the iPS cell-derived γδT cells and the γδT cells separated from peripheral blood were compared by flow cytometry. iPS cell-derived TCR-Vγ9-positive cells were mostly CD25-negative cells, whereas TCR-Vγ9-positive cells separated from peripheral blood were mostly CD25-positive cells (FIG. 20).

Thus, it was recognized that the iPS cell-derived γδT cells and the γδT cells separated from peripheral blood had different patterns of cell surface markers.

(Example 11) Method of Activating iPS Cell-Derived γδT Cells

In this Example, a method of activating iPS cell-derived γδT cells was investigated. Specifically, for cells on day 30 of differentiation induction in the generation method described in (9-1) of Example 9, an investigation was performed as to which of IL-2 and/or IL-15 enabled more effective generation of iPS cell-derived γδT cells when the following γδT activation medium was further supplemented therewith (see FIG. 21).

(Activation Medium)

RPMI 1640 (Nacalai Tesque, Kyoto, Japan, 30264-56)

FBS (Sigma-Aldrich, St. Louis, MO, F7524) 10%

HMBPP (Cayman chemical, Ann Arbor, MI, 13580) 1 nM

2-Me (Nacalai Tesque, Kyoto, Japan) 10 M

According to the results of evaluations of live cell counts and CD3⁺γδT cells, the supplementation with IL-15 was preferred to IL-2, and IL-15 alone was more effective even when compared to its combined use with IL-2 (FIG. 22).

(Example 12) Characteristics of γδT Cells Generated from γδTCR-Type iPS Cells (121-3 Line)

In this Example, the characteristics of γδT cells generated from γδTCR-type iPS cells (121-3 line) were determined.

(12-1) In this Example, the 121-3 line was used instead of the 62B3 line as the γδTCR-type iPS cells, culture was performed by the method described in (9-1) of Example 9, and cells on day 36 of differentiation induction were used.

(12-2) Retention of TCR Rearrangement

A. The rearrangement of TCR genes (Vγ9 and Vγ2) of the γδT cells (iγδT) obtained by differentiation induction from the γδTCR-type iPS cells (121-3 line) was determined by genomic PCR. It was recognized that iγδT sorted by flow cytometry retained TCR gene rearrangement like the undifferentiated (undiff) state (FIG. 23A).

B. The sequences of the TCRγs and TCRδs of the γδT cells (iγδT) obtained by differentiation induction from the γδTCR-type iPS cells (121-3 line) and γδT cells (PBγδT) obtained by subjecting peripheral blood mononuclear cells to expansion culture were analyzed with a next-generation sequencer. The base sequences and amino acid sequences of the CDR3 regions of their respective TCRγs and TCRδs were identified, and the frequencies of each sequence were shown as pie charts (FIG. 23B). It was recognized that the PBγδT cell population was made up of cells having diverse sequences, whereas the iγδT cell population was made up of cells all harboring a single kind of TCRγ and TCRδ gene rearrangement.

(Example 13) Characteristics of iPS-Derived γδT Cells Generated from γδTCR-Type iPS Cells (62B3 Line)

In this Example, with regard to iPS-derived γδT cells generated by the generation method described in Example 9, the expression of IFNγ was evaluated by flow cytometry for cells obtained by coculturing cells on day 39 of differentiation induction with Jurkat cells for 4 hours.

The expression of interferon gamma (IFNγ) as well as the expression of granzyme B in iPS cell-derived γδT cells (iγδT) and γδT cells (PBγδT) obtained by subjecting peripheral blood mononuclear cells to expansion culture was evaluated with a flow cytometer. The results showed that granzyme B was expressed in both the cell populations, whereas IFNγ was recognized to be expressed only in PBγδT and not recognized to be expressed in iγδT (FIG. 24).

(Example 14) Comparison of iPS Cell-Derived γδT Cells and γδT Cells Obtained by Expanding Peripheral Blood In this Example, cell surface expression markers in iPS cell-derived γδT cells (igdT) generated by inducing differentiation of γδTCR-type iPS cells (62B3 line or 121-3 line) and γδT cells (PB-gdT) obtained by expanding peripheral blood were compared.

(14-1) Culture was performed by a method involving using feeder cells through the same treatment as in (9-1) of Example 9.

(14-2) The expressions of various cell surface markers (CD25, CD7, CD5, CD45RA, and CD27) in a cell population (iγδT) including γδT cells for cells on day 40 of differentiation induction and a cell population (CD3-positive or TCRγ9-positive) including γδT cells (PBγδT) obtained by subjecting peripheral blood mononuclear cells to expansion culture were evaluated with a flow cytometer. It was recognized that, as compared to PBγδT, the iPS cell-derived γδT cells (CD3-positive or TCRγ9-positive cells among iγδT) had the following features: the ratio of cells expressing CD7 was high, the ratio of cells expressing CD5 and CD25 was low, and the ratio of CD45RA⁺CD27⁻ cells was high (FIG. 25).

(Example 15) Investigation of Step of Stimulating γδT Cells

In this Example, with regard to γδT cells generated by differentiation induction treatment from γδTCR-type iPS cells in the same manner as in Example 5, description is made of a differentiation induction method under a condition involving using neither feeder cells nor serum and a condition of performing the step of stimulating γδT cells not from day 24 but from day 17. In this Example, differentiation induction was performed by the following procedure in accordance with a protocol illustrated in FIG. 26A (New protocol).

(15-1) Culture was performed by performing the same treatment as in (5-1) of Example 5. However, the step of stimulating γδT cells was performed from day 17 of differentiation induction.

(15-2) Evaluation of Cells on Day 17 of Differentiation Induction

For cells on day 17 of differentiation induction, the expression of CD3/γδTCR (gdTCR) was evaluated by flow cytometry. CD3⁺/TCR⁺ cells were detected to verify differentiation into TCR cells and identify the cells as iPS cell-derived γδT cells (FIG. 26B). The obtained cells are hereafter in this Example referred to as "iPS cell-derived γδT cells."

(15-3) Day 17 of Differentiation Induction

The medium was changed to a medium obtained by using RPMI 1640 containing 20% AS401 as a basal medium, and adding 1 nM HMBPP (Cayman chemical, Ann Arbor, MI, 13580) and 100 ng/ml IL2 (Reprotech, 200-02) thereto, and thereafter, half of the medium was changed every 3 days.

(15-4) Day 24 of Differentiation Induction

Further, for cells on day 24 of differentiation induction, the expression of CD3/CD7 was evaluated by flow cytometry (FIG. 26C). iPS cell-derived γδT cells were obtained even under the condition of shortening the step of stimulating γδT cells.

(Example 16) Method of Activating iPS Cell-Derived γδT Cells Under Condition Free from Using Feeder Cells In this Example, a method of activating iPS cell-derived γδT cells under a condition involving using neither feeder cells nor serum was investigated.

A. Culture was performed under a condition involving using neither feeder cells nor serum through the same treatments as in (15-1) and (15-3) of Example 15. However, cells on day 17 of differentiation induction were treated under the same condition as in (15-3) of Example 15 as well as the condition of changing IL-2 in (15-3) to IL-15. On day 33 or day 37 of differentiation induction, the expression of CD3/γδTCR was evaluated by flow cytometry regarding whether iPS cell-derived γδT cells were able to be more effectively generated. CD3⁺/TCR⁺ cells were detected to verify differentiation into TCR cells and identify the cells as iPS cell-derived γδT cells (FIG. 27A). It was able to be recognized that iPS cell-derived γδT cells were able to be generated by using any one of IL-2 or IL-15 in the step of stimulating γδT cells. In addition, as compared to IL-2, the addition of IL-15 provided more iPS cell-derived γδT cells.

B. Differentiation induction treatment was performed using IL-15 in the step of stimulating γδT cells in A above, and an investigation was performed as to whether iPS cell-derived γδT cells were able to be generated with or without the addition of HMBPP. For cells on day 23 of differentiation induction, the expression of CD3/CD7 was evaluated by flow cytometry. CD3$^+$/TCR$^+$ cells were detected to verify differentiation into TCR cells and identify the cells as iPS cell-derived γδT cells. iPS cell-derived γδT cells were obtained even under the condition of not adding the γδTCR stimulant HMBPP (FIG. 27B).

(Example 17) Cytotoxic Activity after Freezing and Thawing of iPS Cell-Derived γδT Cells In this Example, iPS cell-derived γδT cells under a condition involving using neither feeder cells nor serum were frozen and thawed, and subjected to cytotoxicity assay.
(17-1) Culture was performed under a condition involving using neither feeder cells nor serum through the same treatments as in (15-1) and (15-3) of Example 15. However, IL-2 in (15-3) of Example 15 was changed to IL-15. On day 24 of differentiation induction, the cells were frozen using CS10 (manufactured by Cosmo Bio).
(17-2) Evaluation of Cells on Day 24 of Differentiation Induction
The frozen cells were thawed 2 weeks later and subjected to cytotoxicity assay against Jurkat cells. At effector:target (E:T) ratio=2:1, 5×10$^4$ Jurkat cells stained with a fluorescent dye CFSE were added per well of a 96-well culture dish, and 1×10$^5$ of the iPS cell-derived γδT cells on day 24 of differentiation induction were added thereto, followed by 16 hours of culture. Dead cells were stained by 7-amino-actinomycin D (7-AAD) staining. Cell death (7-AAD-positive) was recognized for many of the Jurkat cells (CFSE-positive cells) (FIG. 28). That is, it was recognized that the iPS cell-derived γδT cells had a cytotoxic function even after freezing and thawing.

(Example 18) Differentiation Induction after Freezing and Thawing of iPS Cell-Derived Hematopoietic Progenitor Cells In this Example, iPS cell-derived hematopoietic progenitor cells were frozen and thawed, and then subjected to differentiation induction to generate γδT cells.
(18-1) Evaluation of Cells on Day 10 of Differentiation Induction
The same treatments as in (1-1) to (1-6) shown in Example 1 were performed, and cells on day 10 of differentiation induction were evaluated by flow cytometry and recognized to be in the stage of hematopoietic progenitor cells (FIG. 29A).
(18-2) Day 10 of Differentiation Induction
The above-mentioned cells were frozen using CS10 (manufactured by Cosmo Bio) and thawed about 1 year later. After the thawing, differentiation induction was performed by a method involving using feeder cells through the same treatment as in (9-1) of Example 9.
(18-3) Evaluation 1 of Cells on Day 37 of Differentiation Induction
For cells on day 37 of differentiation induction (at a differentiation induction culture period of 37 days including days before and after the freezing), the expression of CD3/γδTCR was evaluated by flow cytometry. CD3$^+$/TCR$^+$ cells were detected, and hence the cells were identified as iPS cell-derived γδT cells (FIG. 29B). Further, the cells on day 37 of differentiation induction were subjected to cytotoxicity assay against Jurkat cells. At effector:target (E:T) ratio=2:1, 5×10$^4$ Jurkat cells stained with a fluorescent dye CFSE were added per well of a 96-well culture dish, and 1×10$^5$ of the iPS cell-derived γδT cells on day 24 of differentiation induction were added thereto, followed by 16 hours of culture. Dead cells were stained by 7-amino-actinomycin D (7-AAD) staining. Cell death (7-AAD-positive) was recognized for many of the Jurkat cells (CFSE-positive cells) (FIG. 29C). That is, it was recognized that the iPS cell-derived γδT cells had a cytotoxic function even after freezing and thawing.

(Example 19) Differentiation Induction Under Condition Involving Using Neither Feeder Cells Nor Serum after Freezing and Thawing of iPS Cell-Derived Hematopoietic Progenitor Cells In this Example, iPS cell-derived hematopoietic progenitor cells were frozen and thawed, and then subjected to differentiation induction under a condition involving using neither feeder cells nor serum to generate γδT cells. In this Example, differentiation induction was performed by the following procedure in accordance with a protocol illustrated in FIG. 30A. The freezing in this Example was performed for 18 days.
(19-1) Until day 8 of differentiation induction, the same treatments as in (1-1) to (1-6) shown in Example 1 were performed. The cells were frozen using CS10 (manufactured by Cosmo Bio) on day 10 of differentiation induction and thawed 18 days later.
(19-2) Day 10 of Differentiation Induction
For the cells after the thawing, with use of a 48-well culture dish coated with VCAM1 and DLL4, a suspension of 1.2×10$^4$ of the cells on day 10 of differentiation induction in a medium obtained by supplementing Lymphoid progenitor Expansion Medium included in the StemSpan™ T cell generation kit (Stem Cell Technologies) with DKK1 at a final concentration of 30 ng/ml and azelaic acid (AZA) at a final concentration of 5 mM was seeded per well. PBS(–) having dissolved therein 5 μg/ml VCAM1 and 10 μg/ml DLL4 was added to a commercially available 48-well culture dish that had not been subjected to hydrophilic treatment for cell adhesion (cell culture-non-treated) at 100 μl per well, and the whole was left at rest at 4° C. overnight. The solution was removed, and the culture dish was washed with PBS(–) once and used as a culture dish coated with VCAM1 and DLL4.
(19-3) Thereafter, medium change was performed in accordance with the protocol of the StemSpan™ kit. Specifically, 250 μl of the medium was further added on day 13 of differentiation induction.
(19-4) Day 17 of Differentiation Induction
On day 17 of differentiation induction, differentiation induction was performed under a condition involving using neither feeder cells nor serum by the same technique as in (15-3) of Example 15 except for changing IL-2 in (15-3) of Example 15 to IL-15. Thus, γδT cells were generated.
(19-5) Evaluation of Cells on Day 17 of Differentiation Induction
For cells on day 17 of differentiation induction (at a differentiation induction culture period of 17 days including days before and after the freezing), the expression of CD3/γδTCR was evaluated by flow cytometry. CD3$^+$/TCR$^+$ cells were detected, and hence the cells were identified as iPS cell-derived γδT cells (FIG. 30B).

(19-6) Evaluation of Cells on Day 24 of Differentiation Induction

Cells on day 24 of differentiation induction (at a differentiation induction culture period of 24 days including days before and after the freezing) were subjected to cytotoxicity assay against Jurkat cells. At effector:target (E:T) ratio=2:1, $5 \times 10^4$ Jurkat cells stained with a fluorescent dye CFSE were added per well of a 96-well culture dish, and $1 \times 10^5$ of the iPS cell-derived γδT cells on day 24 of differentiation induction were added thereto, followed by 16 hours of culture. Dead cells were stained by 7-amino-actinomycin D (7-AAD) staining. Cell death (7-AAD-positive) was recognized for many of the Jurkat cells (CFSE-positive cells) (FIG. 30C).

(Example 20) Differentiation Induction from Hematopoietic Progenitor Cells Under Hypoxic Condition This Example was carried out under a condition involving using neither feeder cells nor serum. However, γδT cells were generated by performing differentiation induction from hematopoietic progenitor cells under a hypoxic condition. In this Example, differentiation induction was performed by the following procedure in accordance with a protocol illustrated in FIG. 31A.

(20-1) The same treatments as in (4-1) and (4-2) of Example 4 were performed.

(20-2) However, cells on day 10 of differentiation induction were cultured under a condition involving using neither feeder cells nor serum in a medium obtained by supplementing Lymphoid progenitor Expansion Medium included in the StemSpan™ T cell generation kit (Stem Cell Technologies) described in (4-2) of Example 4 with DKK1 at a final concentration of 30 ng/ml and azelaic acid (AZA) at a final concentration of 5 mM, with the $O_2$ concentration being changed from 20% to 5%.

(20-3) Thereafter, medium change was performed in accordance with the protocol of the StemSpan™ kit. Specifically, 250 μl of the medium described in (20-2) was further added on day 13 of differentiation induction.

(20-4) Evaluation of Cells on Day 17 of Differentiation Induction

For cells on day 17 of differentiation induction, the expression of CD3/D7 was evaluated by flow cytometry (FIG. 31B). CD3$^+$/CD7$^+$ cells were detected, and hence the cells were identified as iPS cell-derived γδT cells. It was able to be recognized that both the ratio and absolute number of iPS cell-derived γδT cells were high under the hypoxic (5% $O_2$) condition as compared to 20% $O_2$.

(20-5) Day 17 of Differentiation Induction

Culture was performed by changing the $O_2$ concentration from 20% to 5% in the same treatment as in (19-4) of Example 19.

(20-6) Day 29 of Differentiation Induction

Cells on day 29 of differentiation induction were subjected to cytotoxicity assay against Jurkat cells. At effector:target (E:T) ratio=2:1, $5 \times 10^4$ Jurkat cells stained with a fluorescent dye CFSE were added per well of a 96-well culture dish, and $1 \times 10^5$ of the iPS cell-derived γδT cells on day 29 of differentiation induction were added thereto, followed by 16 hours of culture. Dead cells were stained by 7-amino-actinomycin D (7-AAD) staining. Cell death (7-AAD-positive) was recognized for many of the Jurkat cells (CFSE-positive cells) (FIG. 31C). That is, the cytotoxic activity under the hypoxic condition was more effective than that induced under the normoxic condition.

(Example 21) Differentiation Induction from iPS Cells Under Animal-Derived Component-Free Medium Condition In this Example, iPS cell-derived γδT cells were generated under an animal-derived component-free medium condition.

(21-1) The same treatments as in (4-1) and (4-2) of Example 4 were performed.

(21-2) However, on day 10 of differentiation induction, differentiation induction was performed by the same technique as in (4-2) of Example 4 using a medium obtained by changing the basal medium from 20% FBS/αMEM to 20% AS401/RPMI 1640 in Table 6 of Example 2 while omitting the use of feeder cells (resulting in an animal-derived component-free medium condition) in place of Lymphoid progenitor Expansion Medium shown in (4-2) of Example 4. Thus, γδT cells were generated. 250 μl of the medium was added on day 13 of differentiation induction.

(21-3) Evaluation of Cells on Day 17 of Differentiation Induction

For cells on day 17 of differentiation induction, the expression of CD3/CD7 was evaluated by flow cytometry. CD3$^+$/CD7$^+$ cells were detected, and hence the cells were identified as iPS cell-derived γδT cells (FIG. 32A).

(21-4) Day 17 of Differentiation Induction

On day 17 of differentiation induction, differentiation induction and culture were performed by the same technique as in (2-4) of Example 2 except for changing the basal medium from 20% FBS/αMEM to 20% AS401/RPMI 1640 and changing IL-2 to IL-15 in Table 7 in (2-4) of Example 2.

(21-5) Day 31 of Differentiation Induction

Cells on day 31 of differentiation induction were subjected to cytotoxicity assay against Jurkat cells. At effector: target (E:T) ratio=2:1, $5 \times 10^4$ Jurkat cells stained with a fluorescent dye CFSE were added per well of a 96-well culture dish, and $1 \times 10^5$ of the iPS cell-derived γδT cells on day 31 of differentiation induction were added thereto, followed by 16 hours of culture. Dead cells were stained by 7-amino-actinomycin D (7-AAD) staining. Cell death (7-AAD-positive) was recognized for many of the Jurkat cells (CFSE-positive cells) (FIG. 32B). Remarkable cytotoxic activity was recognized.

(Example 22) Identification of Undifferentiated Cells with Respect to iPS Cell-Derived γδT Cells This Example was carried out under a condition involving using neither feeder cells nor serum. In this Example, undifferentiated cells were identified with respect to iPS cell-derived γδT cells.

(22-1) The same treatments as in (4-1) and (4-2) of Example 4 were performed.

(22-2) However, cells on day 10 of differentiation induction were cultured under a condition involving using neither feeder cells nor serum in a medium obtained by supplementing Lymphoid progenitor Expansion Medium included in the StemSpan™ T cell generation kit (Stem Cell Technologies) described in (4-2) of Example 4 with DKK1 at a final concentration of 30 ng/ml and azelaic acid (AZA) at a final concentration of 5 mM.

(22-3) Thereafter, medium change was performed in accordance with the protocol of the StemSpan™ kit. Specifically, 250 μl of the medium was further added on day 13 of differentiation induction, and from day 17 of differentiation induction onward, half of the medium was changed twice a week to a medium obtained by using RPMI 1640 containing 20% AS401 as a basal medium, and adding 1 nM HMBPP (Cayman chemical, Ann Arbor, MI, 13580) and 100 ng/ml IL15 thereto.

(22-4) Evaluation 1 of Cell Population on Day 35 of Differentiation Induction

The expression of an undifferentiation marker TRA-1-85 in a cell population on day 35 differentiated under a condition involving using neither feeder cells nor serum was evaluated by flow cytometry. It was recognized that the cell population on day 35 did not include TRA-1-85-positive cells at all. (FIG. 33A)

(22-5) Evaluation 2 of Cell Population on Day 35 of Differentiation Induction

A protocol for determining the appearance of colonies of undifferentiated cells using the cell population on day 35 differentiated under a condition involving using neither feeder cells nor serum is illustrated (FIG. 33B). iPS-derived cell γδT cell population of $1\times10^4$ of cells on day 35 were seeded under the maintenance culture conditions for undifferentiated iPS cells ((1-1) of Example 1), and whether colonies of undifferentiated cells appeared was investigated. As a positive control, $1\times10^2$ undifferentiated iPS cells were mixed. After 11 days, alkaline phosphatase staining (AP staining) was performed. Colonies of undifferentiated cells are stained red by AP staining. A large number of AP staining-positive colonies were recognized under the condition of adding iPS cells serving as a positive control, whereas not a single AP staining-positive colony was recognized in the cell population after differentiation induction without the addition of iPS cells (FIG. 33C).

(Example 23) Cytotoxicity Assay of CD3/γδT-Positive Cells

In this Example, CD3/γδT-positive cells were purified from a cell population obtained by the same treatment as in Example 22, and were subjected to cytotoxicity assay.

Cells on day 35 of differentiation induction were evaluated by flow cytometry before FACS and after FACS (FIG. 34A). CD3/γδTCR (gdTCR)-positive cells were detected, and hence it was recognized that purification had been satisfactorily performed.

The purified cells were subjected to cytotoxicity assay against Jurkat cells. At effector:target (E:T) ratio=0.2:1, $5\times10^4$ Jurkat cells stained with a fluorescent dye CFSE were added per well of a 96-well culture dish, and $1\times10^5$ iPS cell-derived γδT cells on day 35 of differentiation induction were added thereto, followed by 16 hours of culture. Dead cells were stained by 7-amino-actinomycin D (7-AAD) staining and shown as a graph (FIG. 34B). Despite the condition of an E:T ratio of 0.2:1, where the number of attacker (effector) cells was extremely small with respect to the tumor cells, strong cytotoxic activity was shown. It was revealed that it was the CD3/γδT-positive cells (i.e., γδT cells) serving as the cells of interest that had had cytotoxic activity in the cytotoxicity assays previously performed using an unpurified cell population.

INDUSTRIAL APPLICABILITY

As described in detail above, according to the method of generating an iPS cell-derived γδT cell of the present invention, γδT cells can be effectively generated without a burden on a person from which blood is collected, and without being affected by exhaustion of the cells. Further, according to the generation method of the present invention, excellent iPS cell-derived γδT cells can be generated even by a method free from using feeder cells. Moreover, according to the generation method of the present invention, excellent iPS cell-derived γδT cells can be generated even by a method involving using neither feeder cells nor serum, or even a method involving using an animal-derived component-free medium. Further, according to the generation method of the present invention, excellent iPS cell-derived γδT cells can be generated even when frozen and thawed during generation.

The iPS cell-derived γδT cells of the present invention can overcome a problem in that γδT cells in peripheral blood cannot secure the purity and number of cells sufficient for treatment, and a problem in that, when the amount of blood to be collected is increased in order to secure the purity and number of cells sufficient for treatment, a tremendous burden is put on a person from which blood is collected. Further, the iPS cell-derived γδT cells of the present invention can overcome a problem in that the method involving ex vivo expanding γδT cells separated from peripheral blood cannot achieve sufficient expansion and activation owing to difficulty in securing the number of cells, and to exhaustion of the cells, and hence are extremely useful. The cell population of the γδT cells generated by the method of the present invention can be a γδT cell population that is more homogeneous and has a higher effect than a cell population of γδT cells separated from peripheral blood, and has an excellent function of having antigen-specific cytotoxic activity in a MHC-unrestricted manner more effectively. Further, the cell population of the γδT cells generated by the method of the present invention can be a γδT cell population without residual undifferentiated cells, and hence is excellent in clinical application.

The invention claimed is:

1. A method of generating an iPS cell-derived γδ T cell, comprising:

(a) culturing a hematopoietic progenitor cell in a medium obtained by supplementing a basal medium with one kind or a plurality of kinds selected from FMS-like tyrosine kinase 3 ligand (FLT3L), stem cell factor (SCF), IL-2, IL-7, thrombopoietin (TPO), and L-ascorbic acid, wherein the hematopoietic progenitor cell is obtained by differentiation induction treatment of an iPS cell having a rearranged γδ TCR gene; and (b) culturing the cell resulted from step (a) in a medium containing a γδ T cell stimulant, thereby generating an iPS cell-derived γδ T cell, wherein the γδ T cell stimulant is a phosphoric acid compound or a derivative thereof, which is a metabolite of an isoprenoid biosynthesis pathway, or a specific inhibitor of a farnesyl pyrophosphate (FPP) synthase serving as a rate-limiting enzyme of the isoprenoid biosynthesis pathway, and wherein step (b) is initiated 17 to 31 days after the start of the differentiation induction treatment.

2. The method according to claim 1, wherein step (a) comprises co-culturing the hematopoietic progenitor cell with a feeder cell.

3. The method according to claim 1, wherein step (a) comprises culturing the hematopoietic progenitor cell without a feeder cell.

4. The method according to claim 3, wherein step (a) comprises culturing the hematopoietic progenitor cell using a culture substrate coated with: (i) vascular cell adhesion molecule-1 (VCAM1) and (ii) delta-like protein 4 (DLL4) or delta-like protein 1 (DLL1).

5. The method according to claim 3, wherein step (a) further comprises culturing the hematopoietic progenitor cell using a medium containing DKK1 and/or azelaic acid (AZA).

6. The method according to claim 1, wherein the medium containing a γδ T cell stimulant further comprises one kind or a plurality of kinds selected from IL-2 and IL-15.

7. The method according to claim 1, wherein step (a) is performed under a serum-free condition.

8. The method according to claim 1, wherein step (a) is performed under a hypoxic condition.

9. A cell population, comprising the iPS cell-derived γδ T cell generated by the method according to claim 1, wherein 10% or less of the γδ T cells in the cell population are undifferentiated iPS cells.

10. The cell population according to claim 9, having a higher cytotoxic activity in an antigen-specific manner than a cell population of γδ T cells separated from peripheral blood.

11. The cell population according to claim 9, wherein 90% or more of the iPS cell-derived γδ T cells in the cell population have base sequences identical to each other in a CDR3 region of a TCR gene.

12. The cell population according to claim 11, wherein the cell population comprises $1 \times 10^5$ or more iPS cell-derived γδ T cells.

13. A cell population generated according to the method of claim 1 comprising IPS cell-derived γδ T cells, wherein 90% or more of the iPS cell-derived γδ T cells exhibit a higher expression amount of CD7 and/or CD8a than γδ T cells separated from peripheral blood.

14. A method of antigen-specific cellular immunotherapy, comprising administering to a subject in need thereof a therapeutically effective amount of the iPS cell-derived γδ T cell generated according to the method of claim 1.

15. The method according to claim 1, wherein the medium in step (a) contains a bead-like carrier coated with VCAM1 and DLL4.

16. A method for treating a disease, comprising administering to a subject in need thereof a therapeutically effective amount of the cell population according to claim 9, wherein the disease is selected from the group consisting of cancer, infectious diseases, and autoimmune disorders.

17. A pharmaceutical composition, comprising the cell population according to claim 9 as an active ingredient.

18. The method according to claim 3, wherein step (a) is performed under a serum-free condition.

19. The method according to claim 3, wherein step (a) is performed under a hypoxic condition.

20. The method according to claim 1, wherein step (b) is initiated 17 to 24 days after the start of the differentiation induction treatment.

* * * * *